US010957864B2

(12) United States Patent
Parham et al.

(10) Patent No.: US 10,957,864 B2
(45) Date of Patent: Mar. 23, 2021

(54) MATERIALS FOR ORGANIC LIGHT-EMITTING DEVICES

(71) Applicant: Merck Patent GmbH, Darmstadt (DE)

(72) Inventors: Amir Hossain Parham, Frankfurt Am Main (DE); Anja Jatsch, Frankfurt am Main (DE); Tobias Grossmann, Darmstadt (DE); Thomas Eberle, Landau (DE); Jonas Valentin Kroeber, Frankfurt am Main (DE); Rouven Linge, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 42 days.

(21) Appl. No.: 16/404,018

(22) Filed: May 6, 2019

(65) Prior Publication Data
US 2019/0326521 A1    Oct. 24, 2019

Related U.S. Application Data

(63) Continuation of application No. 15/121,108, filed as application No. PCT/EP2015/000147 on Jan. 27, 2015, now abandoned.

(30) Foreign Application Priority Data

Feb. 28, 2014 (EP) .................................. 14000729

(51) Int. Cl.
| H01L 51/00 | (2006.01) |
| C09K 11/06 | (2006.01) |
| C07D 471/20 | (2006.01) |
| C07D 471/22 | (2006.01) |
| C07D 491/20 | (2006.01) |
| C07D 519/00 | (2006.01) |
| C07D 403/10 | (2006.01) |
| C07D 513/04 | (2006.01) |
| C07D 491/147 | (2006.01) |
| C07D 409/04 | (2006.01) |
| C07D 471/16 | (2006.01) |
| C07D 495/14 | (2006.01) |
| C07D 498/04 | (2006.01) |
| C07D 209/96 | (2006.01) |
| C07D 487/04 | (2006.01) |
| C07D 333/76 | (2006.01) |
| C07D 471/14 | (2006.01) |
| C07D 487/10 | (2006.01) |
| C07D 471/04 | (2006.01) |
| C07D 471/10 | (2006.01) |
| C07D 495/20 | (2006.01) |
| C07D 498/10 | (2006.01) |

(Continued)

(52) U.S. Cl.
CPC ........ H01L 51/0072 (2013.01); C07D 209/96 (2013.01); C07D 333/76 (2013.01); C07D 403/10 (2013.01); C07D 409/04 (2013.01); C07D 471/04 (2013.01); C07D 471/10 (2013.01); C07D 471/14 (2013.01); C07D 471/16 (2013.01); C07D 471/20 (2013.01); C07D 471/22 (2013.01); C07D 487/04 (2013.01); C07D 487/10 (2013.01); C07D 491/147 (2013.01); C07D 491/20 (2013.01); C07D 495/14 (2013.01); C07D 495/20 (2013.01); C07D 498/04 (2013.01); C07D 498/10 (2013.01); C07D 513/04 (2013.01); C07D 513/10 (2013.01); C07D 519/00 (2013.01); C09K 11/025 (2013.01); C09K 11/06 (2013.01); H01L 51/0061 (2013.01); H01L 51/0067 (2013.01); H01L 51/0071 (2013.01); H01L 51/0073 (2013.01); C09K 2211/1011 (2013.01); C09K 2211/1029 (2013.01); C09K 2211/185 (2013.01); H01L 51/5012 (2013.01)

(58) Field of Classification Search
CPC .... C07D 19/00; C07D 209/96; C07D 513/10; C07D 498/10; C07D 495/20; C07D 471/10; C07D 403/10; C07D 513/04; C07D 491/147; C07D 409/04; C07D 471/16; C07D 495/14; C07D 498/04; C07D 487/04; C07D 333/76; C07D 471/14; C07D 487/10; C07D 471/04; C07D 471/20; C07D 471/22; C07D 491/20; C07D 519/00; H01L 51/0067; H01L 51/0061; H01L 51/0072; H01L 51/5012; H01L 51/0071; H01L 51/00; H01L 51/0073; C09K 11/06; C09K 2211/1011; C09K 11/025; C09K 2211/1029; C09K 2211/185
USPC .............................................. 252/500, 301.16
See application file for complete search history.

(56) References Cited

U.S. PATENT DOCUMENTS 7,550,207 B2    6/2009 Sohn et al.
8,852,756 B2    10/2014 Vestweber et al.
(Continued)

FOREIGN PATENT DOCUMENTS

CN    1800298 A    7/2006
CN    101228250 A    7/2008
(Continued)

OTHER PUBLICATIONS

International Search Report for PCT/EP2015/000147 dated Apr. 15, 2015.
CAS reg. No. 1807860-26-9, Sep. 22, 2015. (Year: 2015).

Primary Examiner — Douglas J McGinty
(74) Attorney, Agent, or Firm — Faegre Drinker Biddle & Reath LLP

(57) ABSTRACT

The invention relates to compounds which are suitable for use in electronic devices, and electronic devices, in particular organic electroluminescent devices, containing said compounds.

19 Claims, No Drawings

(51) Int. Cl.
*C07D 513/10* (2006.01)
*C09K 11/02* (2006.01)
*H01L 51/50* (2006.01)

(56) References Cited

U.S. PATENT DOCUMENTS

| | | | |
|---|---|---|---|
| 9,126,970 B2 | 9/2015 | Pflumm et al. | |
| 9,139,582 B2* | 9/2015 | Parham | C07D 513/04 |
| 9,337,430 B2 | 5/2016 | Parham et al. | |
| 9,461,249 B2 | 10/2016 | Vestweber et al. | |
| 9,738,826 B2 | 8/2017 | Pan et al. | |
| 9,882,142 B2* | 1/2018 | Mujica-Fernaud | C07D 219/02 |
| 9,917,272 B2 | 3/2018 | Voges et al. | |
| 9,978,949 B2* | 5/2018 | Mujica-Fernaud | C08G 73/0273 |
| 10,227,528 B2* | 3/2019 | Jatsch | C07D 487/10 |
| 10,298,158 B2* | 5/2019 | Hibino | H02P 6/12 |
| 10,777,750 B2* | 9/2020 | Parham | C07F 9/65517 |
| 2012/0132898 A1 | 5/2012 | Pan et al. | |
| 2012/0142855 A1* | 6/2012 | Scheurich | C07C 25/22 524/609 |
| 2013/0053555 A1* | 2/2013 | Parham | C09B 17/00 544/31 |
| 2013/0063023 A1 | 3/2013 | Pan et al. | |
| 2013/0299743 A1 | 11/2013 | Pan et al. | |
| 2014/0014885 A1 | 1/2014 | Pan et al. | |
| 2014/0203216 A1 | 7/2014 | Parham et al. | |
| 2014/0225046 A1 | 8/2014 | Jatsch et al. | |
| 2015/0129861 A1 | 5/2015 | Hamano et al. | |
| 2016/0308147 A1* | 10/2016 | Parham | C07D 409/04 |
| 2017/0373267 A1 | 12/2017 | Kim et al. | |
| 2018/0138439 A1 | 5/2018 | Voges et al. | |
| 2020/0277284 A1* | 9/2020 | Linge | H01L 51/0073 |
| 2020/0291291 A1* | 9/2020 | Parham | H01L 51/0068 |

FOREIGN PATENT DOCUMENTS

| | | | | |
|---|---|---|---|---|
| CN | 102229565 A | 11/2011 | | |
| CN | 102869662 A | 1/2013 | | |
| DE | 102010019306 A1 | 11/2011 | | |
| JP | 2008545630 A | 12/2008 | | |
| JP | 2012528088 A | 11/2012 | | |
| JP | 2013531617 A | 8/2013 | | |
| KR | 20110068330 A | 6/2011 | | |
| KR | 101247626 B1 | 3/2013 | | |
| KR | 20130135040 A | 12/2013 | | |
| WO | WO-2006122630 A1 | 11/2006 | | |
| WO | WO-2007043354 A1 | 4/2007 | | |
| WO | WO-2011137951 A1 * | 11/2011 | | C07D 471/14 |
| WO | WO-2012008557 A1 | 1/2012 | | |
| WO | WO-2013064206 A1 | 5/2013 | | |
| WO | WO-2014017042 A1 | 1/2014 | | |

* cited by examiner

MATERIALS FOR ORGANIC LIGHT-EMITTING DEVICES

CROSS-REFERENCE TO RELATED APPLICATIONS

This application is a continuation application of U.S. patent application Ser. No. 15/112,108 filed Aug. 24, 2016, which is a national stage application (under 35 U.S.C. § 371) of PCT/EP2015/000147, filed Jan. 27, 2015, which claims benefit of European Application No. 14000729.5, filed Feb. 28, 2014, both of which are incorporated herein by reference in their entirety.

The present invention relates to materials for use in electronic devices, especially as host material for phosphorescent emitters in organic electroluminescent devices, and to electronic devices, especially organic electroluminescent devices, comprising these materials.

BACKGROUND OF THE INVENTION

Emitting materials used in organic electroluminescent devices (OLEDs) are increasingly organometallic complexes which exhibit phosphorescence rather than fluorescence, especially iridium or platinum complexes. For quantum-mechanical reasons, up to four times the energy efficiency and power efficiency is possible using phosphorescent organometallic compounds as phosphorescent emitters. In general terms, however, there is still a need for improvement in OLEDs, especially also in OLEDs which exhibit triplet emission (phosphorescence), for example with regard to efficiency, operating voltage and lifetime.

The properties of phosphorescent OLEDs are not just determined by the triplet emitters used. Also of particular significance here are especially the other materials used, such as matrix materials, hole blocker materials, electron transport materials, hole transport materials and electron or exciton blocker materials. Improvements to these materials can thus also lead to distinct improvements in the OLED properties. For fluorescent OLEDs too, there is still a need for improvement in these materials.

According to the prior art, lactams, for example according to WO 2011/137951 or WO 2013/064206, are one kind of matrix materials used for phosphorescent emitters. However, there is still a need for improvement in the case of use of these matrix materials, and likewise of other matrix materials, especially in relation to the efficiency and lifetime of the device.

BRIEF SUMMARY OF THE INVENTION

It is an object of the present invention to provide compounds suitable for use in a fluorescent or, more particularly, in a phosphorescent OLED, for example as matrix material or as electron transport or hole blocker material, according to the exact substitution pattern. More particularly, it is an object of the present invention to provide matrix materials suitable for green-, yellow- and red-phosphorescing OLEDs.

It has been found that, surprisingly, this object is achieved by the compounds described in detail below, and these lead to distinct improvements in the organic electroluminescent device, especially with regard to lifetime, efficiency and operating voltage. This is especially true of red-, yellow- and green-phosphorescing electroluminescent devices, particularly when the compounds are used as matrix material. The materials additionally feature high thermal stability. The present invention therefore provides these compounds and electronic devices, especially organic electroluminescent devices, comprising these compounds.

DETAILED DESCRIPTION OF THE INVENTION

The present invention provides a compound of the following formula (1)

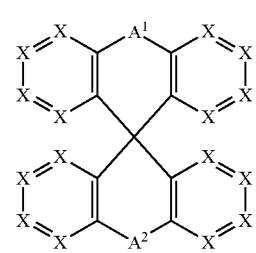

Formula (1)

where the symbols used are as follows:
X is the same or different at each instance and is CR or N or two adjacent X groups together are O, S or NR, so as to give a five-membered ring, or two adjacent X groups together are a group of the formula (2), (3) or (4) with the proviso that the compound of the formula (1) contains at least one group of the formula (2)

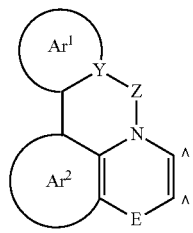

Formula (2)

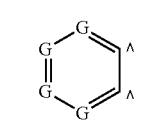

Formula (3)

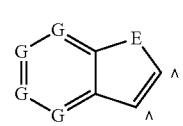

Formula (4)

where ^ identifies the corresponding adjacent X groups in formula (1), i.e. the group of the formula (2) or (3) or (4) is fused to the compound of the formula (1) at these positions;

$A^1, A^2$ is the same or different at each instance and is a single bond, $CR_2$, NR, O, S or C=O;

Z is the same or different at each instance and is C=O, C=S, $CR_2$, BR, $SiR_2$, P(=O)R, SO or $SO_2$:

Y is C when $Ar^1$ is a 6-membered aryl or heteroaryl group, or is C or N when $Ar^1$ is a 5-membered heteroaryl group:

E is the same or different at each instance and is a single bond, $CR_2$, NR, O, S or C=O, with the proviso that E in formula (4) is not a single bond;

$Ar^1$ is the same or different at each instance and, together with the Y group and the carbon atom shown explicitly, is an aromatic or heteroaromatic ring system which has 5 to 24 aromatic ring atoms and may be substituted by one or more R radicals;

Ar² is the same or different at each instance and, together with the three carbon atoms shown explicitly, is an aromatic or heteroaromatic ring system which has 5 to 24 aromatic ring atoms and may be substituted by one or more R radicals;

G is the same or different at each instance and is CR or N:

R is the same or different at each instance and is selected from the group consisting of H, D, F, Cl, Br, I, CN, $NO_2$, $N(Ar^3)_2$, $N(R^1)_2$, $C(=O)Ar^3$, $C(=O)R^1$, $P(=O)(Ar^3)_2$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, each of which may be substituted by one or more $R^1$ radicals, where one or more nonadjacent $CH_2$ groups may be replaced by $R^1C=CR^1$, C≡C, $Si(R^1)_2$, C=O, C=NR¹, $P(=O)(R^1)$, SO, $SO_2$, NR¹, O, S or CONR¹ and where one or more hydrogen atoms may be replaced by D, F, Cl, Br, I, CN or $NO_2$, an aromatic or heteroaromatic ring system which has 5 to 40 aromatic ring atoms and may be substituted in each case by one or more $R^1$ radicals, an aryloxy or heteroaryloxy group which has 5 to 40 aromatic ring atoms and may be substituted by one or more $R^1$ radicals, or an aralkyl or heteroaralkyl group which has 5 to 40 aromatic ring atoms and may be substituted by one or more $R^1$ radicals, where it is optionally possible for two or more adjacent R substituents to form a monocyclic or polycyclic, aliphatic, aromatic or heteroaromatic ring system which may be substituted by one or more $R^1$ radicals;

Ar³ is the same or different at each instance and is an aromatic or heteroaromatic ring system which has 5-30 aromatic ring atoms and may be substituted by one or more nonaromatic $R^1$ radicals; at the same time, two Ar³ radicals bonded to the same nitrogen atom or phosphorus atom may also be bridged to one another by a single bond or a bridge selected from $N(R^1)$, $C(R^1)_2$ and O;

R¹ is the same or different at each instance and is selected from the group consisting of H, D, F, Cl, Br, I, CN, $NO_2$, $N(R^2)_2$, $C(=O)R^2$, $P(=O)(R^2)_2$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, each of which may be substituted by one or more $R^2$ radicals, where one or more nonadjacent $CH_2$ groups may be replaced by $R^2C=CR^2$, C≡C, $Si(R^2)_2$, C=O, C=NR². $P(=O)(R^2)$, SO, $SO_2$, NR², O, S or CONR² and where one or more hydrogen atoms may be replaced by D, F, Cl, Br, I, CN or $NO_2$, an aromatic or heteroaromatic ring system which has 5 to 40 aromatic ring atoms and may be substituted in each case by one or more $R^2$ radicals, an aryloxy or heteroaryloxy group which has 5 to 40 aromatic ring atoms and may be substituted by one or more $R^2$ radicals, or an aralkyl or heteroaralkyl group which has 5 to 40 aromatic ring atoms and may be substituted by one or more $R^2$ radicals, where it is optionally possible for two or more adjacent $R^1$ substituents to form a monocyclic or polycyclic, aliphatic, aromatic or heteroaromatic ring system which may be substituted by one or more $R^2$ radicals;

R² is selected from the group consisting of H, D, F, CN, an aliphatic hydrocarbyl radical having 1 to 20 carbon atoms, an aromatic or heteroaromatic ring system having 5 to 30 aromatic ring atoms, where two or more adjacent $R^2$ substituents together may form a mono- or polycyclic, aliphatic, aromatic or heteroaromatic ring system.

Adjacent X groups in the context of the present invention are X groups bonded directly to one another. Adjacent substituents in the context of the present invention are substituents bonded to atoms that are in turn bonded directly to one another, or bonded to the same atom.

An aryl group in the context of this invention contains 6 to 60 carbon atoms; a heteroaryl group in the context of this invention contains 2 to 60 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatic systems joined to one another by a single bond, for example biphenyl, by contrast, are not referred to as an aryl or heteroaryl group but as an aromatic ring system.

An aromatic ring system in the context of this invention contains 6 to 80 carbon atoms in the ring system. A heteroaromatic ring system in the context of this invention contains 2 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a nonaromatic unit, for example a carbon, nitrogen or oxygen atom. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group.

In the context of the present invention, an aliphatic hydrocarbyl radical or an alkyl group or an alkenyl or alkynyl group which may contain 1 to 40 carbon atoms and in which individual hydrogen atoms or $CH_2$ groups may also be replaced by the abovementioned groups are preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more nonadjacent $CH_2$ groups may be replaced by the abovementioned groups; in addition, it is also possible for one or more hydrogen atoms to be replaced by D, F, Cl, Br, I, CN or $NO_2$, preferably F, Cl or CN, further preferably F or CN, especially preferably CN.

An aromatic or heteroaromatic ring system which has 5-80 aromatic ring atoms and may also be substituted in each case by the abovementioned $R^1$ radicals or a hydrocarbyl radical and which may be joined to the aromatic or heteroaromatic system via any desired positions is especially understood to mean groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from a combination of these systems.

Each cycle having X groups in the structure of the formula (1) is a five- or six-membered ring, where ring formation between the R radicals can also give rise to fused structures. Even when adjacent X groups are a group of the formula (2), (3) or (4), larger fused structures arise. This means that not more than one X—X moiety per cycle is O, S or NR. It is preferable here when the group of the formula (2) is bonded within a six-membered ring. It is further preferable when each cycle contains not more than one group of the formula (2), (3) or (4). Thus, when a cycle in formula (1) contains a group of the formula (2), it is preferable when the other X groups in this cycle are the same or different and are each CR or N, especially CR.

It is further preferable when not more than one X group per cycle is N. More preferably, no X group is N, meaning that all the X groups that are not a group of the formula (2), (3) or (4) or O, S or NR are more preferably CR.

When groups of the formula (3) or (4) are present, it is preferable when not more than one G group in these formulae is N. More preferably, all the G groups in the groups of the formula (3) and (4) are CR.

There follows a schematic illustration of what is meant by the term "cycle" or "cycle having the X groups" in formula (1) and in the definition of X:

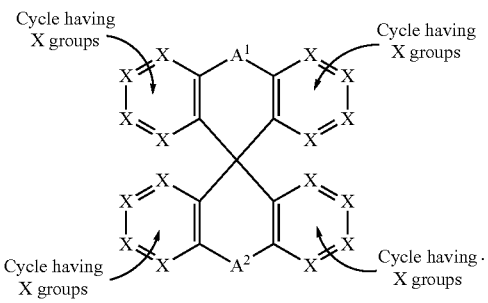

In a preferred embodiment of the invention, at least one of the $A^1$ and $A^2$ groups is a single bond. In this case, it is preferable when a group of the formula (2) is bonded to the same half of the spiro compound on which this $A^1$ or $A^2$ group which is a single bond is also present. In a particularly preferred embodiment of the invention, $A^1$ and $A^2$ are a single bond.

According to the invention, in at least one of the cycles, two adjacent X groups are a group of the formula (2). In a preferred embodiment of the invention, the compound of the formula (1) contains one or two groups of the formula (2), more preferably exactly one group of the formula (2).

It is possible here for the groups of the formula (2) to be bonded in any position and in any orientation. Suitable embodiments of the formula (1) having exactly one group of the formula (2) are therefore the compounds of the formula (5) to (10)

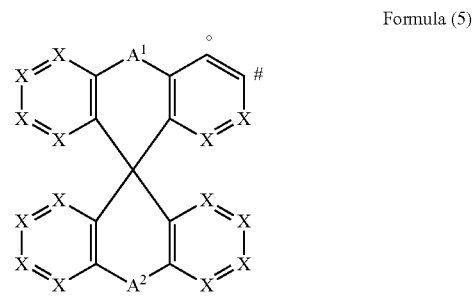

Formula (5)

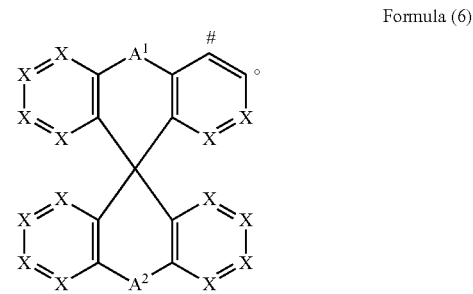

Formula (6)

Formula (7)

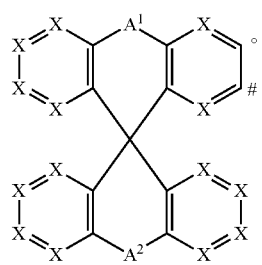

Formula (8)

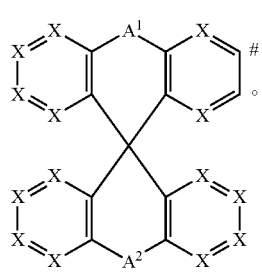

Formula (9)

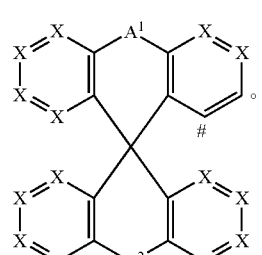

Formula (10)

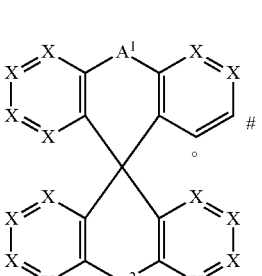

Formula (11)

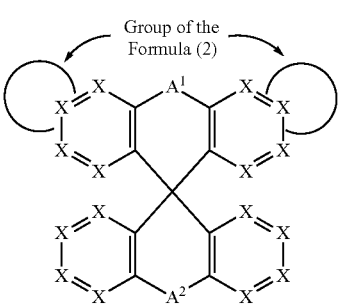

Formula (12)

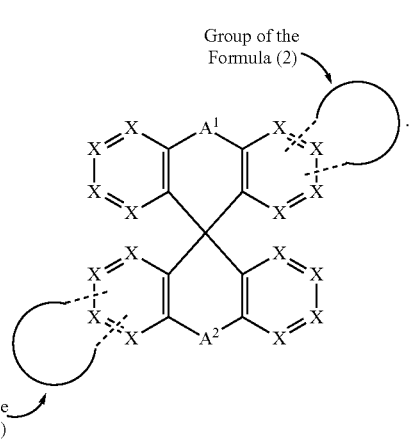

It is possible here for the groups of the formula (2) again to be bonded in all positions and in all possible orientations. A preferred embodiment of compounds having two groups of the formula (2) is the compound of the following formula (12a):

Formula (12a)

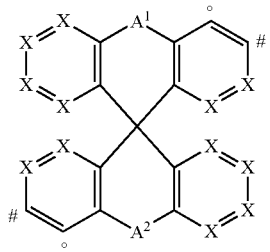

where ° represents the linkage to the nitrogen atom in the group of the formula (2), # represents the linkage to the E group in the group of the formula (2), and the further symbols used are as defined above. In this case, it is preferable that the two X groups in the cycle to which the group of the formula (2) is bonded are CR or N, especially CR.

When the compound of the formula (1) has two groups of the formula (2), these groups may either be bonded to the same half of the spiro compound, as indicated schematically in the following formula (11), or they may be bonded to the two different halves of the spiro compound, as indicated schematically in the following formula (12):

where the symbols used have the definitions given above.

Preference is given to compounds of the formula (5) to (10) in which at least one of the $A^1$ and $A^2$ groups is a single bond. Particular preference is given to compounds in which $A^1$ and $A^2$ are each a single bond.

Preference is further given to compounds of the formula (5) to (10) in which all X groups are the same or different at each instance and are CR.

Very particular preference is given to compounds in which $A^1$ and $A^2$ are each a single bond and in which all X groups are the same or different at each instance and are CR, according to the following formulae (5a) to (10a):

Formula (5a)
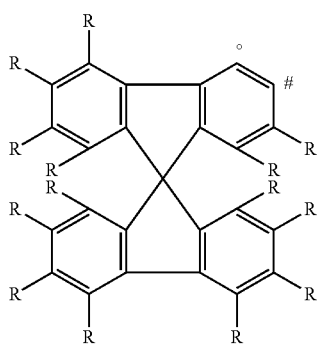
Formula (6a)
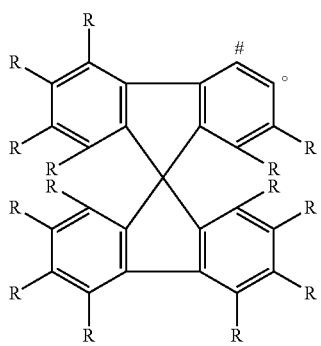
Formula (6a)
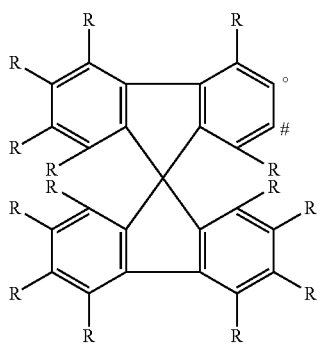
Formula (8a)
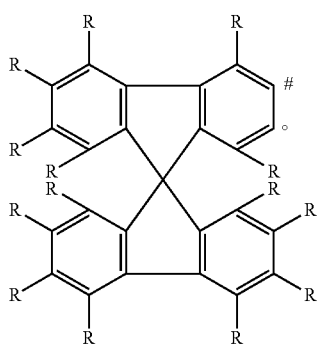
Formula (9a)
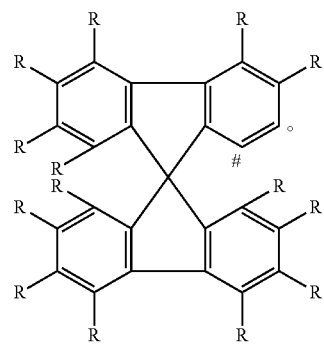
Formula (10a)
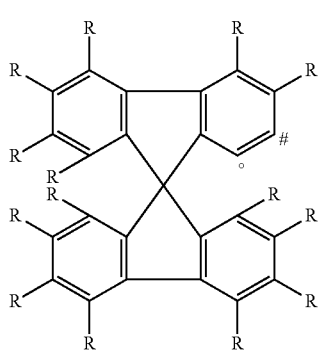
where the symbols used have the definitions given above. Particular preference is given to the structures of the formulae (5a) and (8a).
Preferred compounds of the formulae (5a) to (10a) are the compounds of the formulae (5b) to (10b):
Formula (5b)
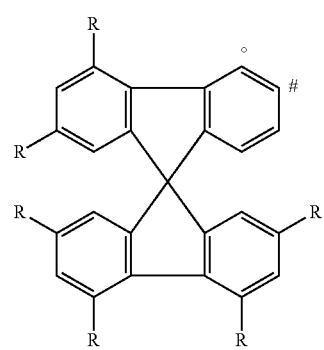
Formula (6b)
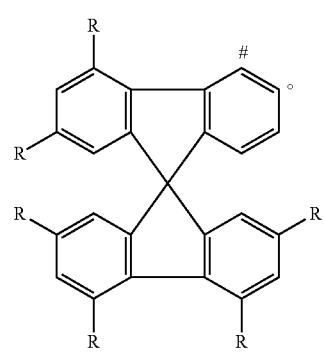

-continued

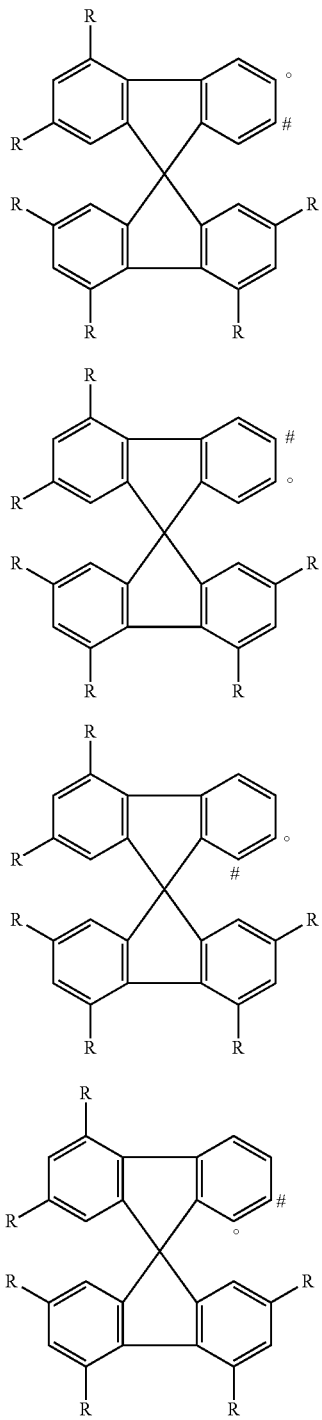

Formula (7b)

Formula (8b)

Formula (9b)

Formula (10b)

where the symbols used have the definitions given above.

There follows a description of the groups of the formula (2).

In a preferred embodiment of the invention, Z is the same or different and is C=O or C=S, more preferably C=O.

In a further preferred embodiment of the invention, E is a single bond, $CR_2$, C=O or NR, more preferably a single bond, $CR_2$ or C=O and most preferably a single bond.

In a further preferred embodiment of the invention, the $Ar^1$ group is a group of the following formula (13), (14), (15), (16) and (17)

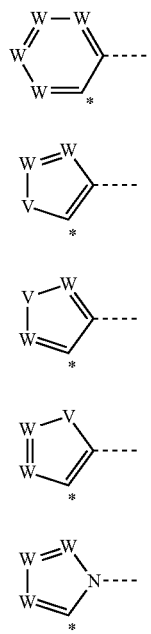

Formula (13)

Formula (14)

Formula (15)

Formula (16)

Formula (17)

where the dotted bond indicates the linkage to Z, * indicates the position of the linkage to $Ar^2$ and, in addition:

W is the same or different at each instance and is CR or N, or two adjacent W groups are a group of the following formula (18) or (19)

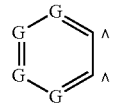

Formula (18)

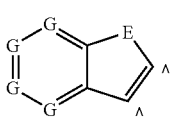

Formula (19)

where E is as defined above, but is preferably not a single bond. G is the same or different at each instance and is CR or N and ^ indicate the corresponding adjacent W groups in the formula (13) to (17);

V is NR, O or S.

In a further preferred embodiment of the invention, the $Ar^2$ group is a group of one of the following formulae (20), (21) and (22)

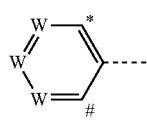

Formula (20)

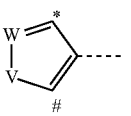

Formula (21)

Formula (22)

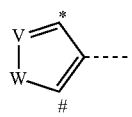

where the dotted bond indicates the linkage to N, # indicates the position of the linkage to E, * indicates the linkage to Ar¹ and W and V are each as defined above.

In a particularly preferred embodiment of the invention, the abovementioned preferences occur simultaneously. Particular preference is therefore given to groups of formula (2) for which:

Z is C=O or C=S;
E is the same or different at each instance and is a single bond, $CR_2$, C=O or NR;
Ar¹ is selected from the groups of the abovementioned formulae (13), (14), (15), (16) and (17);
Ar² is selected from the groups of the abovementioned formulae (20), (21) and (22).

In a very particularly preferred embodiment of the invention, for groups of the formula (2):

Z is C=O;
E is a single bond;
Ar¹ is selected from the groups of the abovementioned formulae (13), (14), (15), (16) and (17):
Ar² is selected from the groups of the abovementioned formulae (20), (21) and (22).

At the same time, the abovementioned preferred Ar¹ and Ar² groups may be combined with one another as desired. Suitable combinations are thus as follows:

| Ar¹ | Ar² |
| --- | --- |
| Formula (13) | Formula (20) |
| Formula (13) | Formula (21) |
| Formula (13) | Formula (22) |
| Formula (14) | Formula (20) |
| Formula (14) | Formula (21) |
| Formula (14) | Formula (22) |
| Formula (15) | Formula (20) |
| Formula (15) | Formula (21) |
| Formula (15) | Formula (22) |
| Formula (16) | Formula (20) |
| Formula (16) | Formula (21) |
| Formula (16) | Formula (22) |
| Formula (17) | Formula (20) |
| Formula (17) | Formula (21) |
| Formula (17) | Formula (22) |

More preferably, at least one of the Ar¹ and Ar² groups is a 6-membered aryl or a 6-membered heteroaryl group. More preferably, both Ar¹ and Ar² groups are a 6-membered aryl or a 6-membered heteroaryl group. More preferably, thus, Ar¹ is a group of the formula (13) and, at the same time, Ar² is a group of the formula (20).

Preferred embodiments of the group of the formula (2) are therefore the compounds of the following formulae (23) to (29):

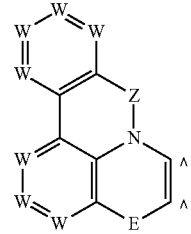
Formula (23)

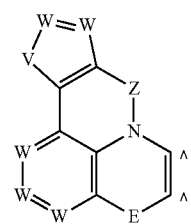
Formula (24)

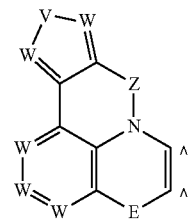
Formula (25)

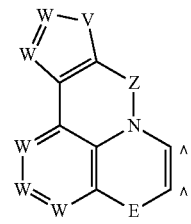
Formula (26)

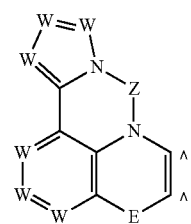
Formula (27)

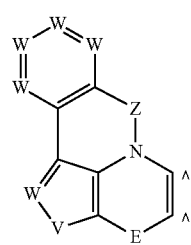
Formula (28)

Formula (29)

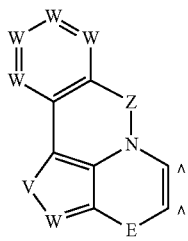

where ^ identifies the position of the linkage in formula (1) and the further symbols used are as defined above.

As already stated above, it is also possible for two adjacent W groups to be a group of the abovementioned formula (18) or (19).

In a further preferred embodiment of the groups of the formulae (13) to (17), (20) to (22) and (23) to (29), not more than one W symbol in total per cycle is N, and the remaining W symbols that are not a group of the formula (18) or (19) are CR. In a particularly preferred embodiment of the invention, all W symbols that are not a group of the formula (18) or (19) are CR. Particularly preferred groups of the formula (2) are therefore the groups of the following formulae (23a) to (29a)

Formula (23a)

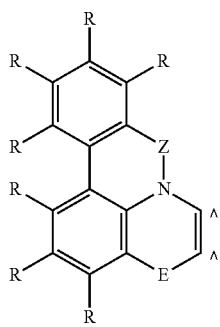

Formula (24a)

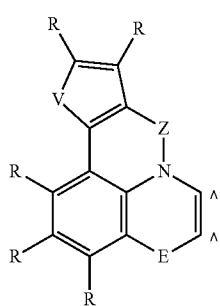

Formula (25a)

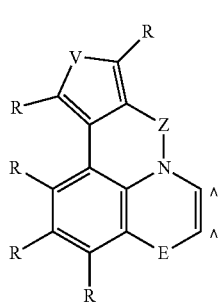

Formula (26a)

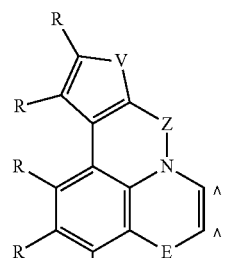

Formula (27a)

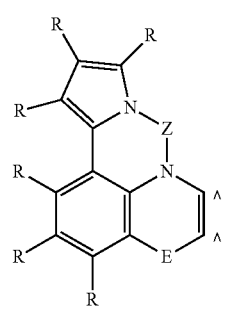

Formula (28a)

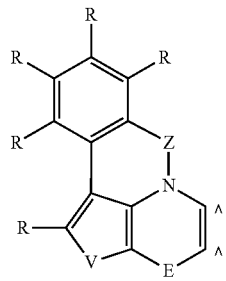

Formula (29a)

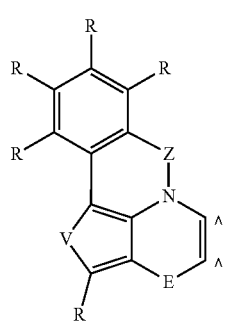

where the symbols used have the definitions given above.

Very particular preference is therefore given to the compounds of the following formulae (23b) to (29b):

Formula (23b)

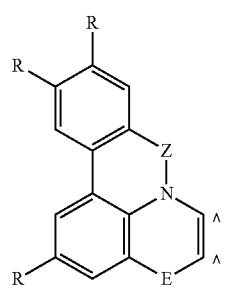

Formula (24b)

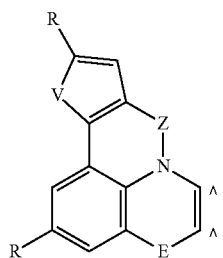

Formula (25b)

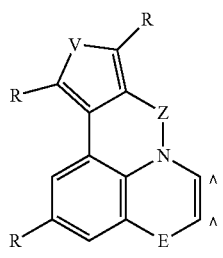

Formula (26b)

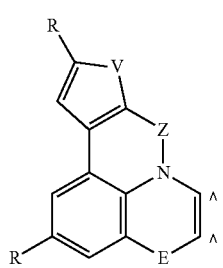

Formula (27b)

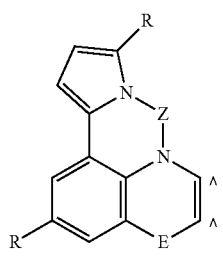

Formula (28b)

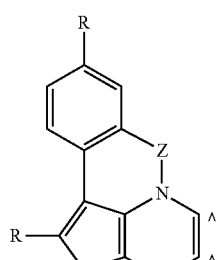

Formula (29b)

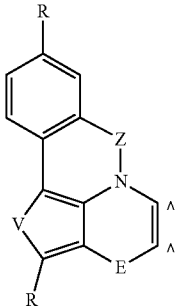

where the symbols used have the definitions given above.

Very particularly preferred groups of the formula (2) are the groups of the formula (23) or (23a) or (23b).

In this case, in the formulae (23) to (29), (23a) to (29a) and (23b) to (29b), Z is preferably C=O.

In addition, in the formulae (23) to (29), (23a) to (29a) and (23b) to (29b), E is preferably a single bond.

More preferably, in the formulae (23) to (29), (23a) to (29a) and (23b) to (29b), Z is C=O and, at the same time, E is a single bond.

It is additionally preferable, if two adjacent W groups are a group of the formula (18) or (19), that not more than one G group is N. More preferably, all G groups are CR. It is additionally preferable, when two adjacent W groups are a group of the formula (19), that E in the group of the formula (19) is $CR_2$, C=O or NR, especially $CR_2$ or NR.

The compounds of the abovementioned formulae (5) to (10) or the preferred embodiments may be combined as desired with the groups of the abovementioned formulae (23) to (29) or the preferred embodiments.

Suitable compounds are therefore the compounds listed in the following table:

| Compound | Group of the formula (2) |
| --- | --- |
| Formula (5) | Formula (23) |
| Formula (5) | Formula (24) |
| Formula (5) | Formula (25) |
| Formula (5) | Formula (26) |
| Formula (5) | Formula (27) |
| Formula (5) | Formula (28) |
| Formula (5) | Formula (29) |
| Formula (6) | Formula (23) |
| Formula (6) | Formula (24) |
| Formula (6) | Formula (25) |
| Formula (6) | Formula (26) |
| Formula (6) | Formula (27) |
| Formula (6) | Formula (28) |
| Formula (6) | Formula (29) |
| Formula (7) | Formula (23) |
| Formula (7) | Formula (24) |
| Formula (7) | Formula (25) |
| Formula (7) | Formula (26) |
| Formula (7) | Formula (27) |
| Formula (7) | Formula (28) |
| Formula (7) | Formula (29) |
| Formula (8) | Formula (23) |
| Formula (8) | Formula (24) |
| Formula (8) | Formula (25) |
| Formula (8) | Formula (26) |
| Formula (8) | Formula (27) |
| Formula (8) | Formula (28) |
| Formula (8) | Formula (29) |
| Formula (9) | Formula (23) |
| Formula (9) | Formula (24) |

| Compound | Group of the formula (2) |
|---|---|
| Formula (9) | Formula (25) |
| Formula (9) | Formula (26) |
| Formula (9) | Formula (27) |
| Formula (9) | Formula (28) |
| Formula (9) | Formula (29) |
| Formula (10) | Formula (23) |
| Formula (10) | Formula (24) |
| Formula (10) | Formula (25) |
| Formula (10) | Formula (26) |
| Formula (10) | Formula (27) |
| Formula (10) | Formula (28) |
| Formula (10) | Formula (29) |

Preferred compounds are the compounds listed in the following table:

| Compound | Group of the formula (2) |
|---|---|
| Formula (5a) | Formula (23a) |
| Formula (5a) | Formula (24a) |
| Formula (5a) | Formula (25a) |
| Formula (5a) | Formula (26a) |
| Formula (5a) | Formula (27a) |
| Formula (5a) | Formula (28a) |
| Formula (5a) | Formula (29a) |
| Formula (6a) | Formula (23a) |
| Formula (6a) | Formula (24a) |
| Formula (6a) | Formula (25a) |
| Formula (6a) | Formula (26a) |
| Formula (6a) | Formula (27a) |
| Formula (6a) | Formula (28a) |
| Formula (6a) | Formula (29a) |
| Formula (7a) | Formula (23a) |
| Formula (7a) | Formula (24a) |
| Formula (7a) | Formula (25a) |
| Formula (7a) | Formula (26a) |
| Formula (7a) | Formula (27a) |
| Formula (7a) | Formula (28a) |
| Formula (7a) | Formula (29a) |
| Formula (8a) | Formula (23a) |
| Formula (8a) | Formula (24a) |
| Formula (8a) | Formula (25a) |
| Formula (8a) | Formula (26a) |
| Formula (8a) | Formula (27a) |
| Formula (8a) | Formula (28a) |
| Formula (8a) | Formula (29a) |
| Formula (9a) | Formula (23a) |
| Formula (9a) | Formula (24a) |
| Formula (9a) | Formula (25a) |
| Formula (9a) | Formula (26a) |
| Formula (9a) | Formula (27a) |
| Formula (9a) | Formula (28a) |
| Formula (9a) | Formula (29a) |
| Formula (10a) | Formula (23a) |
| Formula (10a) | Formula (24a) |
| Formula (10a) | Formula (25a) |
| Formula (10a) | Formula (26a) |
| Formula (10a) | Formula (27a) |
| Formula (10a) | Formula (28a) |
| Formula (10a) | Formula (29a) |

Particularly preferred compounds are the compounds listed in the following table:

| Compound | Group of the formula (2) |
|---|---|
| Formula (5b) | Formula (23b) |
| Formula (5b) | Formula (24b) |
| Formula (5b) | Formula (25b) |
| Formula (5b) | Formula (26b) |
| Formula (5b) | Formula (27b) |
| Formula (5b) | Formula (28b) |
| Formula (5b) | Formula (29b) |
| Formula (6b) | Formula (23b) |
| Formula (6b) | Formula (24b) |
| Formula (6b) | Formula (25b) |
| Formula (6b) | Formula (26b) |
| Formula (6b) | Formula (27b) |
| Formula (6b) | Formula (28b) |
| Formula (6b) | Formula (29b) |
| Formula (7b) | Formula (23b) |
| Formula (7b) | Formula (24b) |
| Formula (7b) | Formula (25b) |
| Formula (7b) | Formula (26b) |
| Formula (7b) | Formula (27b) |
| Formula (7b) | Formula (28b) |
| Formula (7b) | Formula (29b) |
| Formula (8b) | Formula (23b) |
| Formula (8b) | Formula (24b) |
| Formula (8b) | Formula (25b) |
| Formula (8b) | Formula (26b) |
| Formula (8b) | Formula (27b) |
| Formula (8b) | Formula (28b) |
| Formula (8b) | Formula (29b) |
| Formula (9b) | Formula (23b) |
| Formula (9b) | Formula (24b) |
| Formula (9b) | Formula (25b) |
| Formula (9b) | Formula (26b) |
| Formula (9b) | Formula (27b) |
| Formula (9b) | Formula (28b) |
| Formula (9b) | Formula (29b) |
| Formula (10b) | Formula (23b) |
| Formula (10b) | Formula (24b) |
| Formula (10b) | Formula (25b) |
| Formula (10b) | Formula (26b) |
| Formula (10b) | Formula (27b) |
| Formula (10b) | Formula (28b) |
| Formula (10b) | Formula (29b) |

Among these compounds, preference is given to compounds of the formula (5) to (10) which contain a group of the formula (23) as group of the formula (2), particular preference to compounds of the formula (5a) to (10a) which contain a group of the formula (23a) as group of the formula (2), and very particular preference to compounds of the formula (5b) to (10b) which contain a group of the formula (23b) as group of the formula (2).

Very particularly preferred compounds are thus the compounds of the following formulae (5c) to (10c):
Formula (5c)
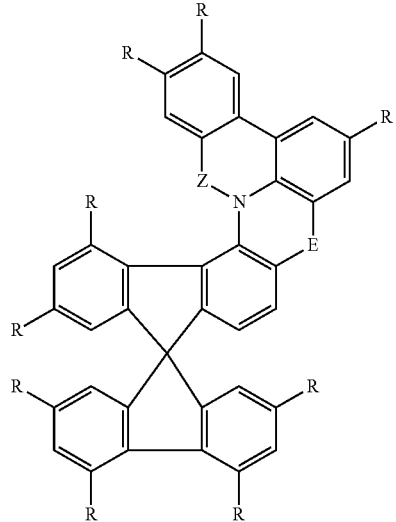
Formula (6c)
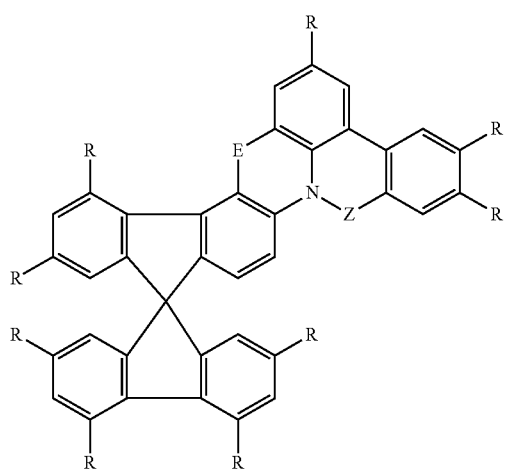
Formula (7c)
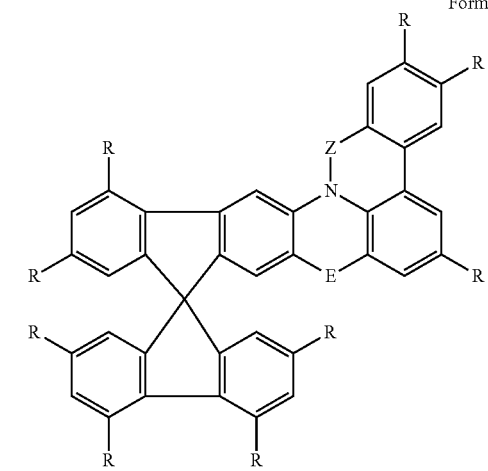
Formula (8c)
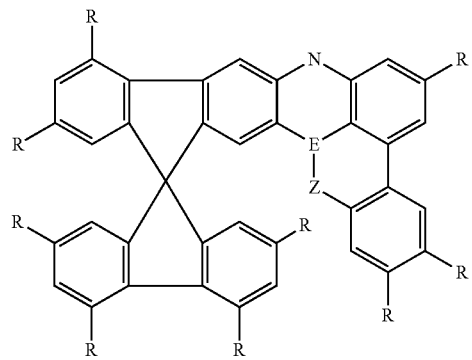
Formula (9c)
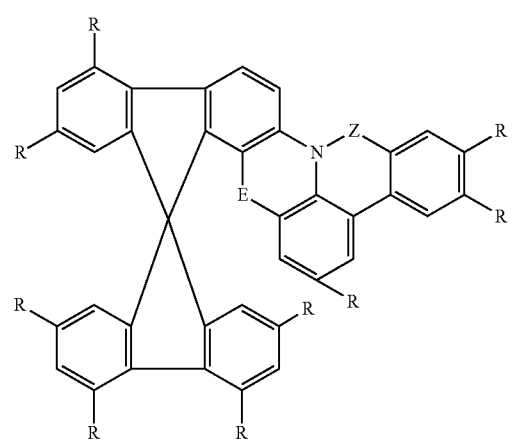
Formula (10c)
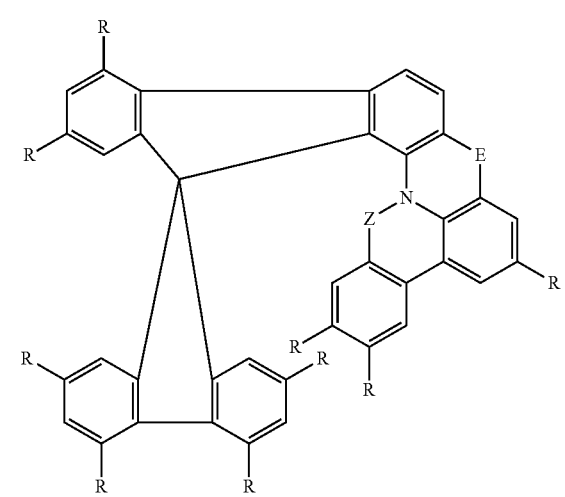
where the symbols used have the definitions given above.

Very particular preference is given to the compounds of the following formulae (5d) and (10d):

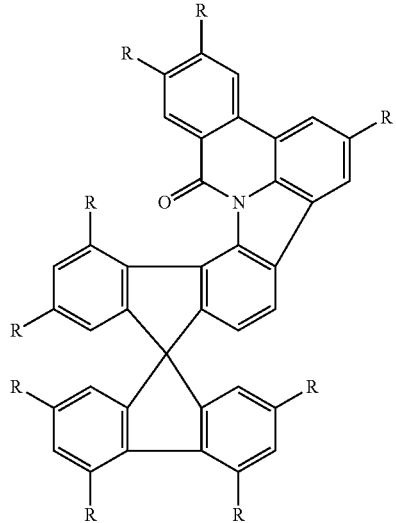
Formula (5d)

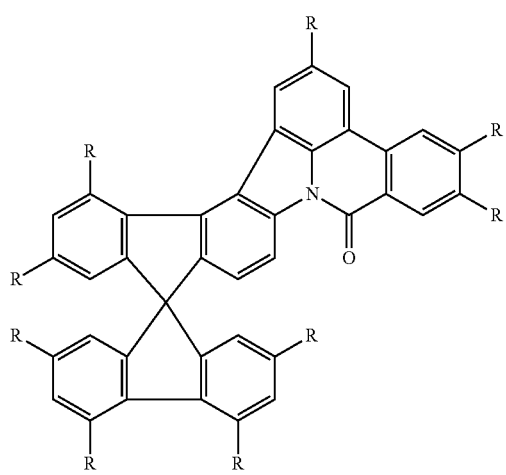
Formula (6d)

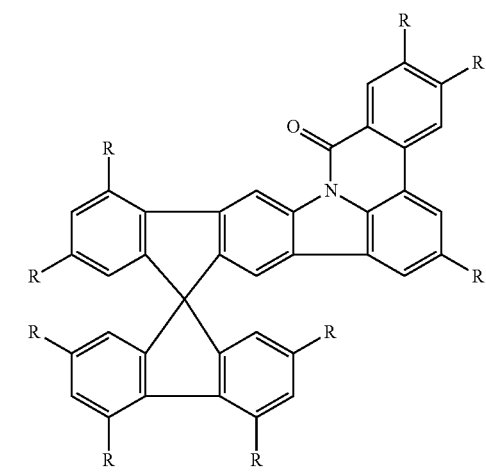
Formula (7d)

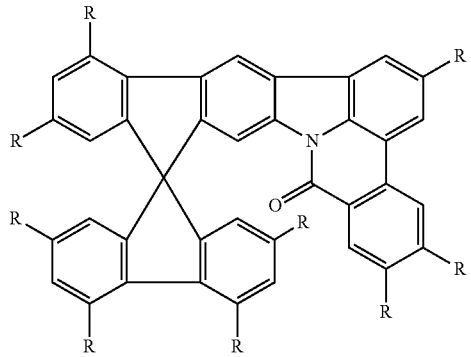
Formula (8d)

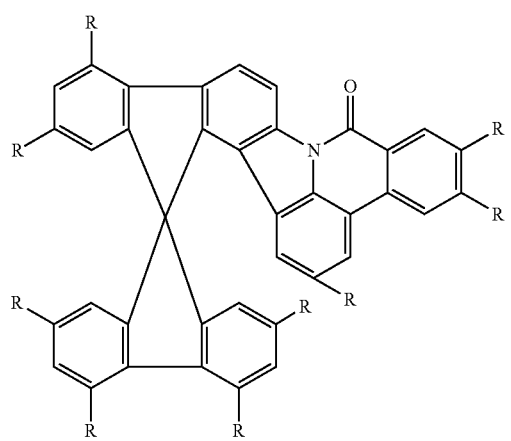
Formula (9d)

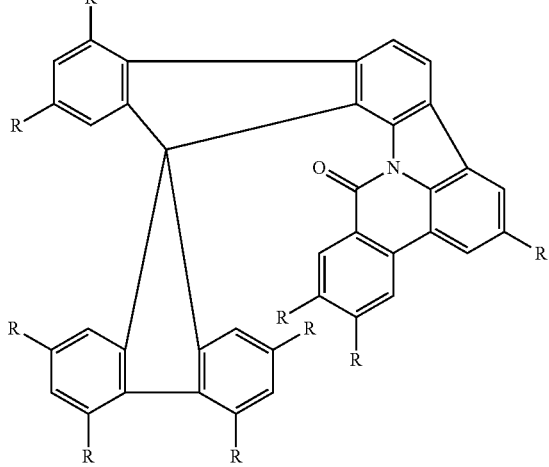
Formula (10d)

where the symbols used have the definitions given above.

In a preferred embodiment of the invention, R in the abovementioned formulae is the same or different at each instance and is selected from the group consisting of H, D, F, Cl, Br, CN, N(Ar$^3$)$_2$, C(=O)Ar$^3$, a straight-chain alkyl or alkoxy group having 1 to 10 carbon atoms or a branched or cyclic alkyl or alkoxy group having 3 to 10 carbon atoms or an alkenyl or alkynyl group having 2 to 10 carbon atoms, each of which may be substituted by one or more R$^1$ radicals, where one or more nonadjacent CH$_2$ groups may be replaced by O and where one or more hydrogen atoms may be replaced by D or F, or an aromatic or heteroaromatic ring system which has 5 to 30 aromatic ring atoms and may be substituted in each case by one or more $R^1$ radicals.

In a particularly preferred embodiment of the invention, R in the abovementioned formulae is the same or different at each instance and is selected from the group consisting of H, D, F, CN, $N(Ar^3)_2$, a straight-chain alkyl group having 1 to 4 carbon atoms or a branched alkyl group having 3 or 4 carbon atoms or a cyclic alkyl group having 5 or 6 carbon atoms, each of which may be substituted by one or more $R^1$ radicals, where one or more hydrogen atoms may be replaced by D or F, or an aromatic or heteroaromatic ring system which has 6 to 24 aromatic ring atoms and may be substituted in each case by one or more $R^1$ radicals.

In a very particularly preferred embodiment of the invention, R in the abovementioned formulae is the same or different at each instance and is selected from the group consisting of H and an aromatic or heteroaromatic ring system which has 6 to 24, preferably 6 to 18, aromatic ring atoms and may be substituted in each case by one or more $R^1$ radicals.

When the compounds of the formula (1) or the preferred embodiments are used as electron transport material, it is preferable when the Z group is C=O and/or when at least one of the R radicals is an aromatic ring system or an electron-deficient heteroaromatic ring system. According to the invention, electron-deficient heteroaromatic groups are five-membered heteroaromatic rings having at least two heteroatoms or six-membered heteroaromatic rings having at least one heteroatom, to each of which may be fused another one or more aromatic or heteroaromatic groups.

When the compounds of the formula (1) or the preferred embodiments are used as matrix material for a phosphorescent emitter, it is preferable when the Z group is C=O and/or when at least one of the R radicals is a substituted or unsubstituted carbazole, indenocarbazole or indolocarbazole, each of which may be bonded via a carbon atom or a nitrogen atom. In addition, it is preferable in this case when the compounds of the invention do not have any aryl or heteroaryl groups in which two or more six-membered aryl or heteroaryl groups are fused directly to one another. More preferably, in this case, the compound of the invention does not contain any aryl or heteroaryl groups having six-membered rings fused directly to one another at all.

In a preferred embodiment of the invention, either all R radicals are H or exactly one or two R radical(s) is/are an aromatic or heteroaromatic ring system which has 6 to 18 aromatic ring atoms and may be substituted in each case by one or more $R^1$ radicals, and the other R radicals are H.

When one or more R radicals are an aromatic or heteroaromatic ring system, preferred R radicals are the same or different at each instance and are selected from the group consisting of phenyl, ortho-, meta- or para-biphenyl, ortho-terphenyl, meta-terphenyl, para-terphenyl or branched terphenyl, ortho-quaterphenyl, meta-quaterphenyl, para-quaterphenyl or branched quaterphenyl, 1-, 2-, 3- or 4-fluorenyl, 1-, 2-, 3- or 4-spirobifluorenyl, 1- or 2-naphthyl, anthracene, phenanthrene, triphenylene, pyrene, benzanthracene, pyrrole, furan, thiophene, indole, benzofuran, benzothiophene, 1-, 2- or 3-carbazole, 1-, 2- or 3-dibenzofuran, 1-, 2- or 3-dibenzothiophene, indenocarbazole, indolocarbazole, pyrazole, imidazole, benzimidazole, pyridine, pyrimidine, pyrazine, pyridazine, triazine or quinoline or combinations of two or three of these groups, each of which may be substituted by one or more $R^1$ radicals.

Preferred aromatic or heteroaromatic ring systems R are selected from the groups of the following formulae R-1 to R-53:

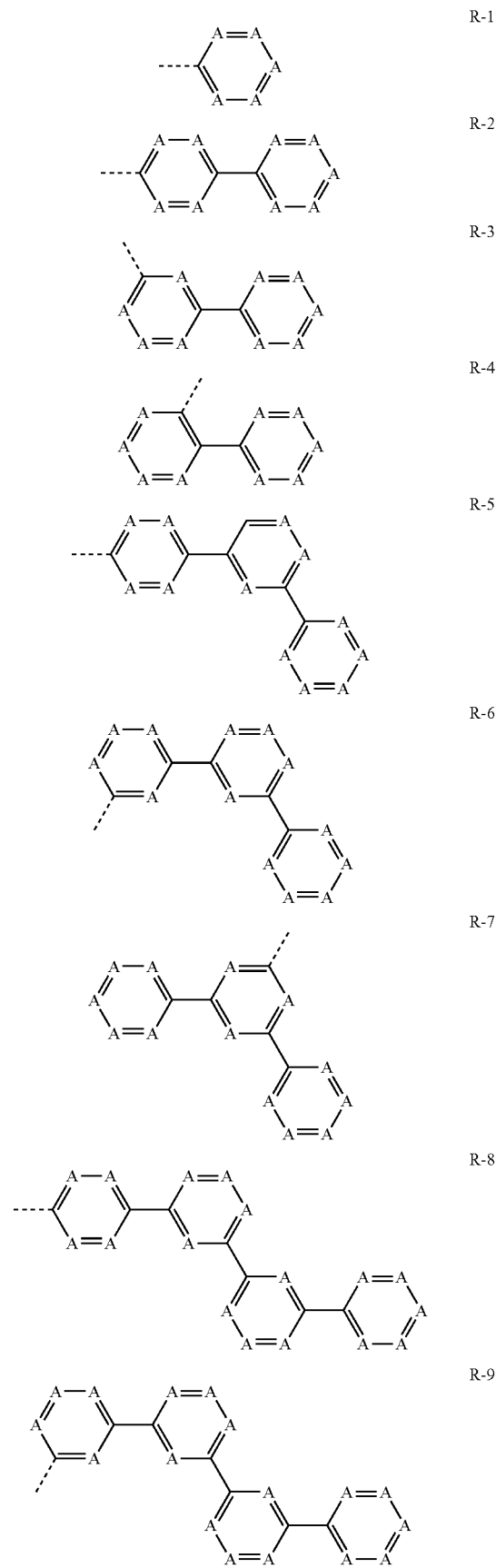

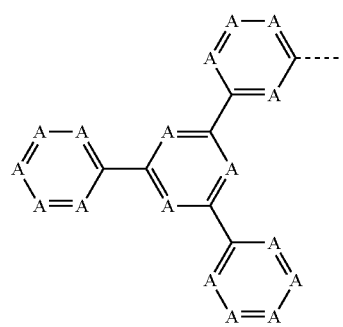 R-10
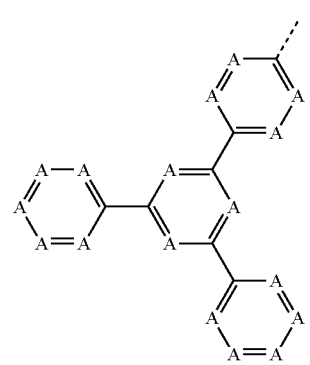 R-11
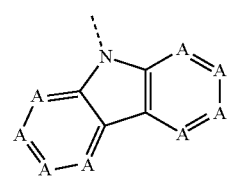 R-12
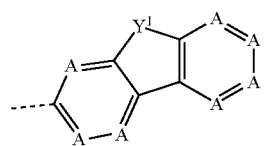 R-13
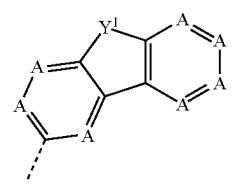 R-14
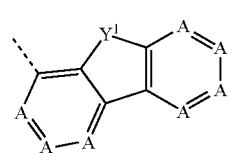 R-15
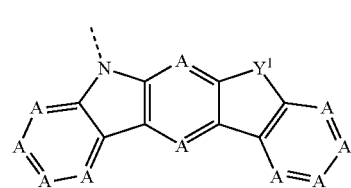 R-16
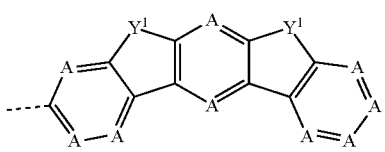 R-17
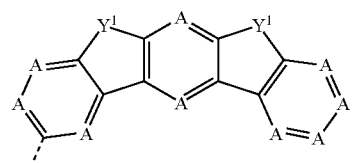 R-18
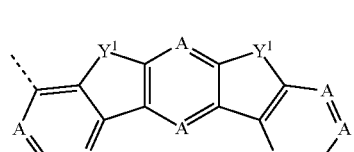 R-19
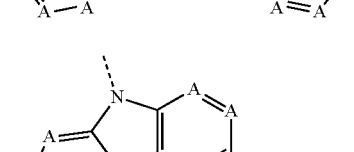 R-20
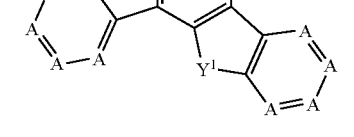 R-21
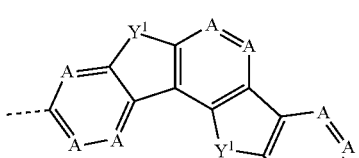 R-22
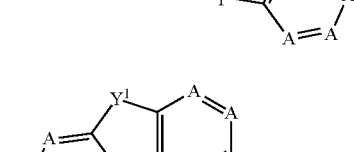 R-23
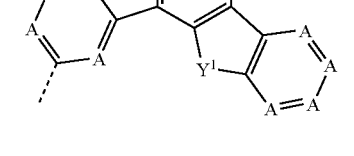 R-24

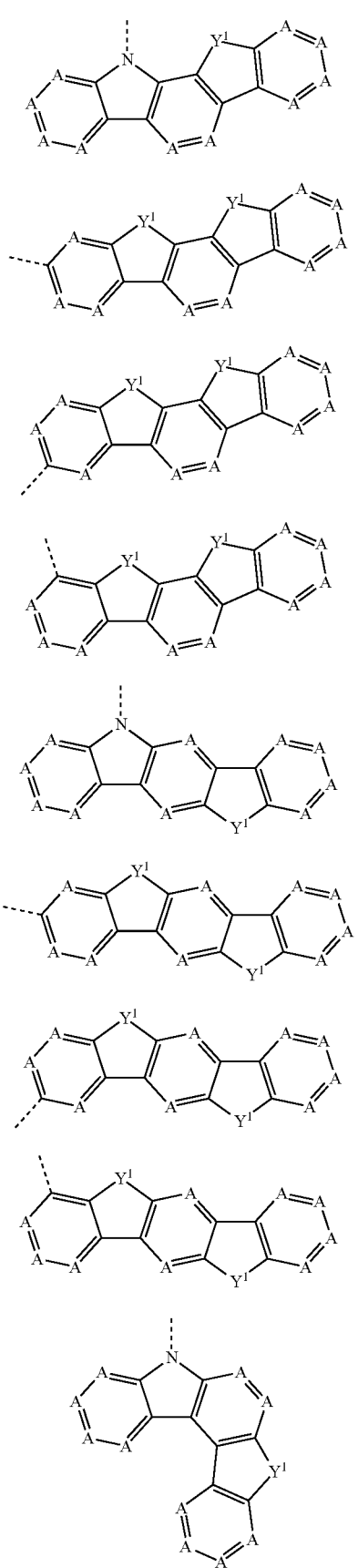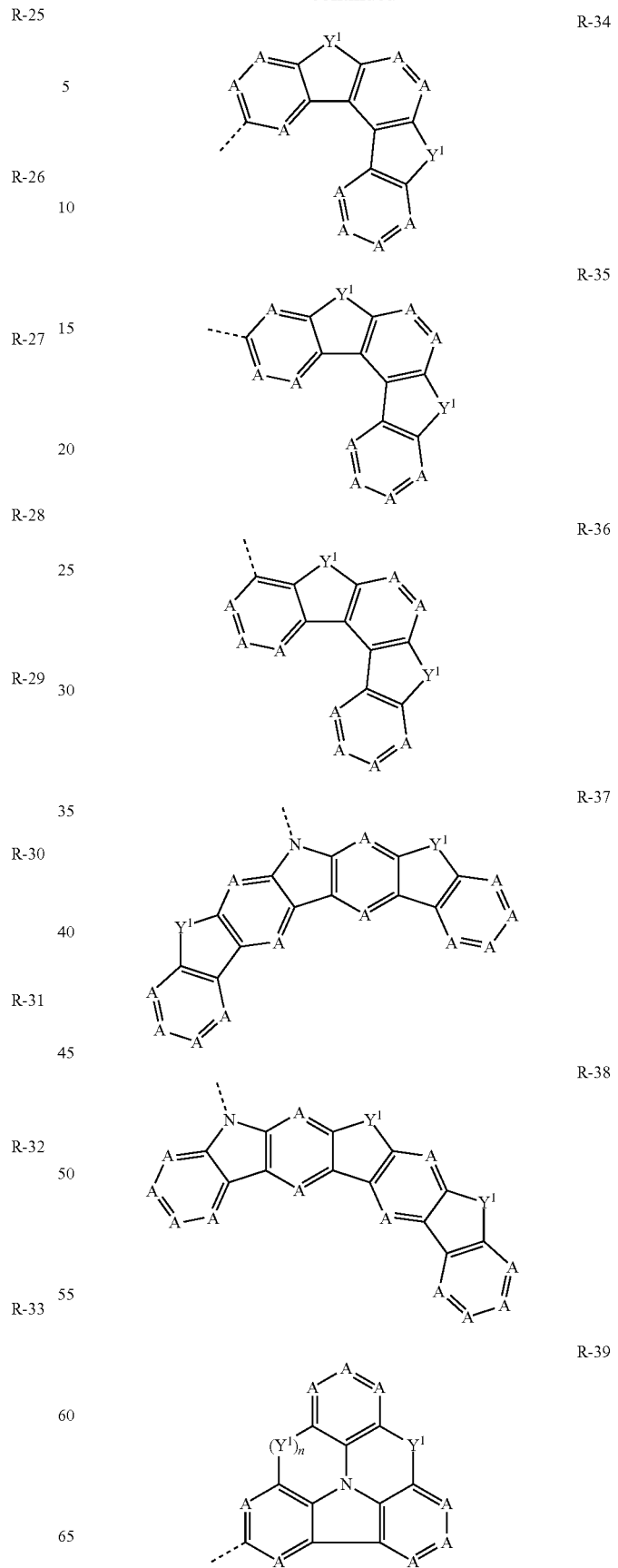

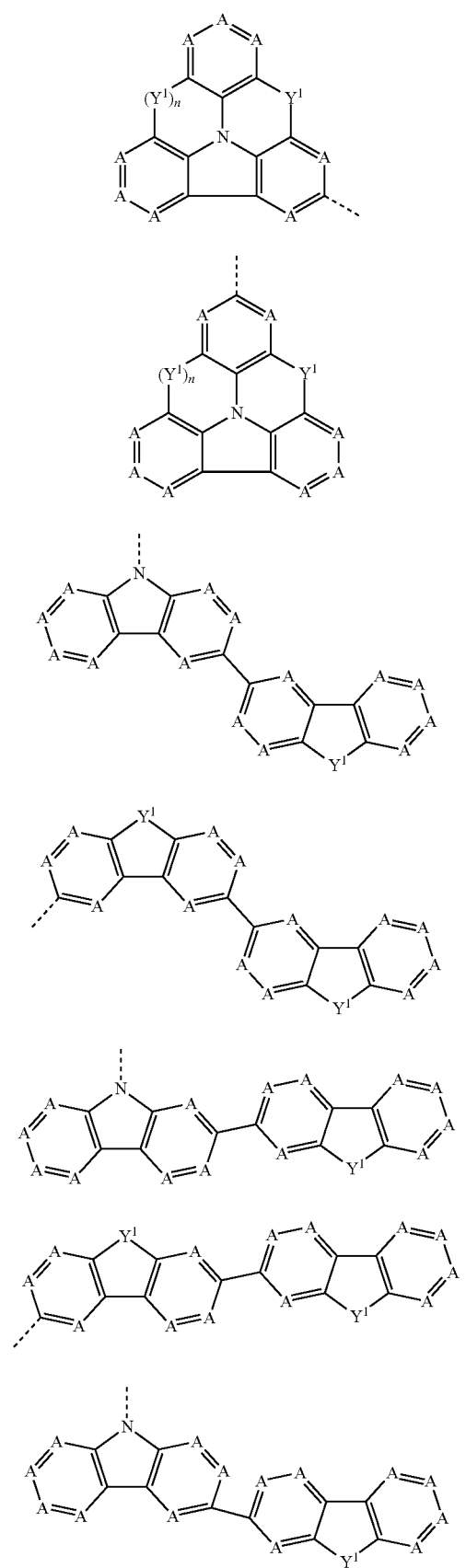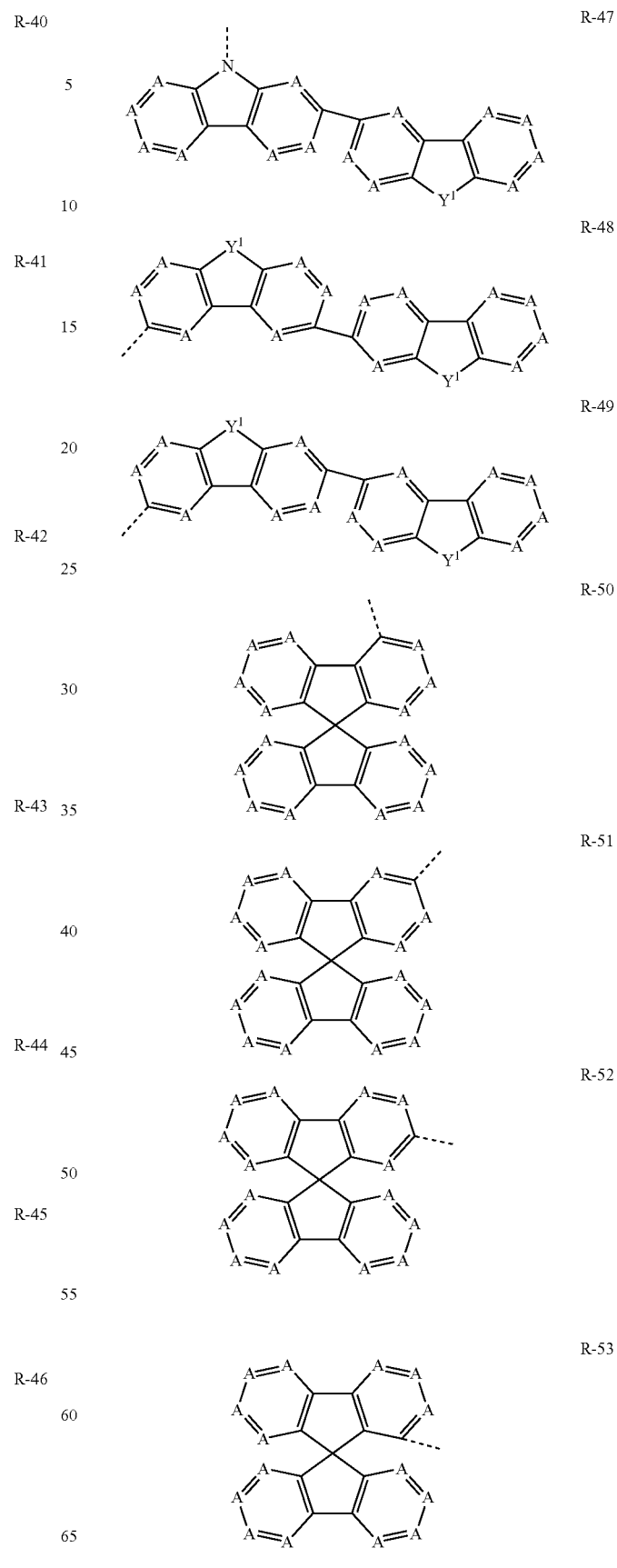

where $R^1$ is as defined above, the dotted bond represents the bond to the group of the formula (1) and, in addition:

A is the same or different at each instance and is $CR^1$ or N, where not more than 3 X symbols per cycle are N;

$Y^1$ is the same or different at each instance and is $C(R^1)_2$, $NR^1$, O or S;

n is 0 or 1, where n=0 means that no $Y^1$ group is bonded at this position and $R^1$ radicals thereof are bonded to the corresponding carbon atoms instead.

The expression "per cycle" mentioned above and also used hereinafter relates in the context of the present application to each individual ring present in the compound, i.e. to each individual 5- or 6-membered ring.

In a preferred embodiment of the R-1 group, no, one, two or three A symbols are N. Particular preference is given to phenyl of the formula R-1a, pyrimidine of the formula R-1b or triazine of the formula R-1c

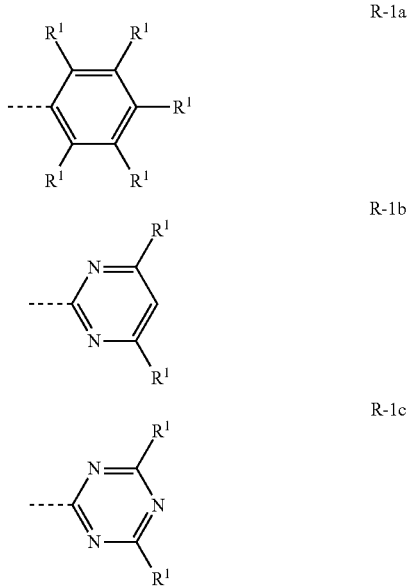

where $R^1$ is as defined above and, in formula R-1a, is especially H or an aromatic or heteroaromatic ring system which has 6 to 18 aromatic ring atoms and may be substituted by one or more $R^2$ radicals, and, in formula R-1b and R-1c, is in each case especially an aromatic or heteroaromatic ring system which has 6 to 18 aromatic ring atoms and may be substituted by one or more $R^1$ radicals.

In preferred groups of the abovementioned formulae R-2 to R-53, not more than one A symbol per cycle is N. More preferably, the symbol A is the same or different at each instance and is $CR^1$, especially CH.

When the abovementioned groups for R-1 to R-53 have two or more $Y^1$ groups, possible options for these include all combinations from the definition of $Y^1$. Preference is given to groups in which one $Y^1$ group is $NR^1$ and the other $Y^1$ group is $C(R^1)_2$ or in which both $Y^1$ groups are $NR^1$ or in which both $Y^1$ groups are O.

In a further preferred embodiment of the invention, at least one $Y^1$ group is $C(R^1)_2$ or $NR^1$.

When $Y^1$ is $NR^1$, the substituent $R^1$ bonded to the nitrogen atom is preferably an aromatic or heteroaromatic ring system which has 5 to 24 aromatic ring atoms and may also be substituted by one or more $R^2$ radicals. In a particularly preferred embodiment, this substituent $R^1$ is the same or different at each instance and is an aromatic or heteroaromatic ring system which has 6 to 24 aromatic ring atoms, which does not have any fused aryl groups and which does not have any fused heteroaryl groups in which two or more aromatic or heteroaromatic 6-membered ring groups are fused directly to one another, and which may also be substituted in each case by one or more $R^2$ radicals. Particular preference is given to phenyl, biphenyl, terphenyl and quaterphenyl.

When $Y^1$ is $C(R^1)_2$, $R^1$ is preferably the same or different at each instance and is a linear alkyl group having 1 to 10 carbon atoms, preferably 1 to 4 carbon atoms, or a branched alkyl group having 3 to 10 carbon atoms, preferably 3 or 4 carbon atoms, or an aromatic or heteroaromatic ring system having 5 to 24 aromatic ring atoms, preferably 6 to 18 aromatic ring atoms, which may also be substituted by one or more $R^2$ radicals. Most preferably, $R^1$ is a methyl group or a phenyl group. In this case, the $R^1$ radicals together may also form a ring system, which leads to a spiro system.

In a further preferred embodiment of the invention. R is a triarylamine group which may be substituted by one or more $R^1$ radicals. The latter is preferably selected from the structures of the following formula R-54:

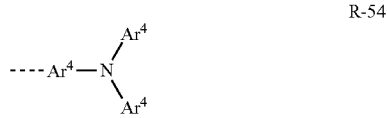

where the dotted bond indicates the linkage to the base skeleton and $Ar^4$ is the same or different at each instance and is an aromatic or heteroaromatic ring system which has 5 to 18 aromatic ring atoms in each case, preferably 6 to 12 aromatic ring atoms in each case, and may be substituted in each case by one or more $R^1$ radicals.

At the same time, in compounds which are processed by vacuum evaporation, the alkyl groups preferably have not more than five carbon atoms, more preferably not more than 4 carbon atoms, most preferably not more than 1 carbon atom. For compounds which are processed from solution, suitable compounds are also those substituted by alkyl groups, especially branched alkyl groups, having up to 10 carbon atoms or those substituted by oligoarylene groups, for example ortho-, meta-, para- or branched terphenyl or quaterphenyl groups.

The abovementioned preferred embodiments may be combined with one another as desired. In a particularly preferred embodiment of the invention, the abovementioned preferences occur simultaneously.

Examples of preferred compounds according to the above-detailed embodiments are the compounds of the following structures:
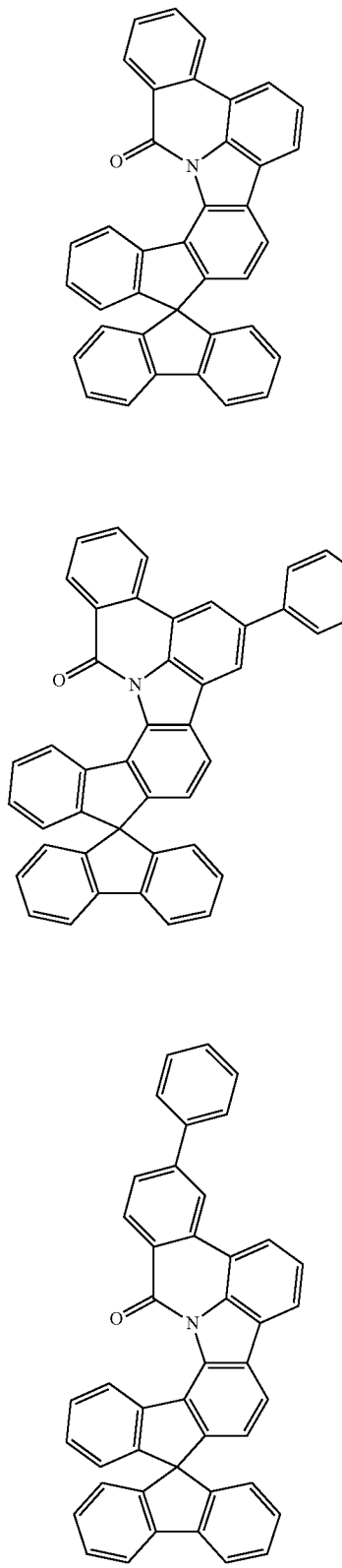
(1)
(2)
(3)
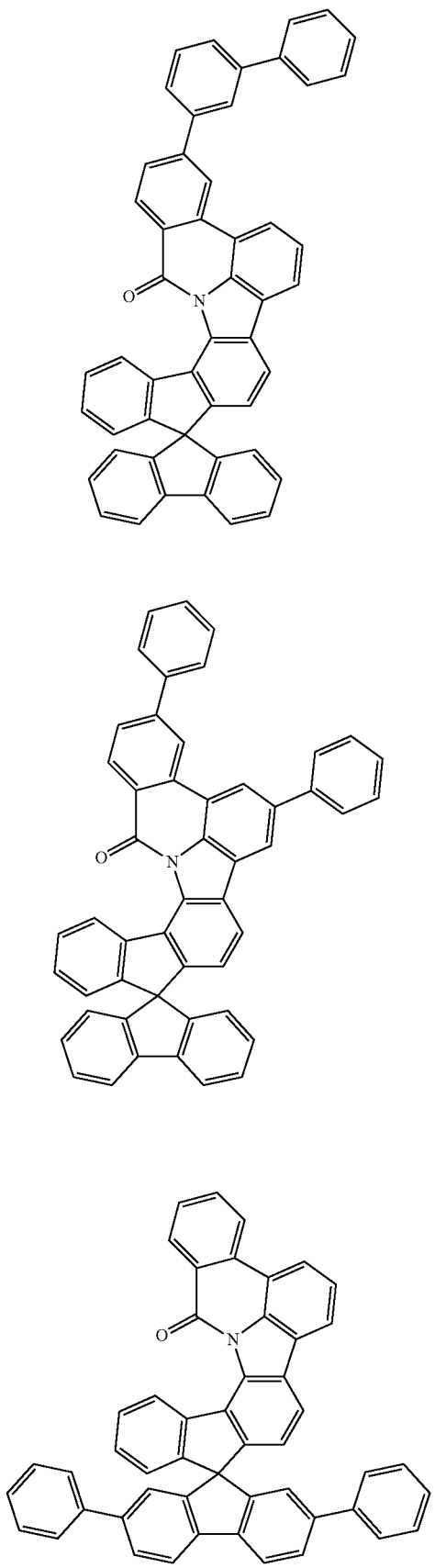
(4)
(5)
(6)

(7)
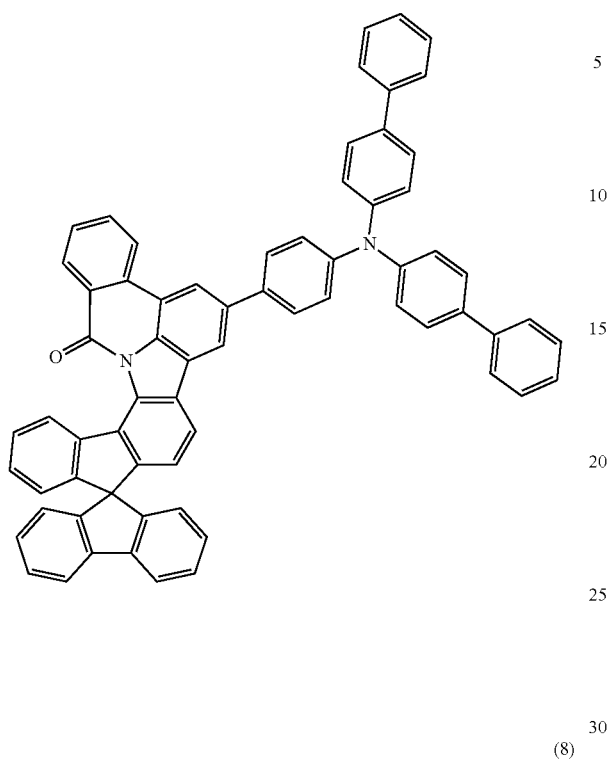
(8)
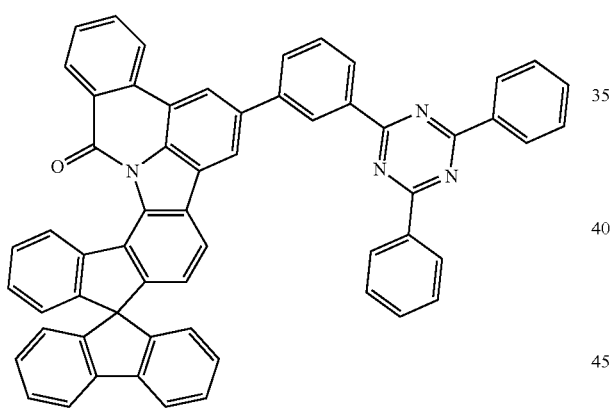
(9)
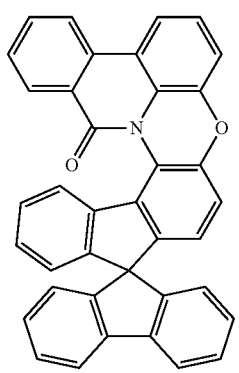
(10)
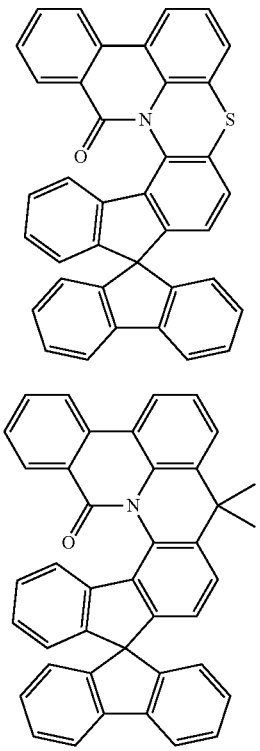
(11)
(12)
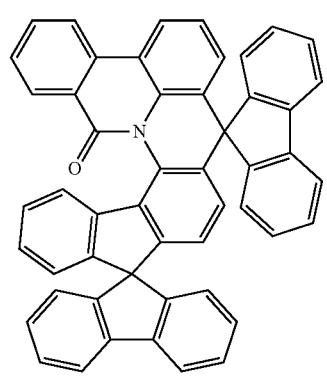
(13)
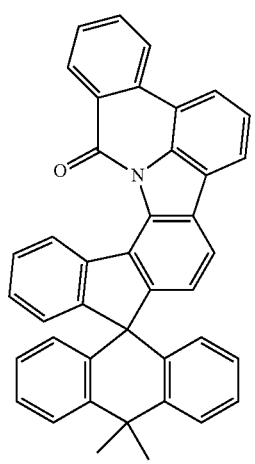

US 10,957,864 B2
(14)
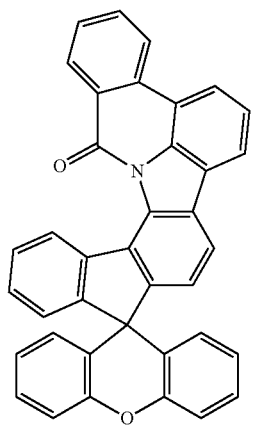
(15)
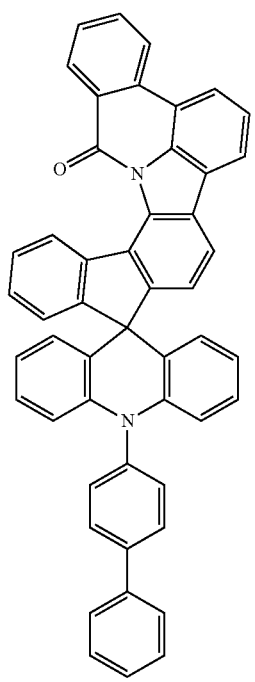
(16)
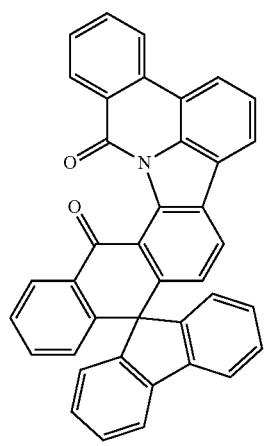
(17)
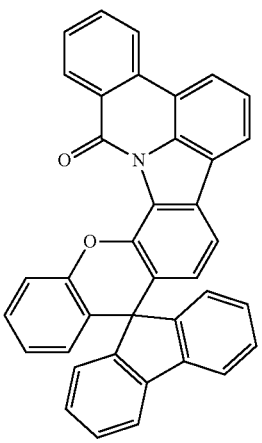
(18)
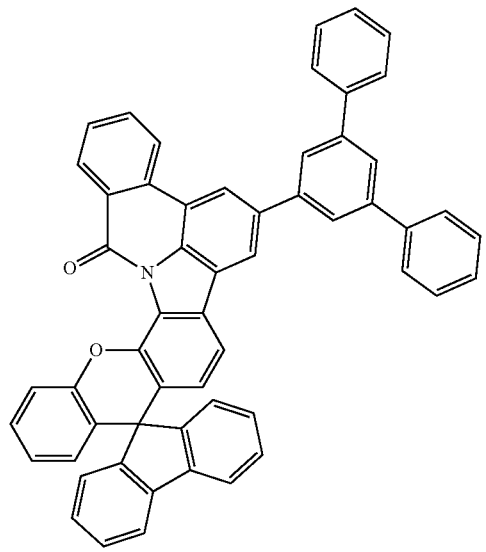
(19)
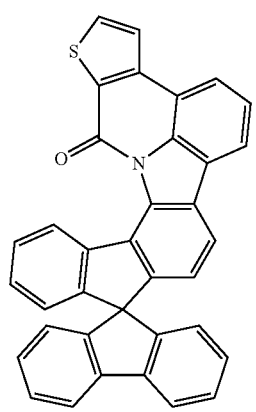

(20)
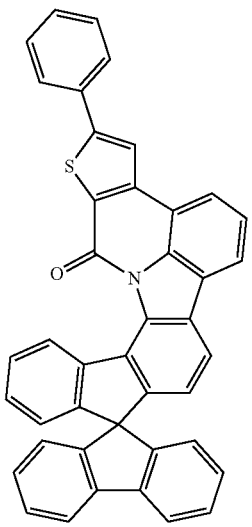
(21)
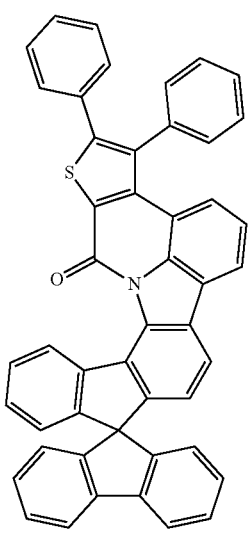
(22)
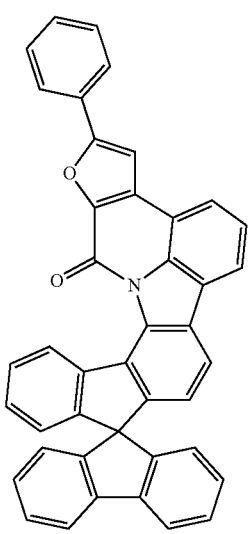
(23)
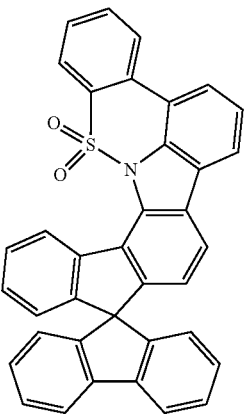
(24)
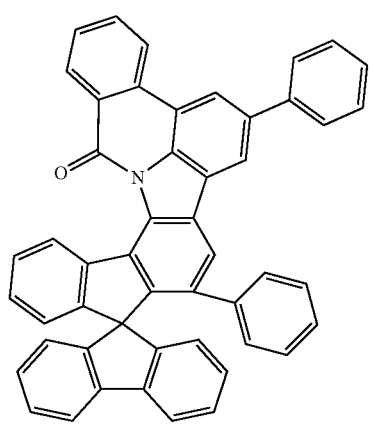
(25)
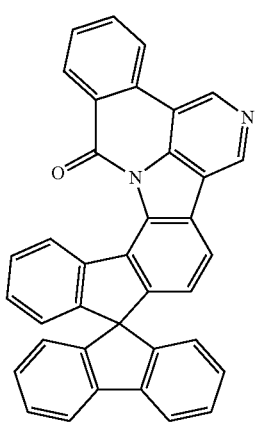

(26)
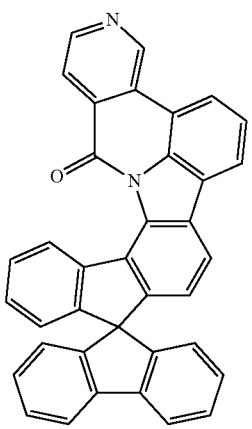
(27)
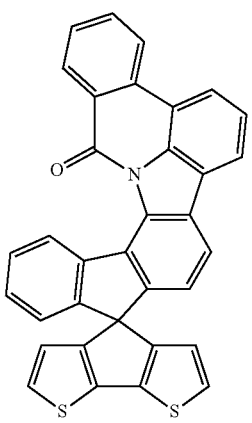
(28)
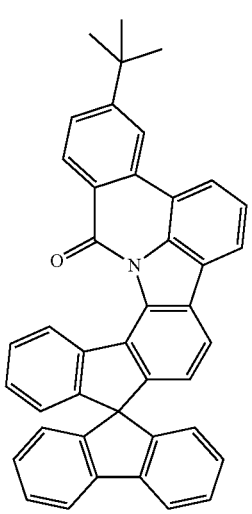
(29)
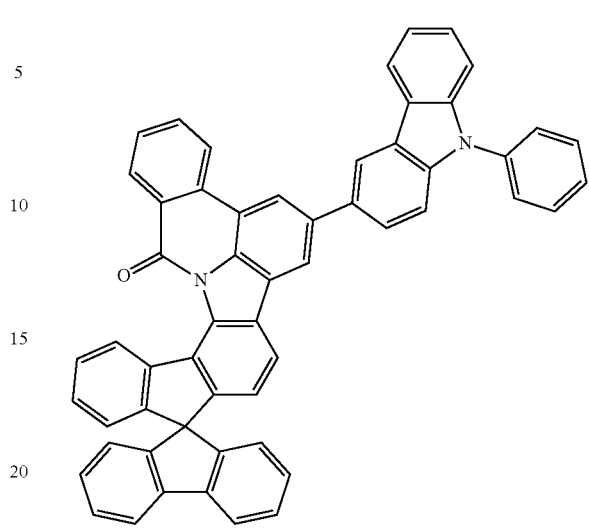
(30)
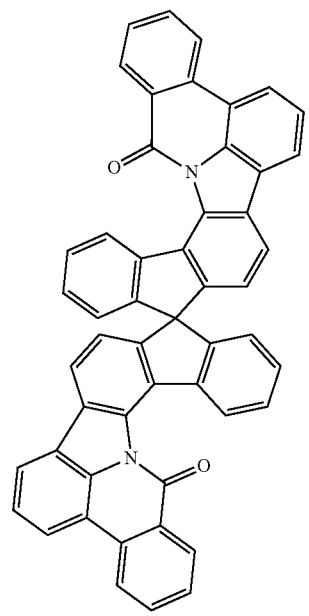
(31)
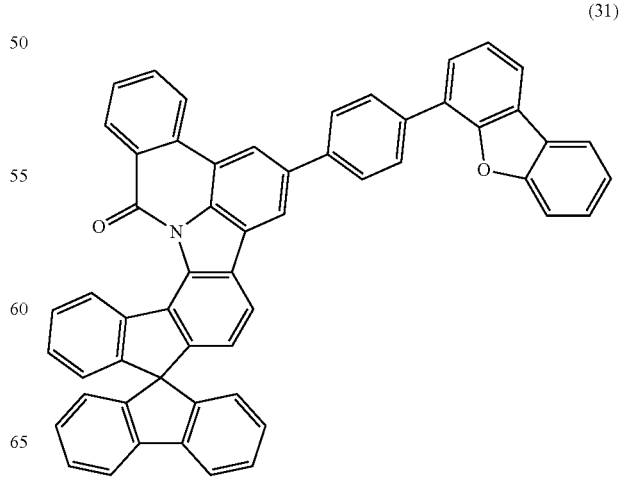

(32)
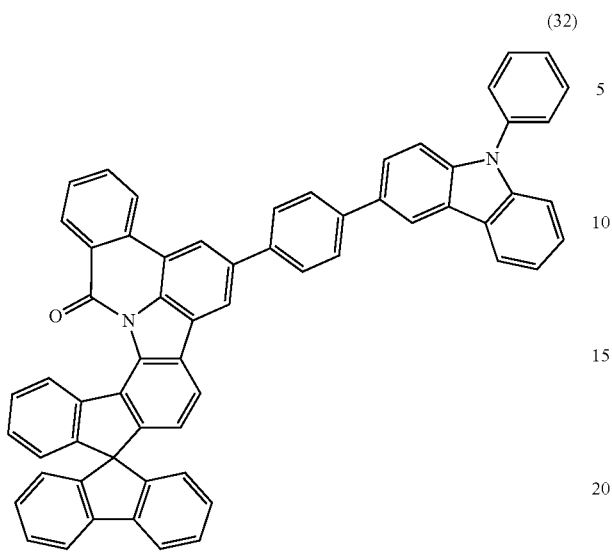
(35)
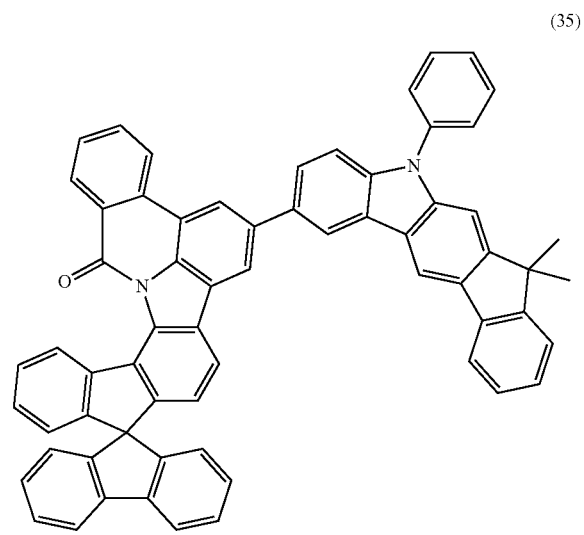
(33)
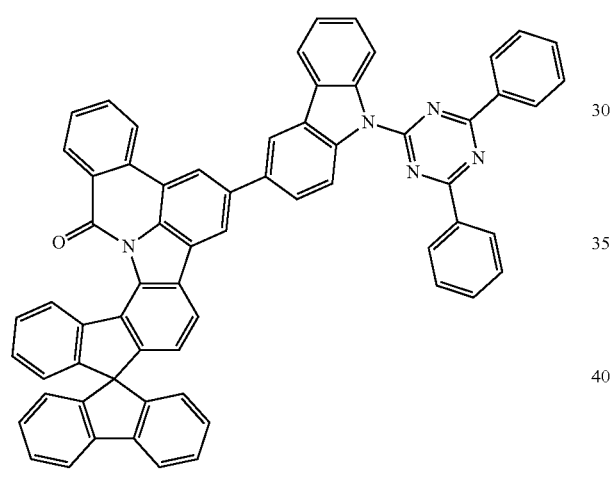
(36)
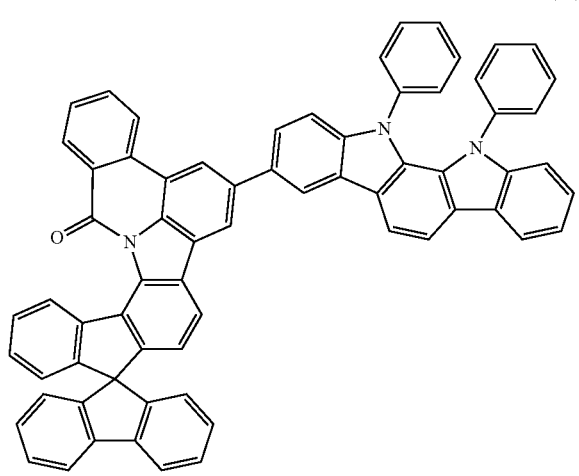
(34)
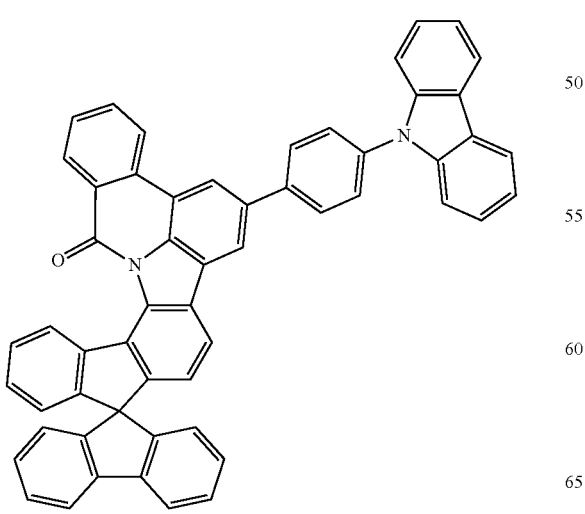
(37)
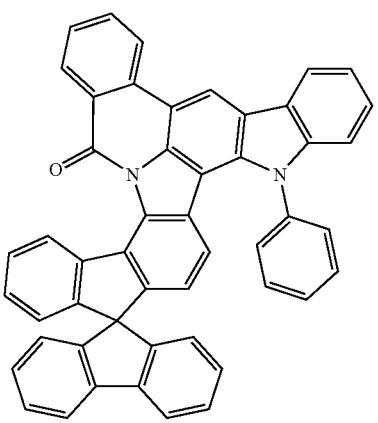

-continued
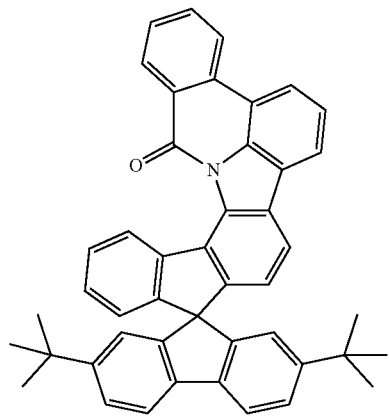
(38)
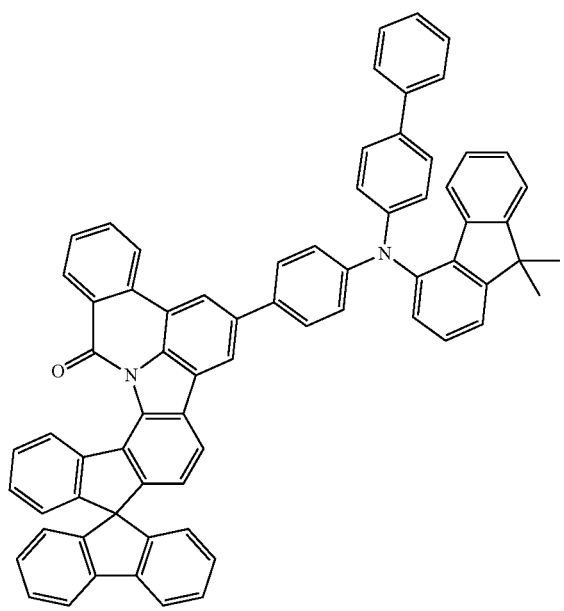
(39)
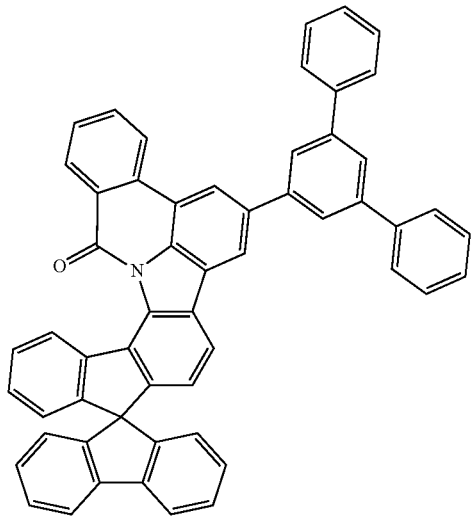
(40)
-continued
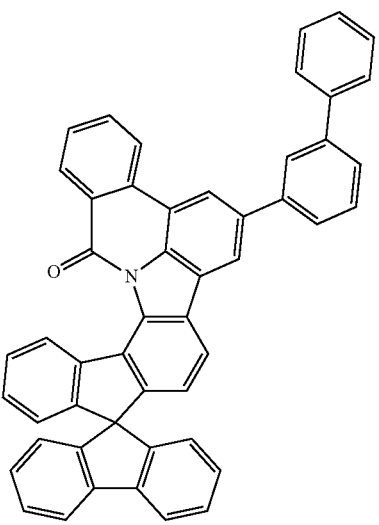
(41)
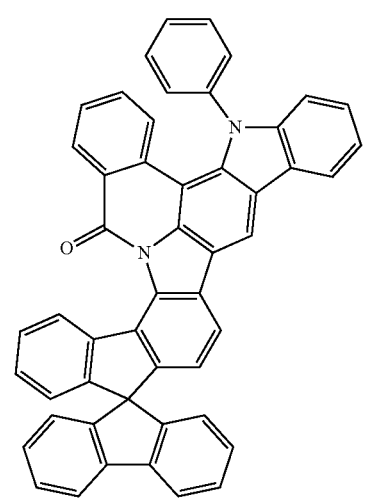
(42)
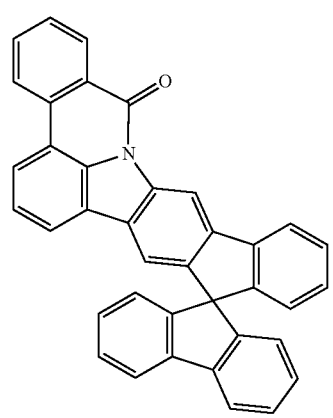
(43)

-continued
(44)
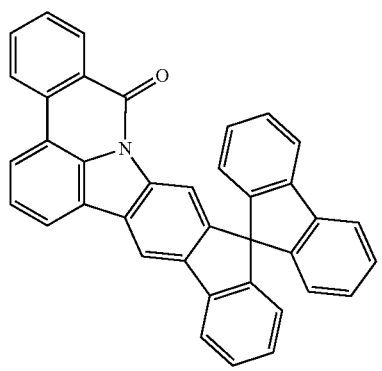
(45)
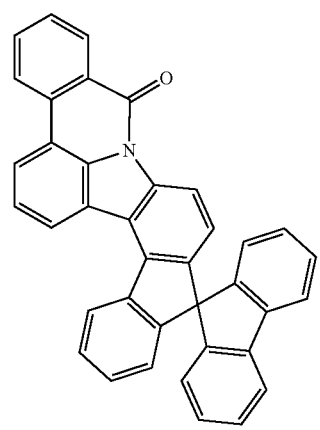
(46)
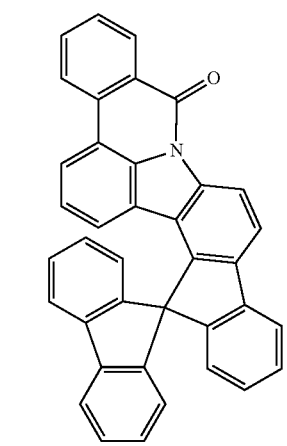
(47)
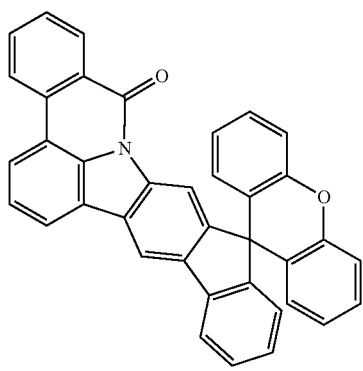
-continued
(48)
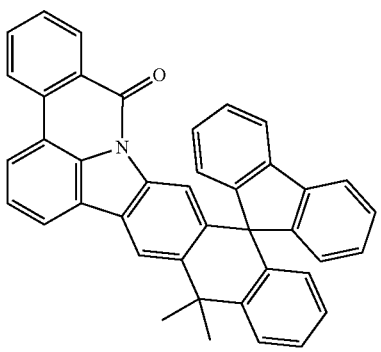
(49)
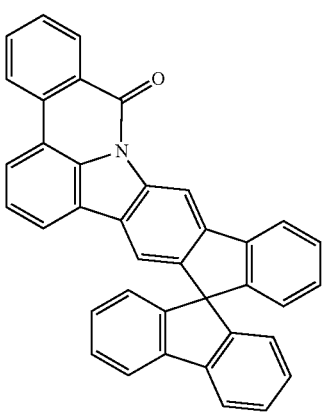
(50)
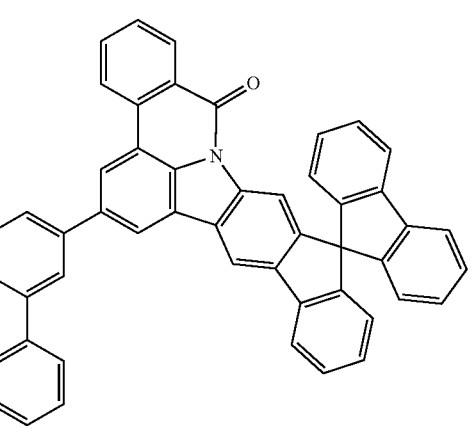

51
-continued
(51)
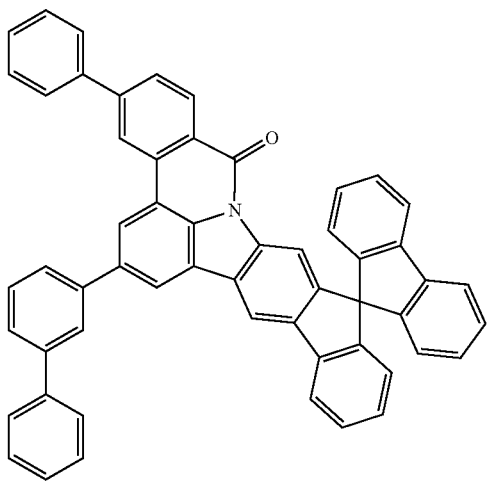
(52)
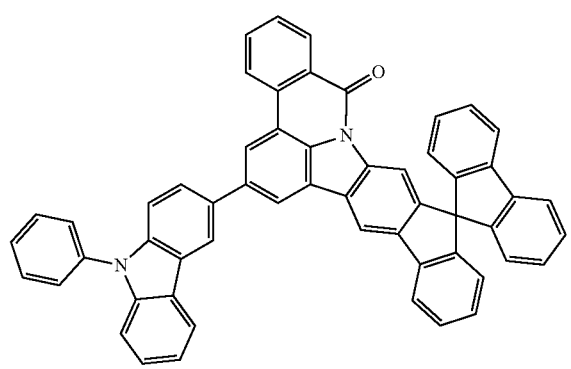
(53)
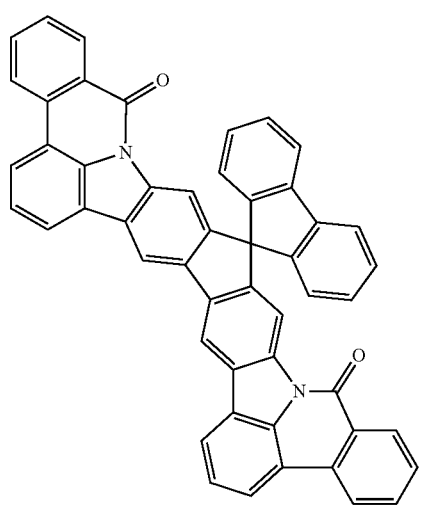
52
-continued
(54)
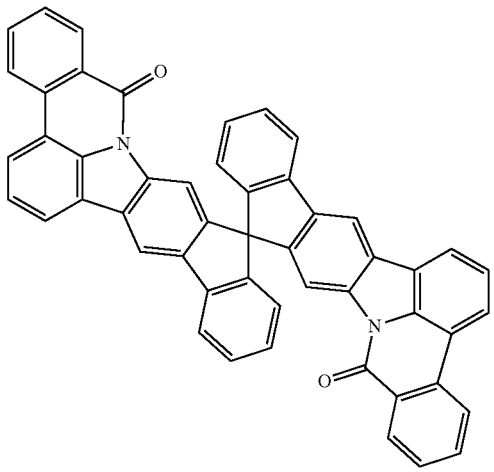
(55)
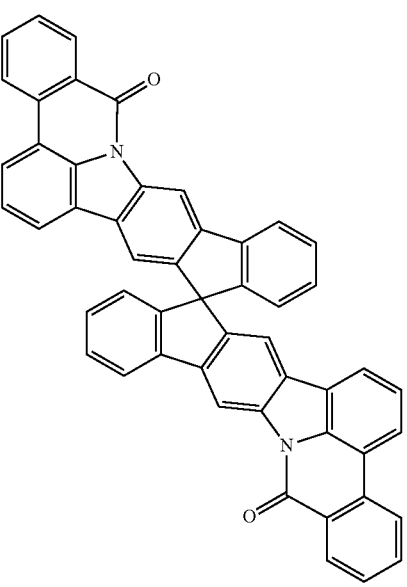
(56)
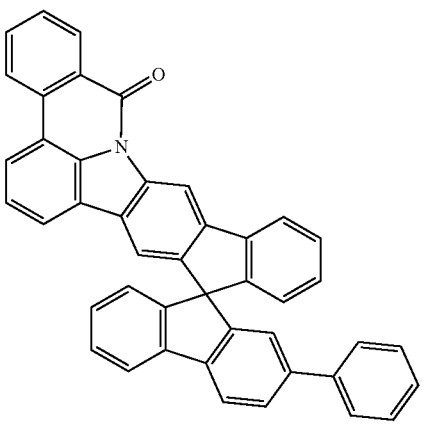

(57)
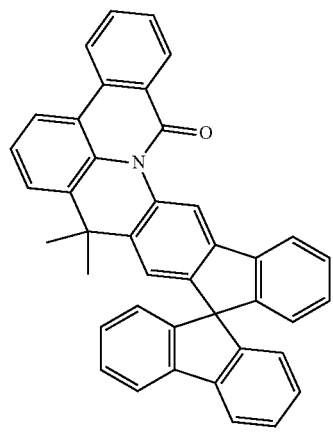
(60)
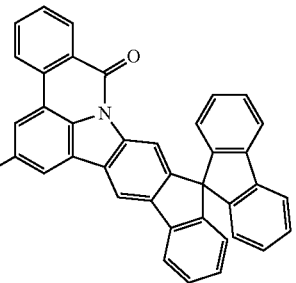
(61)
(58)
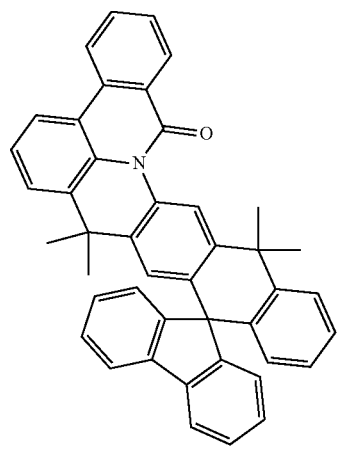
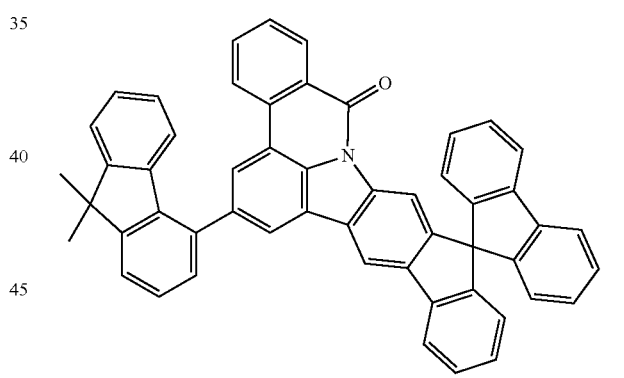
(62)
(59)
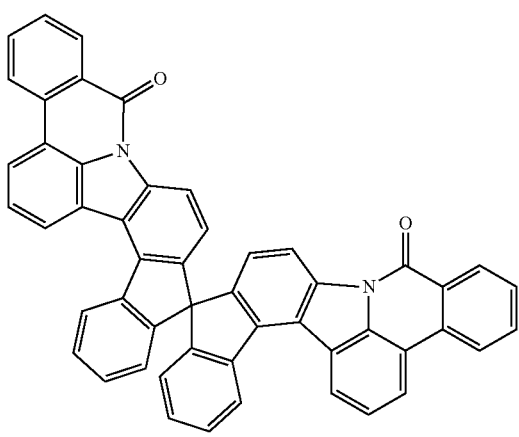
(63)
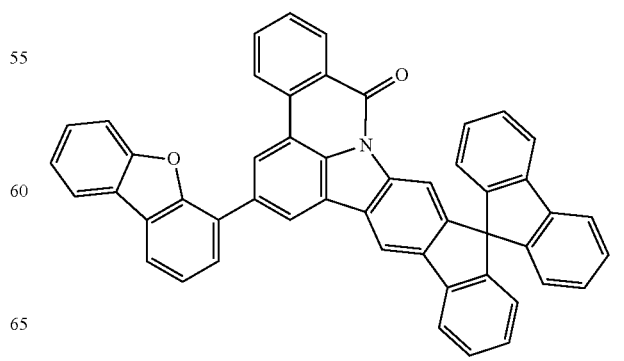

(64)
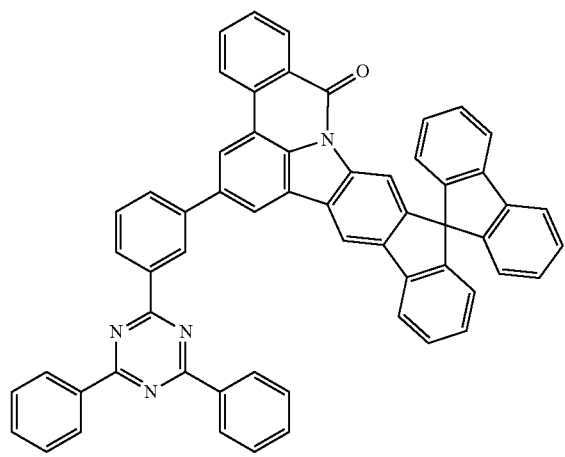
(65)
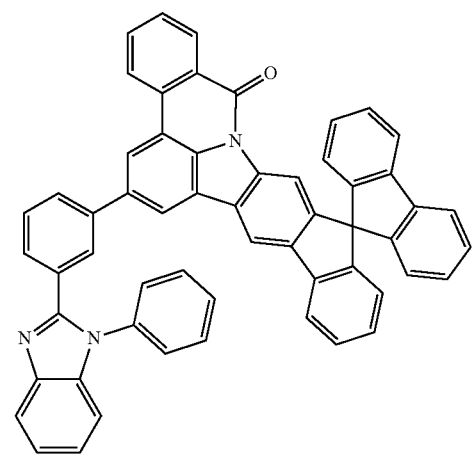
(66)
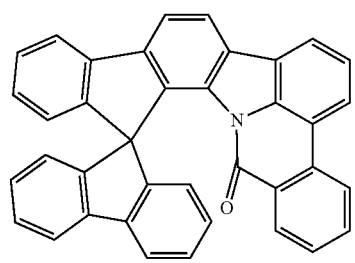
(67)
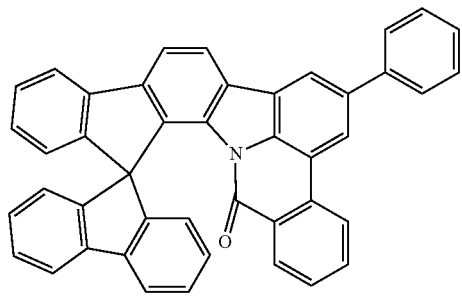
(68)
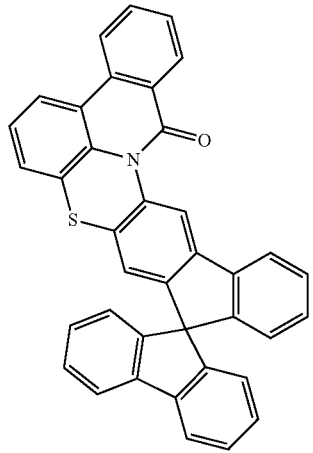
(69)
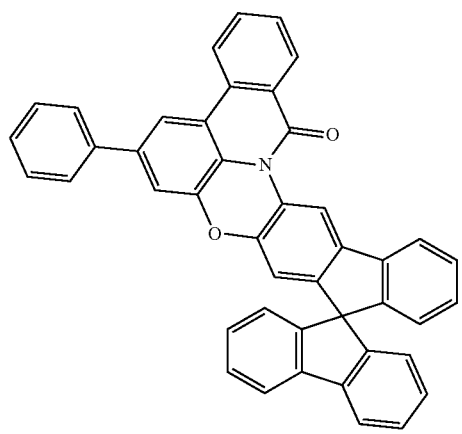
(70)
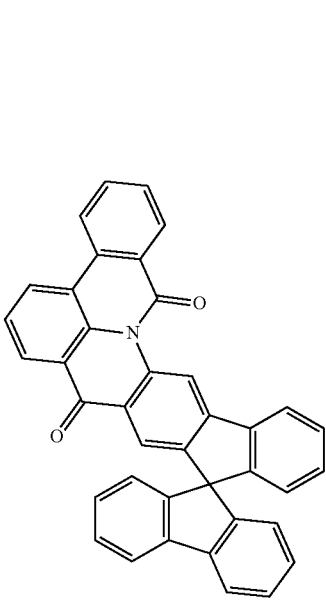

(71)
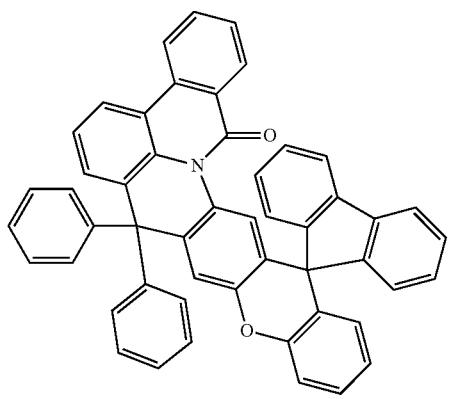
(72)
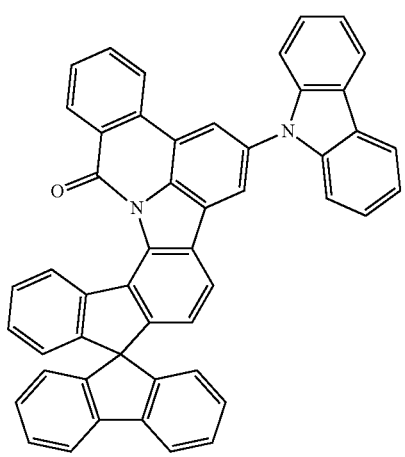
(73)
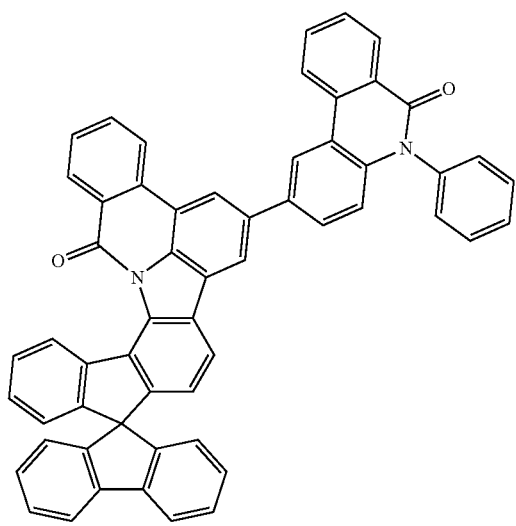
(74)
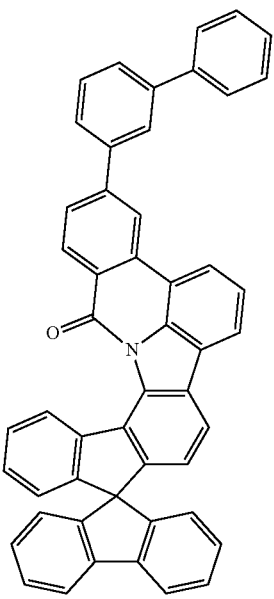
(75)
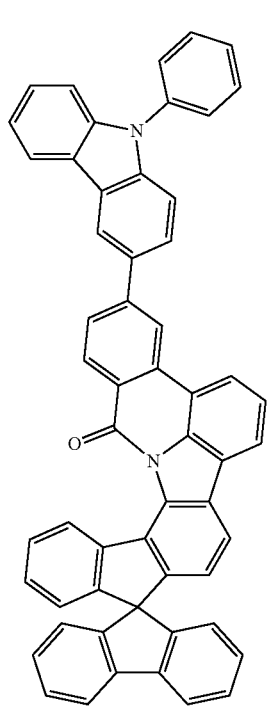

(76)
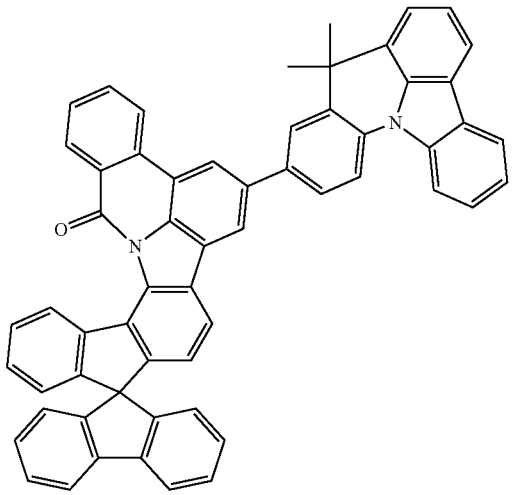
(77)
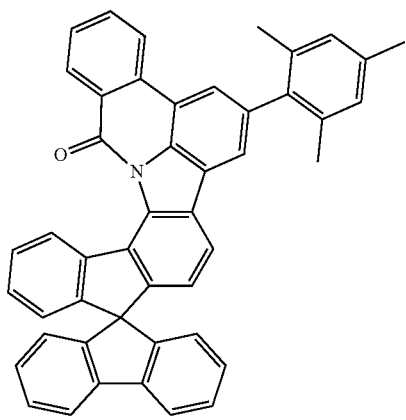
(78)
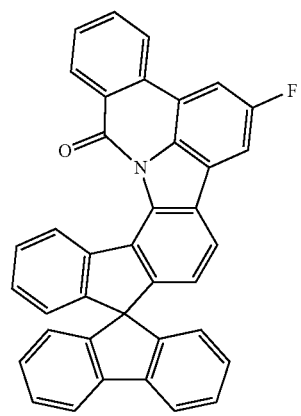
(79)
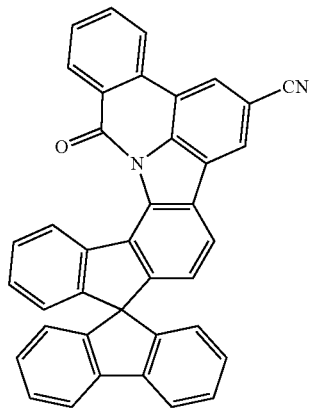
(80)
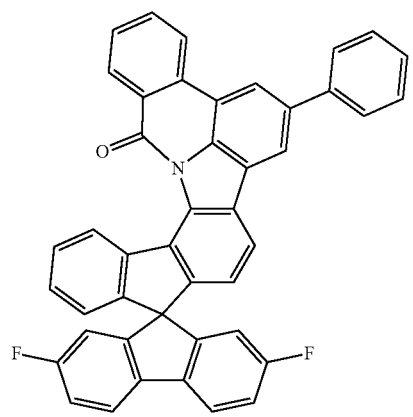
(81)
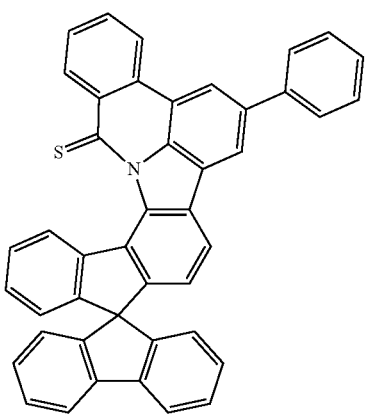

(82)
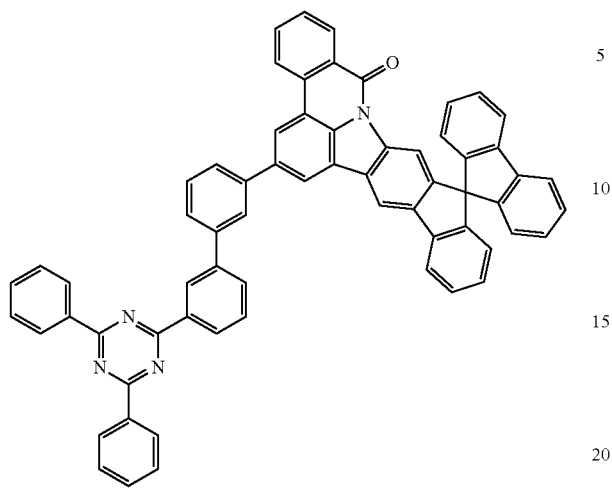
(83)
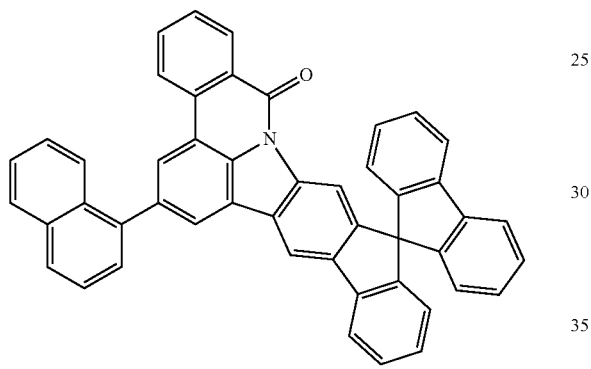
(84)
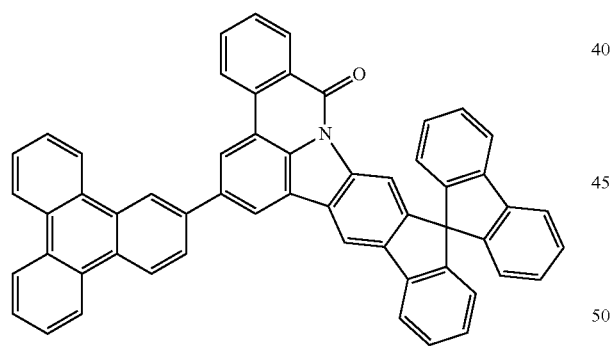
(85)
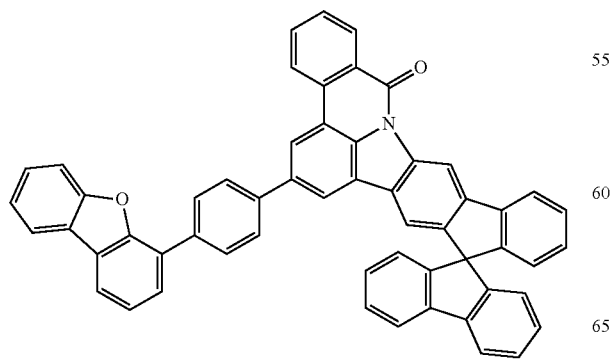
(86)
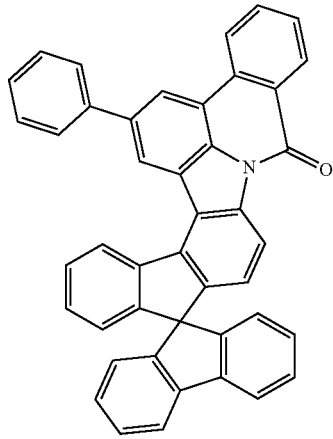
(87)
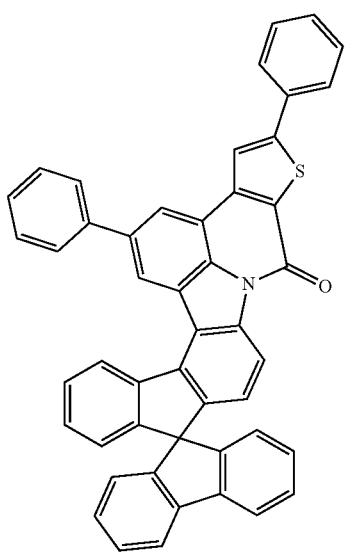
(88)
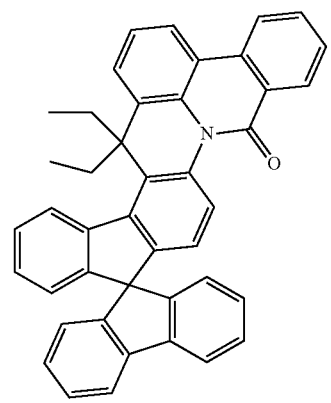

(89)
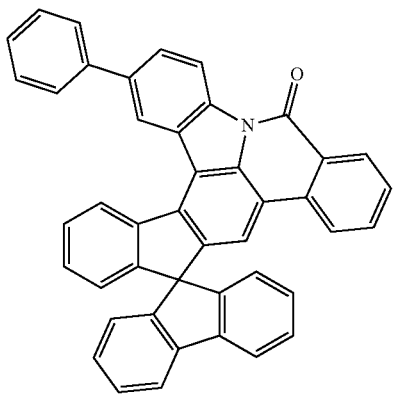
(90)
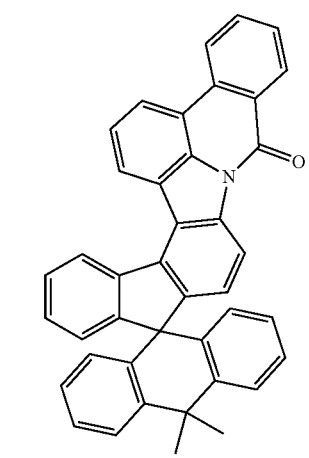
(91)
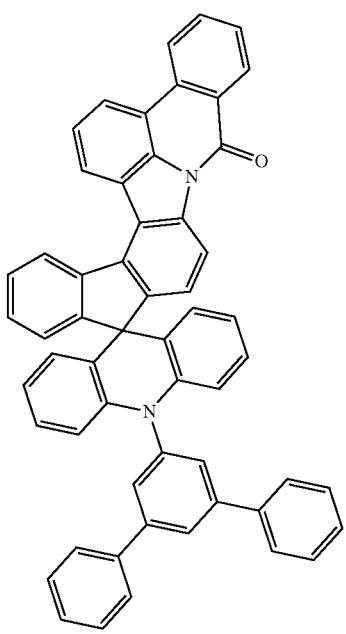
(92)
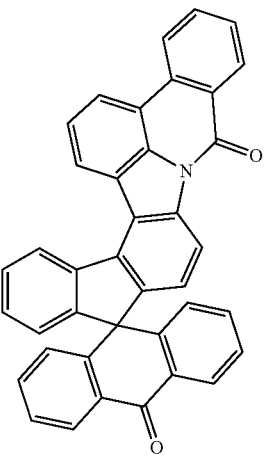
(93)
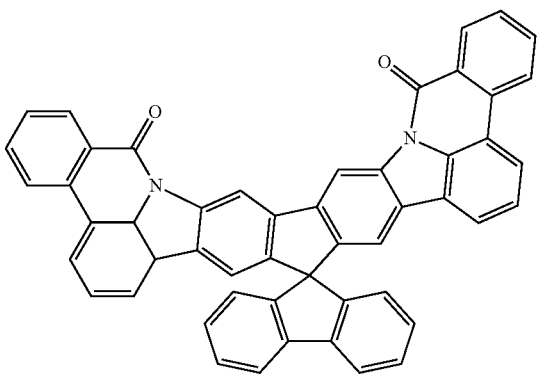
(94)
The compounds of the formula (1) or the preferred embodiments can be prepared by synthesis steps known to those skilled in the art, as shown in schematic form in scheme 1.

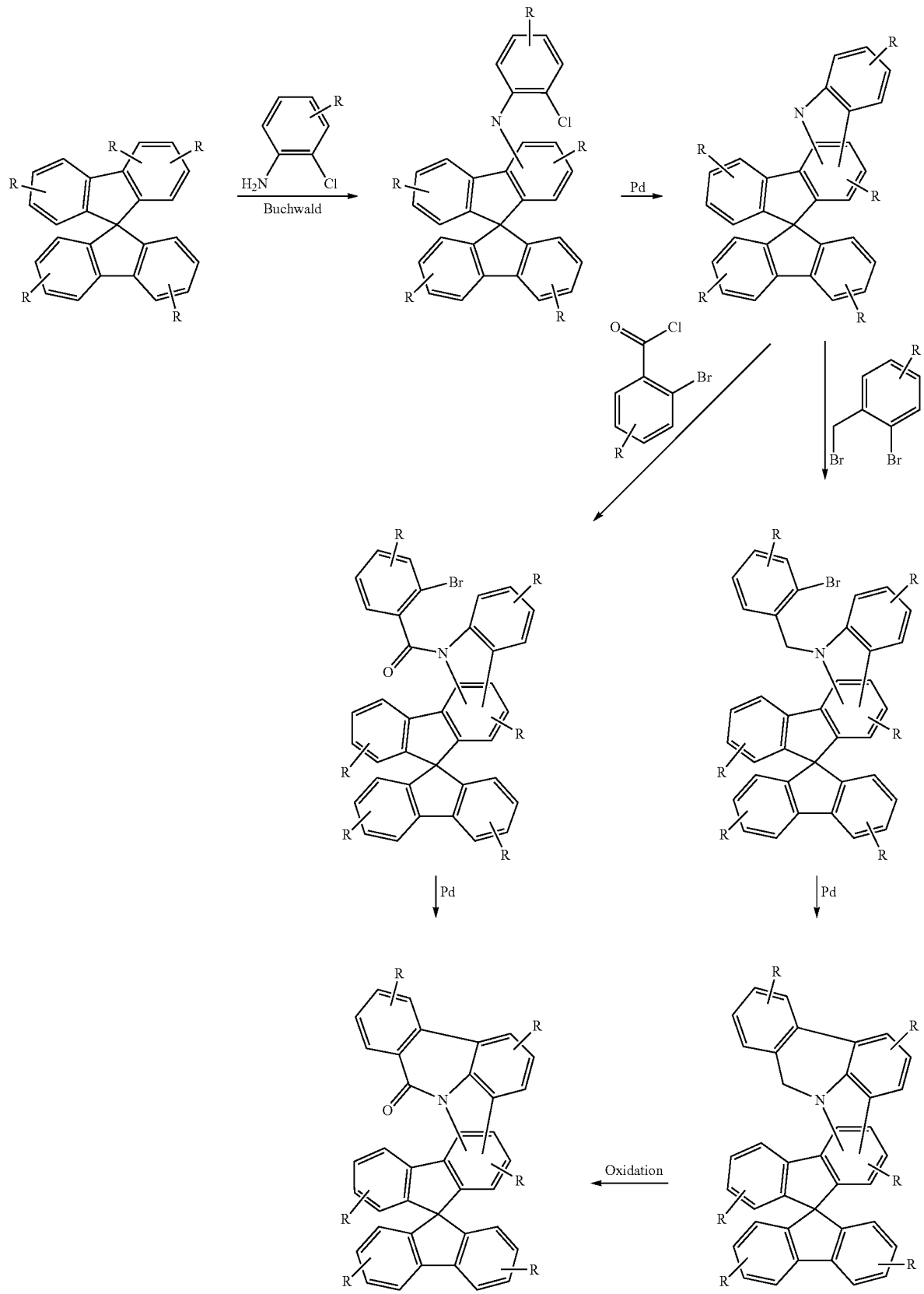

The synthesis proceeds from a halogen-functionalized, especially bromine-functionalized, spirobifluorene derivative. When the compounds contain $A^1$ or $A^2$ groups that are not single bonds, the starting materials are the corresponding functionalized spiro compounds having $A^1$ and $A^2$ groups. The latter is converted in a C—N coupling reaction, for example a Hartwig-Buchwald coupling, with an ortho-haloamino-substituted aromatic or heteroaromatic, for example an ortho-chloroaminobenzene derivative, followed by a palladium-catalyzed ring closure reaction to give the corresponding spirocarbazole derivative. Reaction with an ortho-halocarbonyl chloride to give the corresponding amide, followed by a palladium-catalyzed ring closure reaction, leads to the compounds of the invention. Alternatively, the reaction can also be effected with an ortho-halobenzyl bromide or a corresponding heteroaromatic compound, followed by a palladium-catalyzed ring closure reaction and oxidation of the cyclic amine to the lactam. Substituted compounds are obtainable by using correspondingly substituted reactants.

The above-described inventive compounds, especially compounds substituted by reactive leaving groups, such as bromine, iodine, chlorine, boronic acid or boronic ester, or by reactive polymerizable groups such as olefins or oxetanes, may find use as monomers for production of corresponding oligomers, dendrimers or polymers. The oligomerization or polymerization is preferably effected via the halogen functionality or the boronic acid functionality or via the polymerizable group. It is additionally possible to cross-link the polymers via groups of this kind. The compounds of the invention and polymers may be used in the form of a crosslinked or uncrosslinked layer.

The invention therefore further provides oligomers, polymers or dendrimers containing one or more of the above-detailed inventive compounds, wherein one or more bonds of the inventive compound to the polymer, oligomer or dendrimer are present. According to the linkage of the compound of the invention, it therefore forms a side chain of the oligomer or polymer or is incorporated in the main chain. The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to homopolymers or copolymers wherein the units of formula (1) or the above-recited preferred embodiments are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/22026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units. In addition, the polymers may contain triplet emitters either in copolymerized form or mixed in as a blend. Specifically the combination of units of formula (1') or the above-recited preferred embodiments with triplet emitters leads to particularly good results.

In addition, the compounds of formula (1) or the above-recited preferred embodiments may also be further functionalized and thus be converted to extended structures. Examples here include the Suzuki reaction with arylboronic acids or the Hartwig-Buchwald reaction with primary or secondary amines. Thus, the compounds of formula (1) or the above-recited preferred embodiments may also be bonded directly to phosphorescent metal complexes or else to other metal complexes.

For the processing of the compounds of the invention from the liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound and/or a further matrix material. Suitable emitting compounds and further matrix materials are listed at the back in connection with the organic electroluminescent device. This further compound may also be polymeric.

The compounds of the invention are suitable for use in an electronic device, especially in an organic electroluminescent device.

The present invention further provides for the use of the above-recited inventive compounds of formula (1) or of the preferred embodiments in an electronic device, especially in an organic electroluminescent device.

An electronic device in the context of the present invention is a device comprising at least one layer comprising at least one organic compound.

This component may also comprise inorganic materials or else layers formed entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitized solar cells (O-DSSCs), organic optical detectors, organic photoreceptors, organic field-quench devices (O-FQDs), light-emitting electrochemical cells (LECs), organic laser diodes (O-lasers) and organic plasmon emitting devices (D. M. Koller et al., Nature Photonics 2008, 1-4), but preferably organic electroluminescent devices (OLEDs), more preferably phosphorescent OLEDs.

The organic electroluminescent device comprises cathode, anode and at least one emitting layer. Apart from these layers, it may comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers Especially preferred are systems having three emitting layers, where the three layers show blue, green and orange or red emission (for the basic construction see, for example, WO 2005/011013).

The compound of the invention according to the above-detailed embodiments may be used in different layers, according to the exact structure. Preference is given to an organic electroluminescent device comprising a compound of formula (1) or the above-recited preferred embodiments as matrix material for fluorescent or phosphorescent emitters, especially for phosphorescent emitters, and/or in a hole blocker layer and/or in an electron transport layer and/or in an electron-blocking or exciton-blocking layer and/or in a hole transport layer, according to the exact substitution.

In a preferred embodiment of the invention, the compound of formula (1) or the above-recited preferred embodiments is used as matrix material for a fluorescent or phosphorescent compound, especially for a phosphorescent compound, in an emitting layer. In this case, the organic electroluminescent device may contain an emitting layer, or it may contain a plurality of emitting layers, where at least one emitting layer contains at least one compound of the invention as matrix material.

When the compound of formula (1) or the above-recited preferred embodiments is used as matrix material for an emitting compound in an emitting layer, it is preferably used in combination with one or more phosphorescent materials (triplet emitters). Phosphorescence in the context of this invention is understood to mean luminescence from an excited state having higher spin multiplicity, i.e. a spin state >1, especially from an excited triplet state. In the context of this application, all luminescent complexes with transition metals or lanthanides, especially all iridium, platinum and copper complexes, shall be regarded as phosphorescent compounds.

The mixture of the compound of formula (1) or the above-recited preferred embodiments and the emitting compound contains between 99% and 1% by volume, preferably between 98% and 10% by volume, more preferably between 97% and 60% by volume and especially between 95% and 80% by volume of the compound of formula (1) or the above-recited preferred embodiments, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

A further preferred embodiment of the present invention is the use of the compound of formula (1) or the above-recited preferred embodiments as matrix material for a phosphorescent emitter in combination with a further matrix material. Particularly suitable matrix materials which can be used in combination with the inventive compounds are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example according to WO 2007/063754 or WO 2008/056746, indenocarbazole derivatives, for example according to WO 2010/136109, WO 2011/000455, WO 2013/041176 or WO 2013/056776, azacarbazole derivatives, for example according to EP 1617710, EP 1617711, EP 1731584. JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, or triphenylene derivatives, for example according to WO 2012/048781. It is likewise possible for a further phosphorescent emitter having shorter-wavelength emission than the actual emitter to be present as co-host in the mixture, or a compound not involved in charge transport to a significant extent, if at all, as described, for example, in WO 2010/108579.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, indium, palladium, platinum, silver, gold or europium, especially compounds containing iridium or platinum.

Examples of the above-described emitters can be found in applications WO 00/70655, WO 2001/41512, WO 2002/02714, WO 2002/15645, EP 1191613, EP 1191612, EP 1191614, WO 2005/033244, WO 2005/019373, US 2005/0258742, WO 2010/086089, WO 2011/157339, WO 2012/007086, WO 2012/163471, WO 2013/000531, WO 2013/020631, WO 2014/008982 and WO 2014/023377. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In a further preferred embodiment of the invention, the compound of formula (1) or the above-recited preferred embodiments is used as electron transport material in an electron transport or electron injection layer. In this case, the emitting layer may be fluorescent or phosphorescent. When the compound is used as electron transport material, it may be preferable for it to be doped, for example with alkali metal complexes, for example LiQ (lithium hydroxyquinolinate).

In yet a further preferred embodiment of the invention, the compound of formula (1) or the above-recited preferred embodiments is used in a hole blocker layer, A hole blocker layer is understood to be a layer which directly adjoins an emitting layer on the cathode side.

It is additionally possible to use the compound of formula (1) or the above-recited preferred embodiments both in a hole blocker layer or electron transport layer and as matrix in an emitting layer.

In yet a further embodiment of the invention, the compound of formula (1) or the above-recited preferred embodiments is used in a hole transport layer or in an electron blocker layer or exciton blocker layer.

In the further layers of the organic electroluminescent device of the invention, it is possible to use any materials as typically used according to the prior art. The person skilled in the art will therefore be able, without exercising inventive skill, to use any materials known for organic electroluminescent devices in combination with the inventive compounds of formula (1) or the above-recited preferred embodiments.

Additionally preferred is an organic electroluminescent device, characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. It is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example, M. S. Arnold et al., *Appl. Phys. Lett.* 2008, 92, 053301).

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution. These methods are especially also suitable for oligomers, dendrimers and polymers.

In addition, hybrid methods are possible, in which, for example, one or more layers are applied from solution and one or more further layers are applied by vapor deposition.

These methods are known in general terms to those skilled in the art and can be applied by those skilled in the art without exercising inventive skill to organic electroluminescent devices comprising the compounds of the invention.

The inventive compounds and the inventive organic electroluminescent devices are notable for the following surprising advantages over the prior art:

1. The inventive compounds or compounds of formula (1) or the above-recited preferred embodiments, especially used as matrix material for phosphorescent emitters, lead to high efficiencies and to long lifetimes. This is especially true when the compounds are used as matrix material for a red-, yellow- or green-phosphorescing emitter.
2. Organic electroluminescent devices containing the inventive compounds have a low operating voltage. This leads to high power efficiencies.
3. The inventive compounds have high thermal stability and high glass transition temperatures.
4. When used as electron transport material, the inventive compounds also lead to very good properties in relation to efficiency, lifetime and operating voltage of organic electroluminescent devices.

These abovementioned advantages are not accompanied by a deterioration in the further electronic properties.

The invention is illustrated in detail by the examples which follow, without any intention of restricting it thereby. The person skilled in the art will be able to use the information given to execute the invention over the entire scope disclosed and to prepare further compounds of the invention without exercising inventive skill and to use them in electronic devices or to employ the process of the invention.

EXAMPLES

The syntheses which follow, unless stated otherwise, are conducted under a protective gas atmosphere. The reactants can be sourced from ALDRICH or ABCR. The numbers given in square brackets for the compounds known from the literature indicate the CAS numbers of these compounds.

Synthesis Examples

Example A: Synthesis of 1-bromospiro-9,9'-bifluorene, 3-bromospiro-9,9'-bifluorene, 4-bromospiro-9, 9'-bifluorene, 4,4'-dibromospiro-9,9'-bifluorene, 3,6-dibromospiro-9,9'-bifluorene a) 1-Bromospiro-9,9'-bifluorene

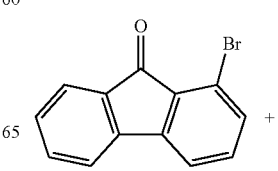

-continued

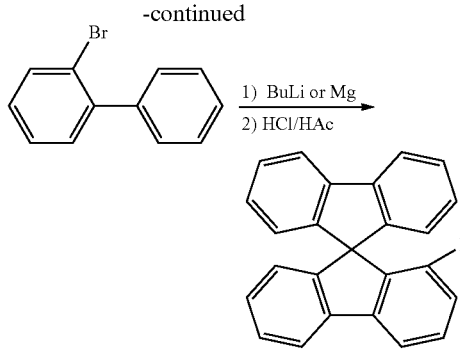

2.7 g (110 mmol) of iodine-activated magnesium turnings and a mixture of 25.6 g (110 mmol) of 2-bromobiphenyl, 0.8 mL of 1,2-dichloroethane, 50 mL of 1,2-dimethoxyethane, 400 mL of THF and 200 mL of toluene are used to prepare the corresponding Grignard reagent by trace heating with an oil bath at 70° C. Once the magnesium has reacted fully, the mixture is cooled to room temperature and then a solution of 25.9 g (100 mmol) of 1-bromofluorenone [36804-63-4] in 500 mL of THF is added dropwise, and the reaction mixture is heated to 50° C. for 4 h and then stirred at room temperature for a further 12 h. 100 mL of water are added, the mixture is stirred briefly, the organic phase is removed and the solvent is removed under reduced pressure. The residue is suspended in 500 mL of glacial acetic acid heated to 40° C., 0.5 mL of conc. sulfuric acid is added to the suspension and the mixture is then stirred at 100° C. for 2 h. After cooling, the precipitated solid is filtered off with suction and washed once with 100 mL of glacial acetic acid and three times with 100 mL each time of ethanol, and finally recrystallized from dioxane. Yield: 26.9 g (68 mmol), 68%; purity about 98% by $^1$H NMR.

| Br-biphenyl | Br-flourenone | Product: Br-spiro | Yield |
|---|---|---|---|
| 2052-07-5 | 2041-19-2 | | 85% |
| 13029-09-9 | 486-25-9 | 116109-88-6 | 90% |
| 2052-07-5 | 216312-73-1 | | 85% |
| 13029-09-9 | 4269-17-4 | 1257321-41-7 | 90% |

Example 1a: (2-Chlorophenyl)-4-spiro-9,9'-bifluorenylamine

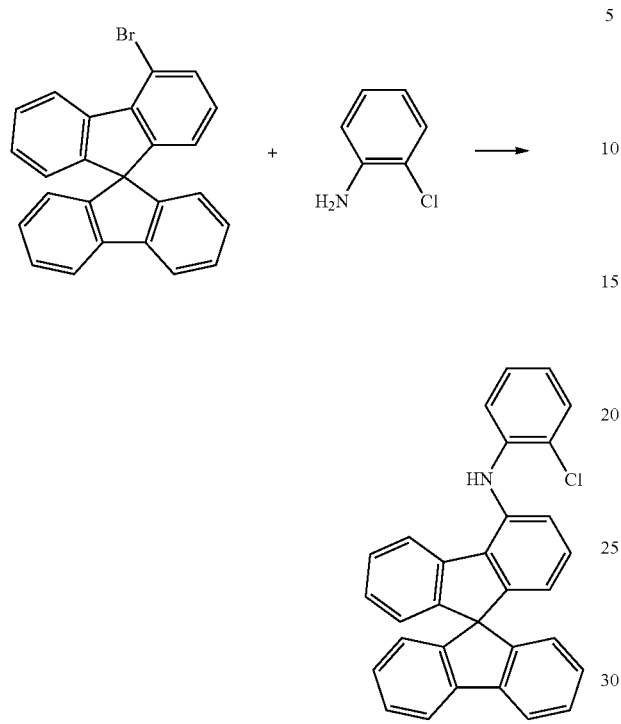

54 g (137 mmol) of 4-bromospiro-9,9'-bifluorene, 17.9 g (140 mmol) of 2-chloroaniline, 68.2 g (710 mmol) of sodium tert-butoxide, 613 mg (3 mmol) of palladium(II) acetate and 3.03 g (5 mmol) of dppf are dissolved in 1.3 L of toluene and stirred under reflux for 5 h. The reaction mixture is cooled down to room temperature, extended with toluene and filtered through Celite. The filtrate is concentrated under reduced pressure and the residue is crystallized from toluene/heptane. The product is isolated as a colorless solid. Yield: 52.2 g (118 mmol), 86% of theory.

In an analogous manner, it is possible to prepare the following compounds:

| | Reactant 1 | Reactant 2 | Product | Yield |
|---|---|---|---|---|
| 1b | | 7285-66-7 | | 83% |

| Reactant 1 | Reactant 2 | Product | Yield |
|---|---|---|---|
| 1c 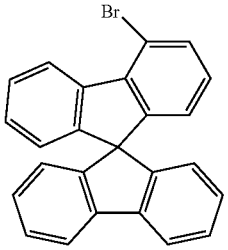 [SMILES: Brc1cccc2c1-c1ccccc1C21c2ccccc2-c2ccccc21] | 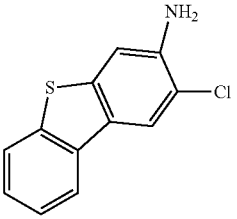<br>858426-71-8 | 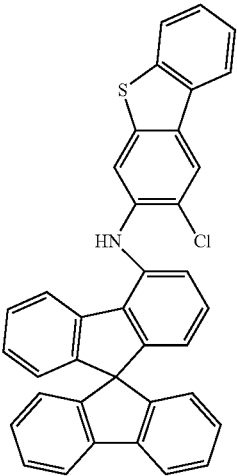 [SMILES: Clc1cc2c(cc1Nc1cccc3c1-c1ccccc1C31c3ccccc3-c3ccccc31)sc1ccccc12] | 78% |
| 1d 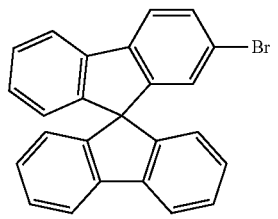<br>171408-76-7 | 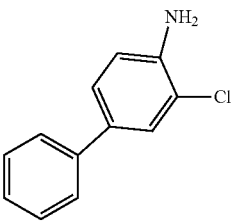<br>7285-66-7 | 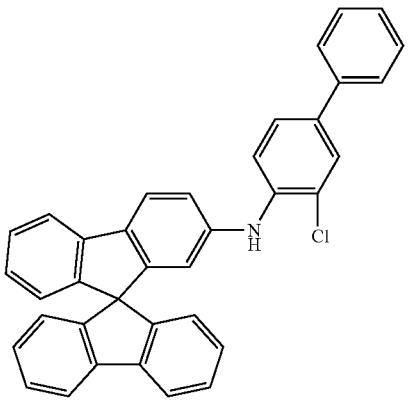 [SMILES: Clc1cc(-c2ccccc2)ccc1Nc1ccc2c(c1)C1(c3ccccc3-c3ccccc31)c1ccccc1-2] | 72% |
| 1e 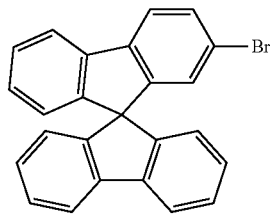<br>171408-76-7 | 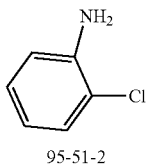<br>95-51-2 | 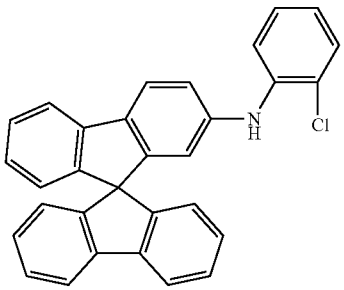 [SMILES: Clc1ccccc1Nc1ccc2c(c1)C1(c3ccccc3-c3ccccc31)c1ccccc1-2] | 74% |

-continued

| | Reactant 1 | Reactant 2 | Product | Yield |
|---|---|---|---|---|
| 1f | [9,9'-spirobifluorene with Br at 4 and 4' positions] | 2-chloroaniline (95-51-2) | [spirobifluorene with two (2-chlorophenyl)amino groups at 4,4' positions] | 68% |
| 1g | [9,9'-spirobifluorene with Br at 3 position] | 2-chloroaniline (95-51-2) | [spirobifluorene with (2-chlorophenyl)amino at 3 position] | 79% |
| 1h | [9,9'-spirobifluorene with Br at 3 and 3' positions] | 2-chloroaniline (95-51-2) | [spirobifluorene with two (2-chlorophenyl)amino groups at 3,3' positions] | 63% |
| 1i | [9,9'-spirobifluorene with Br at 1 position] | 2-chloroaniline (95-51-2) | [spirobifluorene with (2-chlorophenyl)amino at 1 position] | 61% |

Example 2a: Spiro[9H-fluoren-9,7'(1'H)-indeno[1,2-a]carbazole]

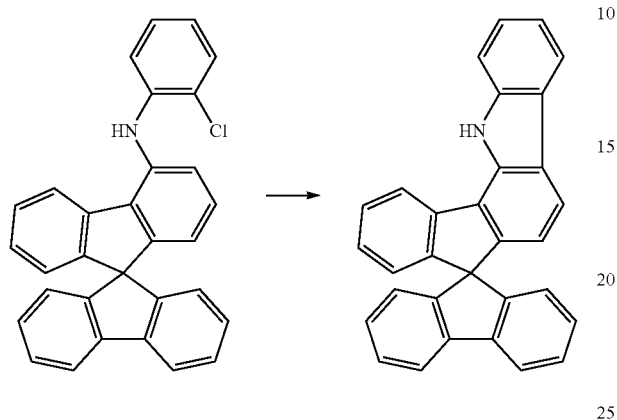

45 g (102 mmol) of (2-chlorophenyl)-4-spiro-9,9'-bifluorenylamine, 56 g (409 mmol) of potassium carbonate, 4.5 g (12 mmol) of tricyclohexylphosphine tetrafluoroborate and 1.38 g (6 mmol) of palladium(II) acetate are suspended in 500 mL of dimethylacetamide and stirred under reflux for 6 h. After cooling, the reaction mixture is with 300 mL of water and 600 mL of dichloromethane. The mixture is stirred for a further 30 min, the organic phase is separated off and filtered through a short Celite bed, and then the solvent is removed under reduced pressure. The crude product is subjected to hot extraction with toluene and recrystallized from toluene. The product is isolated as a beige solid. Yield: 32.5 g (80 mmol correspond to 78% of theory).

In an analogous manner, it is possible to prepare the following compounds:

| | Reactant | Product | Yield |
|---|---|---|---|
| 2b | | | 72% |

|  | Reactant | Product | Yield |
|---|---|---|---|
| 2c | 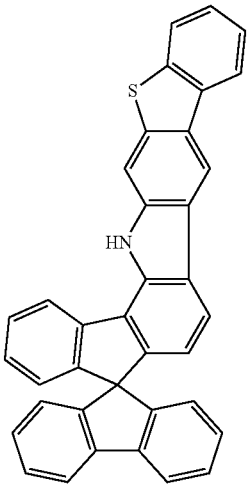 [SMILES: c1ccc2c(c1)-c1ccccc1C21c2ccccc2-c2c1ccc1c2[nH]c2cc3sc4ccccc4c3cc21] | | 73% |
| 2d | | | 56% |
| 2e | 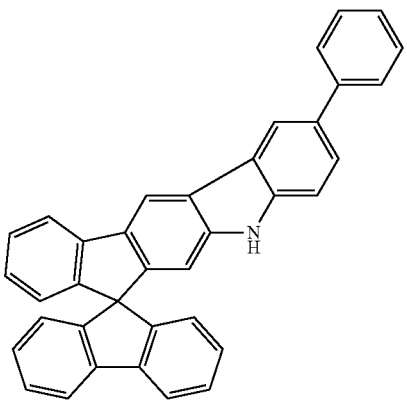 [SMILES: c1ccc(-c2ccc3[nH]c4cc5c(cc4c3c2)-c2ccccc2C52c3ccccc3-c3ccccc32)cc1] | 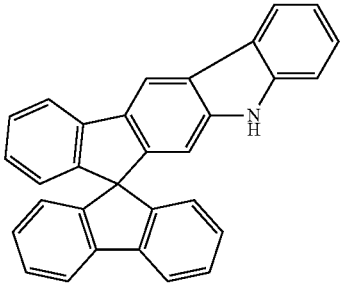 [SMILES: c1ccc2c(c1)-c1ccccc1C21c2ccccc2-c2cc3c(cc21)[nH]c1ccccc13] | 71% |

-continued

| | Reactant | Product | Yield |
|---|---|---|---|
| 2f | | | 67% |
| 2g | | | 51% |
| 2h | | | 43% |
| 2i | | | 47% |

Example 3a: Nucleophilic Substitution

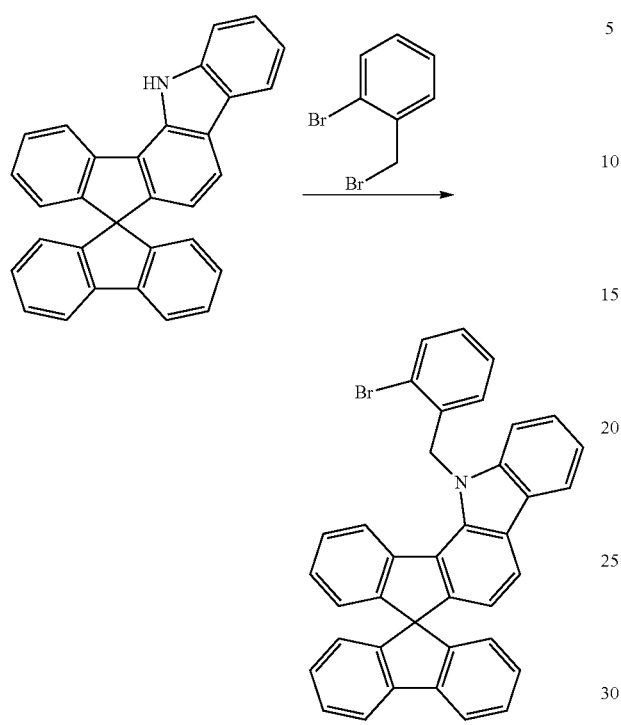

In a 500 mL four-neck flask, 760 mg (19 mmol) of sodium hydride are initially charged in 50 mL of THF. By means of a dropping funnel, 7.0 g (17 mmol) of spirocarbazole 2a, dissolved in 200 mL of THF, are added dropwise and the mixture is stirred for a further 1 h. Subsequently, 4.3 g (17 mmol) of 2-bromobenzyl bromide, dissolved in 100 mL of THF, are added dropwise and the mixture is stirred at room temperature for 5 h until conversion is complete. The reaction mixture is added to ice and warmed to room temperature. The precipitated solid is filtered and washed with n-heptane and dried under reduced pressure. The product is obtained as a colorless solid. Yield: 9.3 g (16 mmol, corresponding to 94% of theory).

In an analogous manner, it is possible to obtain the following compounds:

| Ex. | Reactant 1 | Reactant 2 | Product | Yield |
|---|---|---|---|---|
| 3b | (spirocarbazole with phenyl) | 172976-02-2 | (N-(2-bromobenzyl) product) | 79% |

| Ex. | Reactant 1 | Reactant 2 | Product | Yield |
|---|---|---|---|---|
| 3c | 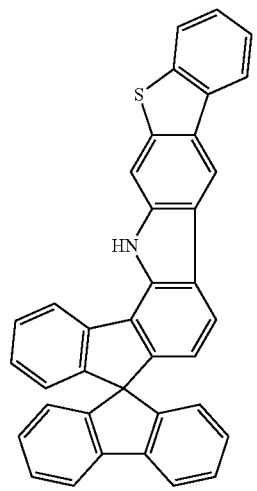 [SMILES: c1ccc2c(c1)-c1ccccc1C21c2ccccc2-c2c1ccc1c2[nH]c2cc3sc4ccccc4c3cc21] | 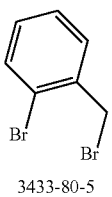  3433-80-5 | 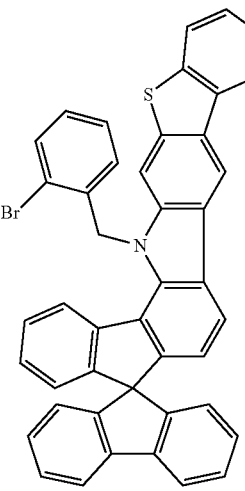 | 87% |
| 3d | 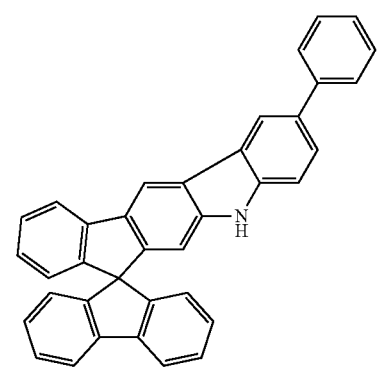 [SMILES: c1ccc(-c2ccc3[nH]c4cc5c(cc4c3c2)-c2ccccc2C52c3ccccc3-c3ccccc32)cc1] | 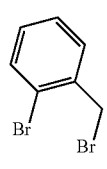  3433-80-5 | 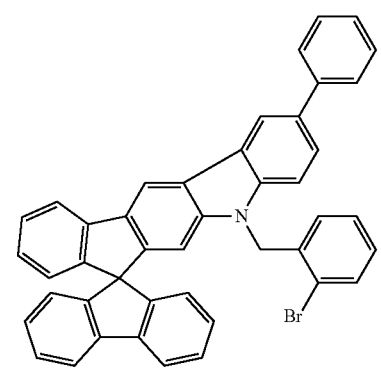 [SMILES: Brc1ccccc1Cn1c2ccc(-c3ccccc3)cc2c2cc3c(cc21)C1(c2ccccc2-c2ccccc21)c1ccccc1-3] | 92% |
| 3e | 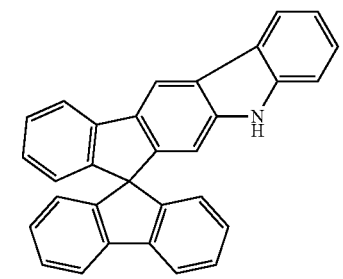 [SMILES: c1ccc2c(c1)-c1ccccc1C21c2ccccc2-c2cc3c(cc21)[nH]c1ccccc13] | 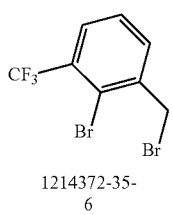 [SMILES: FC(F)(F)c1cccc(CBr)c1Br]  1214372-35-6 | 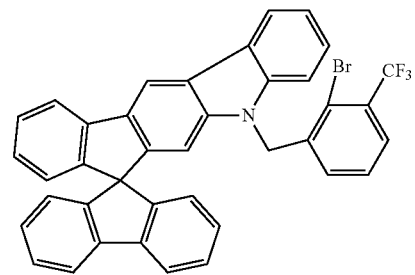 [SMILES: FC(F)(F)c1cccc(Cn2c3ccccc3c3cc4c(cc32)C2(c3ccccc3-c3ccccc32)c2ccccc2-4)c1Br] | 90% |

-continued

| Ex. | Reactant 1 | Reactant 2 | Product | Yield |
|---|---|---|---|---|
| 3f | | 172976-02-2<br>2 eq | | 90% |
| 3g | | 202805-71-8 | | 82% |
| 3h | | 3433-80-5<br>2 eq | | 88% |

| Ex. | Reactant 1 | Reactant 2 | Product | Yield |
|---|---|---|---|---|
| 3i | | 3433-80-5 | | 79% |

Example 4a: Cyclization

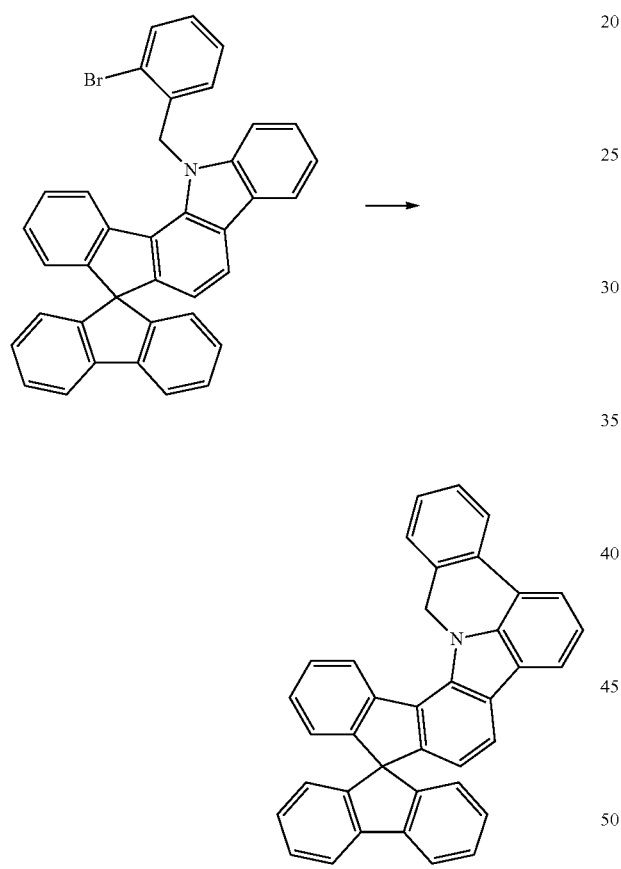

A 1 L four-neck flask is initially charged with 29 g (50 mmol) of 3a and 9.90 g (101 mmol) of potassium acetate in 500 mL of DMF, and argon is passed through for 30 minutes. Subsequently, 1.75 g (1.51 mmol) of Pd(PPh$_3$)$_4$ are added and the mixture is heated under reflux for 16 h until conversion is complete. The reaction mixture is cooled down to room temperature and hydrolyzed with 400 mL of water. The precipitated solid is filtered and washed with water. After drying under reduced pressure, the product is obtained as a gray solid. Yield: 4.7 g (50.0 mmol, corresponding to 99% of theory).

In an analogous manner, it is possible to obtain the following compounds:

| Ex. | Reactant 1 | Product | Yield |
|---|---|---|---|
| 4b | 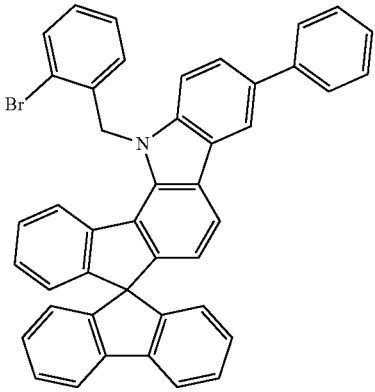 [SMILES: Brc1ccccc1Cn1c2ccc(-c3ccccc3)cc2c2ccc3c(c21)-c1ccccc1C31c2ccccc2-c2ccccc21] | 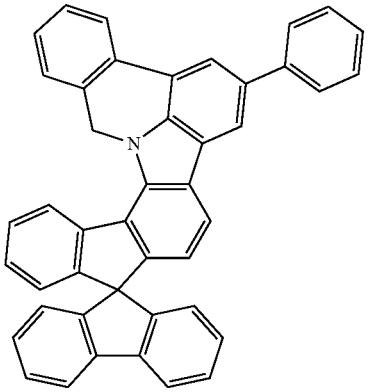 [SMILES: c1ccc(-c2cc3c4c(c2)c2ccc5c(c2n4Cc2ccccc2-3)-c2ccccc2C52c3ccccc3-c3ccccc32)cc1] | 80% |
| 4c | 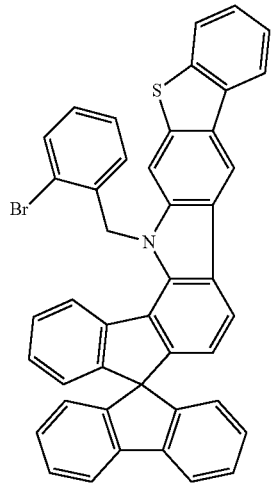 [SMILES: Brc1ccccc1Cn1c2cc3sc4ccccc4c3cc2c2ccc3c(c21)-c1ccccc1C31c2ccccc2-c2ccccc21] | 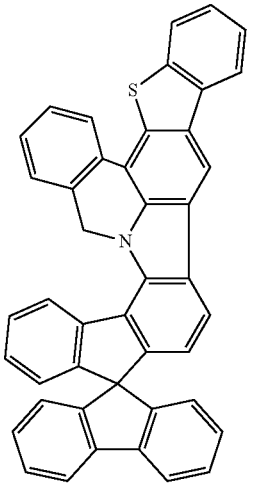 [SMILES: c1ccc2c(c1)Cn1c3c4c(ccc3c3cc5c(sc6ccccc65)c-2c31)C1(c2ccccc2-c2ccccc21)c1ccccc1-4] | 84% |
| 4d | 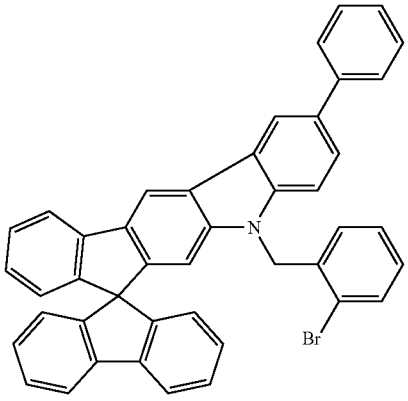 [SMILES: Brc1ccccc1Cn1c2ccc(-c3ccccc3)cc2c2cc3c(cc21)C1(c2ccccc2-c2ccccc21)c1ccccc1-3] | 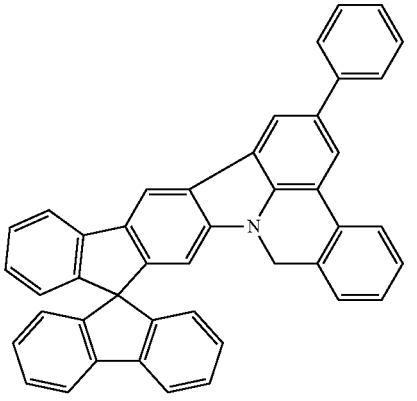 [SMILES: c1ccc(-c2cc3c4c(c2)c2cc5c(cc2n4Cc2ccccc2-3)C2(c3ccccc3-c3ccccc32)c2ccccc2-5)cc1] | 85% |
| 4e | 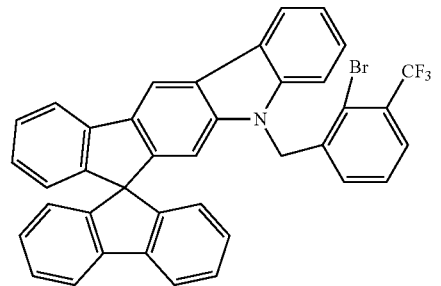 [SMILES: FC(F)(F)c1cccc(Cn2c3ccccc3c3cc4c(cc32)C2(c3ccccc3-c3ccccc32)c2ccccc2-4)c1Br] | 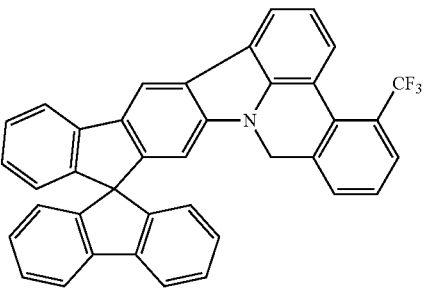 [SMILES: FC(F)(F)c1cccc2c1-c1cccc3c4cc5c(cc4n(c13)C2)C1(c2ccccc2-c2ccccc21)c1ccccc1-5] | 81% |

| Ex. | Reactant 1 | Product | Yield |
|---|---|---|---|
| 4f | 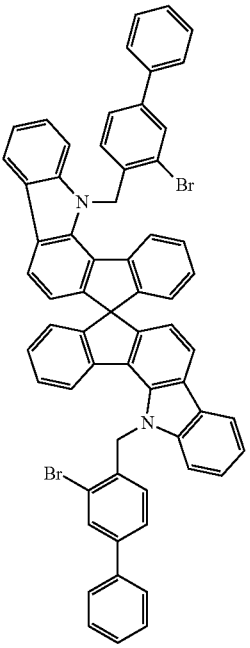 [SMILES: Brc1cc(-c2ccccc2)ccc1Cn1c2ccccc2c2ccc3c(c21)-c1ccccc1C31c2ccccc2-c2c1ccc1c3ccccc3n(Cc3ccc(-c4ccccc4)cc3Br)c21] | 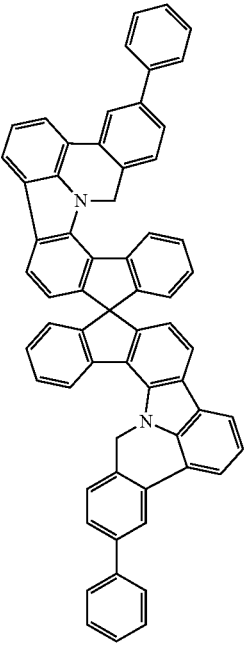 [SMILES: c1ccc(-c2ccc3c(c2)-c2cccc4c5ccc6c(c5n(c24)C3)-c2ccccc2C62c3ccccc3-c3c2ccc2c4cccc5c4n(c32)Cc2ccc(-c3ccccc3)cc2-5)cc1] | 88% |
| 4g | 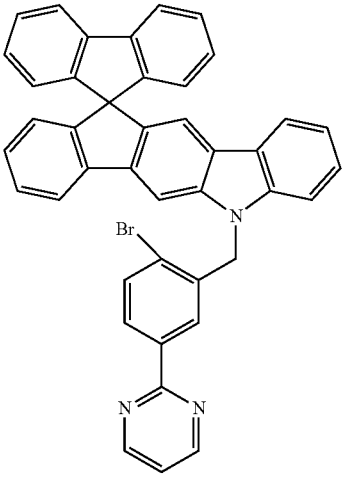 [SMILES: Brc1ccc(-c2ncccn2)cc1Cn1c2ccccc2c2cc3c(cc21)-c1ccccc1C31c2ccccc2-c2ccccc21] | 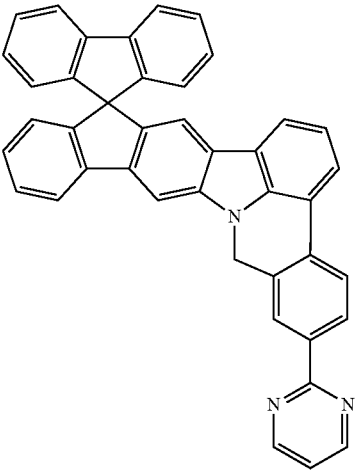 [SMILES: c1cnc(-c2ccc3c(c2)Cn2c4cc5c(cc4c4cccc-3c42)C2(c3ccccc3-c3ccccc32)c2ccccc2-5)nc1] | 79% |
| 4h | 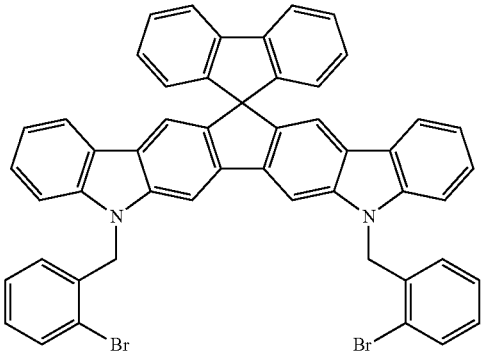 [SMILES: Brc1ccccc1Cn1c2ccccc2c2cc3c(cc21)-c1cc2c(cc1C31c3ccccc3-c3ccccc31)c1ccccc1n2Cc1ccccc1Br] | 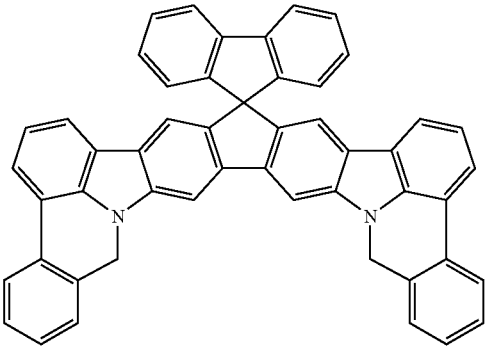 [SMILES: c1ccc2c(c1)Cn1c3cc4c(cc3c3cccc-2c31)C1(c2ccccc2-c2ccccc21)c1cc2c3cccc5c3n(c2cc1-4)Cc1ccccc1-5] | 78% |

| Ex. | Reactant 1 | Product | Yield |
|---|---|---|---|
| 4i | (structure) | (structure) | 76% |

Example 5a: Oxidation

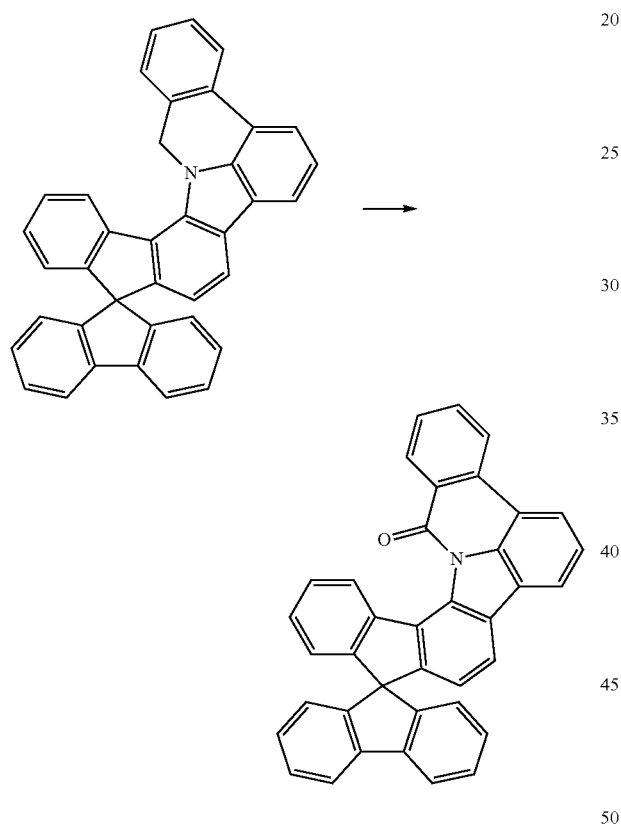

In a 1 L four-neck flask, 23.5 g (47.6 mmol) of 4a are dissolved in 500 mL of dichloromethane/water (1:1). Subsequently, 17.5 g (47.6 mmol) of dibenzo-18-crown-6 and, in portions, 91.0 g (576 mmol) of potassium permanganate are added and the mixture is stirred at room temperature for 24 h and under reflux for 4 days. After cooling to room temperature, the solvents are removed under reduced pressure. The solid obtained is subjected to hot extraction with toluene. The precipitated solid is filtered off and washed four times with 200 mL of cold acetonitrile. This is followed by hot extraction with toluene up to an HPLC purity of >99.9% and recrystallization. After subliming twice (340° C. at <10$^4$ bar), the product is obtained in an HPLC purity of >99.9% as a white solid. Yield: 3 g (7 mmol, corresponding to 15%).

In an analogous manner, it is possible to prepare the following compounds:

| Ex. | Reactant 1 | Product | Yield |
|---|---|---|---|
| 5b | 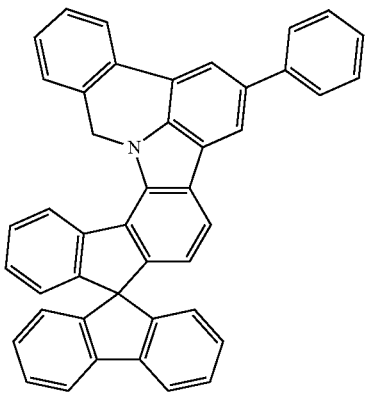 [SMILES: c1ccc(-c2cc3c4c(c2)c2ccc5c(c2n4Cc2ccccc2-3)-c2ccccc2C52c3ccccc3-c3ccccc32)cc1] | 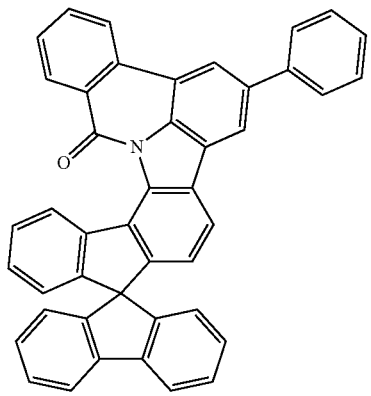 [SMILES: O=c1c2ccccc2c2cc(-c3ccccc3)cc3c4ccc5c(c4n1c23)-c1ccccc1C51c2ccccc2-c2ccccc21] | 23% |
| 5c | 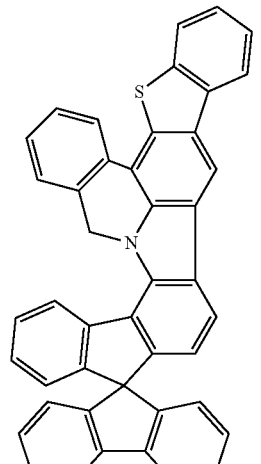 | 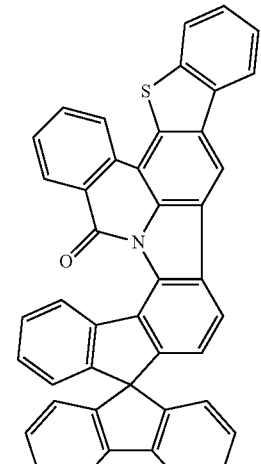 | 24% |
| 5d | 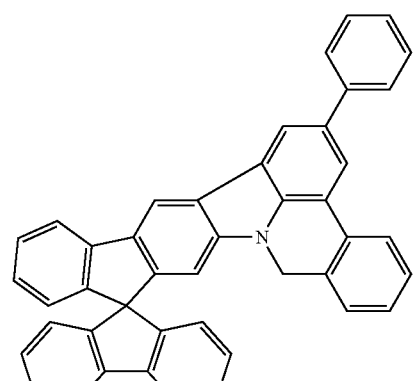 | 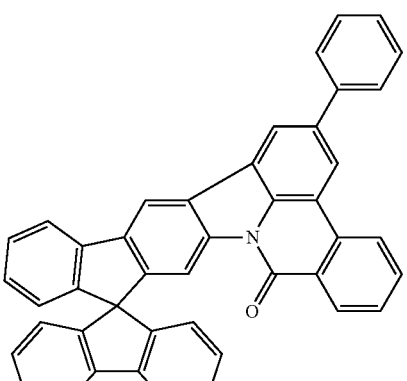 | 26% |
| 5e | 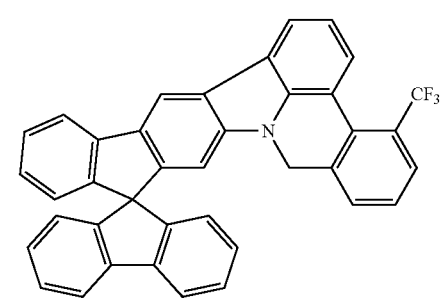 [SMILES: FC(F)(F)c1cccc2c1-c1cccc3c4cc5c(cc4n(c13)C2)C1(c2ccccc2-c2ccccc21)c1ccccc1-5] | 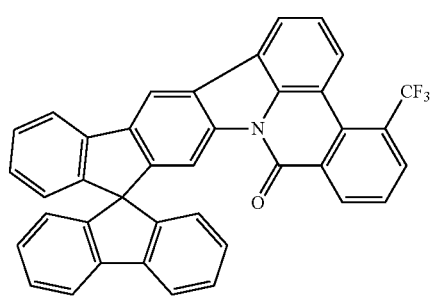 [SMILES: O=c1c2cccc(C(F)(F)F)c2c2cccc3c4cc5c(cc4n1c32)C1(c2ccccc2-c2ccccc21)c1ccccc1-5] | 21% |

-continued

| Ex. | Reactant 1 | Product | Yield |
|---|---|---|---|
| 5f | | | 23% |
| 5g | | | 18% |
| 5h | | | 31% |

| Ex. | Reactant 1 | Product | Yield |
|---|---|---|---|
| 5i | | | 23% |

Method 2:

Example 6a: Nucleophilic Substitution

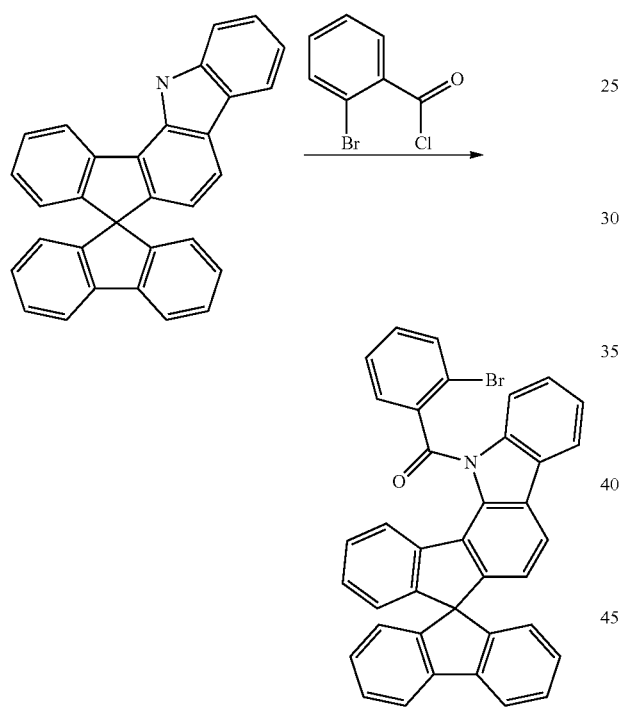

2.1 g (52.5 mmol) of 60% NaH in mineral oil are dissolved in 500 mL of THF under a protective atmosphere. 33.8 g (50 mmol) of compound 2a and 11.5 g (52.5 mmol) of 15-crown-5 dissolved in 200 mL of THF are added. After 1 h at room temperature, a solution of 12 g (55 mmol) of 2-bromobenzoyl chloride in 250 mL of THF is added dropwise. The reaction mixture is stirred at room temperature for 18 h. After this time, the reaction mixture is poured onto ice and extracted three times with dichloromethane. The combined organic phases are dried over $Na_2SO_4$ and concentrated. The residue is subjected to hot extraction with toluene and recrystallized from toluene/n-heptane. Yield: 17 g (29 mmol), 60%; purity: about 98% by $^1H$ NMR.

In an analogous manner, it is possible to obtain the following compounds:

| Ex. | Reactant 1 | Reactant 2 | Product | Yield |
|---|---|---|---|---|
| 6b | 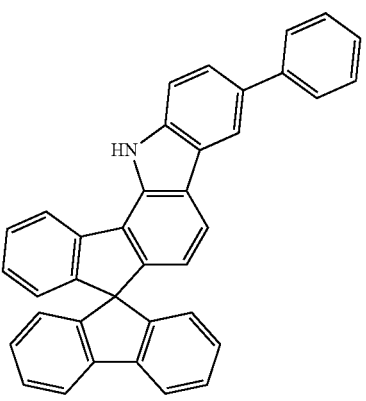 [SMILES: c1ccc(-c2ccc3[nH]c4c5c(ccc4c3c2)C2(c3ccccc3-c3ccccc32)c2ccccc2-5)cc1] | 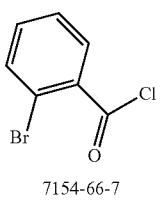 7154-66-7 | 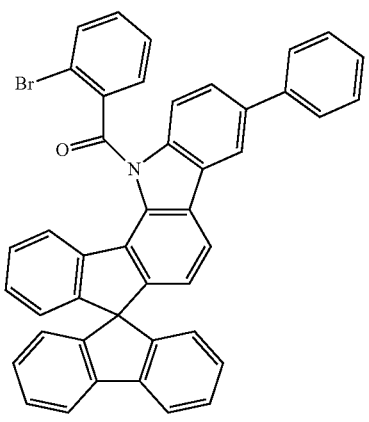 [SMILES: O=C(c1ccccc1Br)n1c2ccc(-c3ccccc3)cc2c2ccc3c(c21)-c1ccccc1C31c2ccccc2-c2ccccc21] | 68% |
| 6c | 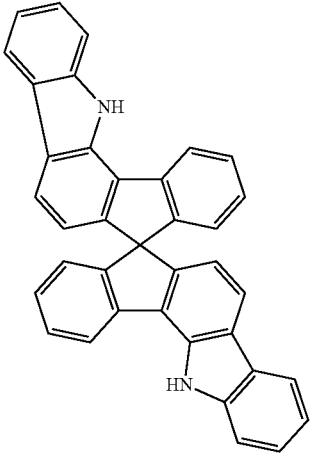 [SMILES: c1ccc2c(c1)-c1c(ccc3c1[nH]c1ccccc13)C21c2ccccc2-c2c1ccc1c2[nH]c2ccccc21] | 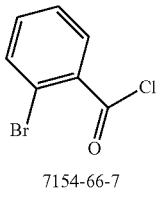 7154-66-7 | 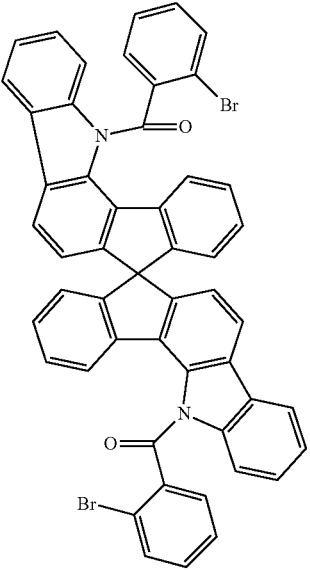 [SMILES: O=C(c1ccccc1Br)n1c2ccccc2c2ccc3c(c21)-c1ccccc1C31c2ccccc2-c2c1ccc1c3ccccc3n(C(=O)c3ccccc3Br)c21] | 64% |
| 6d | 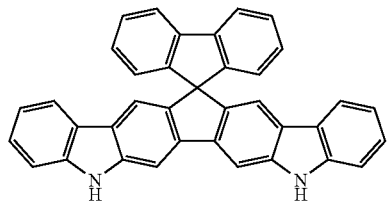 [SMILES: c1ccc2c(c1)-c1ccccc1C21c2cc3c(cc2-c2cc4[nH]c5ccccc5c4cc21)[nH]c1ccccc13] | 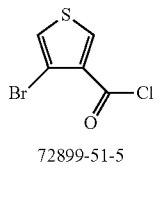 72899-51-5 | 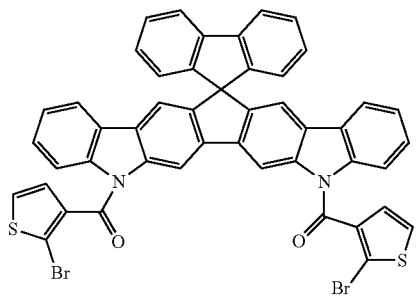 [SMILES: O=C(c1ccsc1Br)n1c2ccccc2c2cc3c(cc21)-c1cc2c(cc1C31c3ccccc3-c3ccccc31)c1ccccc1n2C(=O)c1ccsc1Br] | 63% |

Example 7a: Cyclization

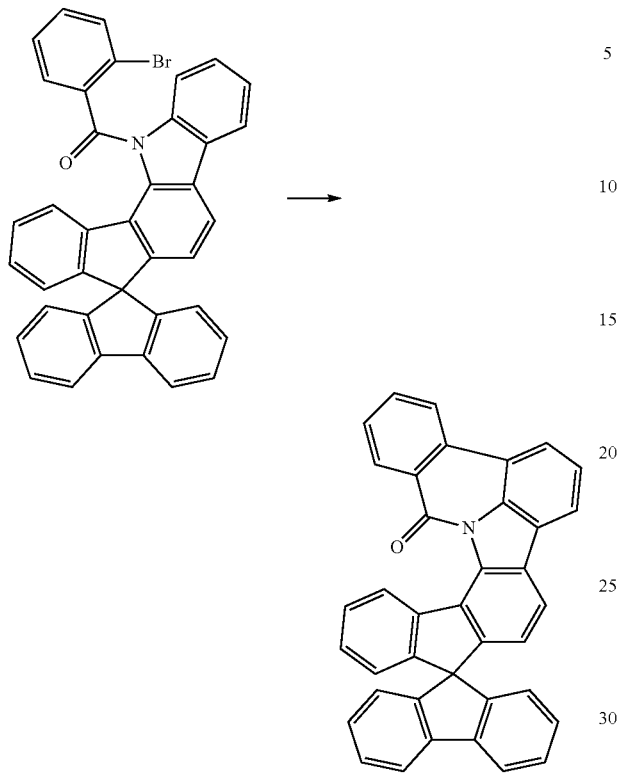

Under protective gas, 43 mL of tributyltin hydride (16 mmol) and 30 g (12-5 mmol) of 1,1'-azobis(cyclohexane-1-carbonitrile) in 600 mL of toluene are added dropwise over the course of 4 h to a boiling solution of 7.4 g (12.5 mmol) of compound 5a in 600 mL of toluene. This is followed by heating under reflux for 3 h. After this time, the reaction mixture is poured onto ice and extracted three times with dichloromethane. The combined organic phases are dried over $Na_2SO_4$ and concentrated. The residue is recrystallized from toluene and from dichloromethane/iso-propanol and finally sublimed under high vacuum; purity is 99.9%. Yield: 4.2 g (8.2 mmol), 66%.

In an analogous manner, it is possible to obtain the following compounds:

| Ex. | Reactant 1 | Product | Yield |
|---|---|---|---|
| 7b | | | 68% |

-continued

| Ex. | Reactant 1 | Product | Yield |
|---|---|---|---|
| 7c | 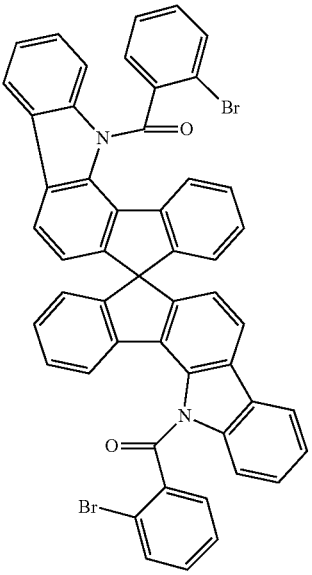 [SMILES: O=C(c1ccccc1Br)n1c2ccccc2c2ccc3c(c21)-c1ccccc1C31c2ccccc2-c2c1ccc1c3ccccc3n(C(=O)c3ccccc3Br)c21] | 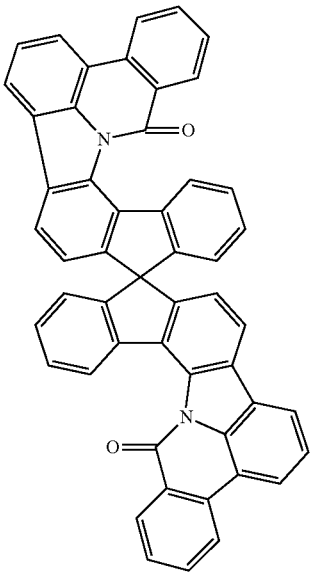 [SMILES: O=c1c2ccccc2c2cccc3c4ccc5c(c4n1c23)-c1ccccc1C51c2ccccc2-c2c1ccc1c3cccc4c5ccccc5c(=O)n(c21)c43] | 64% |
| 7d | 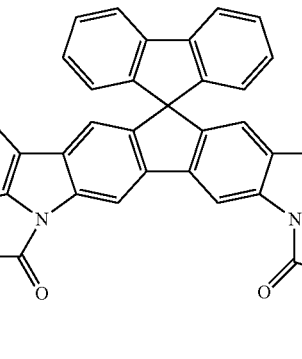 | 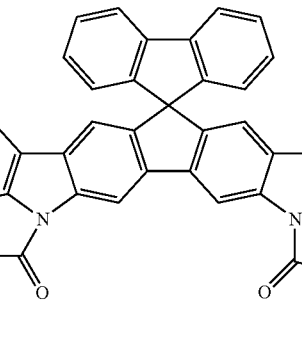 | 63% |

Production of the OLEDs

In examples C1 to I11 which follow (see tables 1 and 2), the data of various OLEDs are presented.

Pretreatment for Examples C1-I11:

Glass plaques coated with structured ITO (indium tin oxide) of thickness 50 nm, for improved processing, are coated with 20 nm of PEDOT:PSS (poly(3,4-ethylenedioxythiophene) poly(styrenesulfonate), purchased as CLEVIOS™ P VP AI 4083 from Heraeus Precious Metals GmbH Deutschland, spun on from aqueous solution). These coated glass plates form the substrates to which the OLEDs are applied.

The OLEDs basically have the following layer structure: substrate/hole transport layer (HTL)/optional interlayer (IL)/electron blocker layer (EBL)/emission layer (EML)/optional hole blocker layer (HBL)/electron transport layer (ETL)/optional electron injection layer (EIL) and finally a cathode. The cathode is formed by an aluminum layer of thickness 100 nm. The exact structure of the OLEDs can be found in Table 1. The materials used for production of the OLEDs are shown in Table 3.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as 5e:IC2:TEG1 (45%:45%:10%) mean here that the material from example 5e is present in the layer in a proportion by volume of 45%, the material IC2 in a proportion by volume of 45% and TEG1 in a proportion by volume of 10%. Analogously, the electron transport layer may also consist of a mixture of two materials.

The OLEDs are characterized in a standard manner. For this purpose, the electroluminescence spectra, the current efficiency (measured in cd/A), the power efficiency (measured in lm/W) and the external quantum efficiency (EQE, measured in percent) are as a function of luminance, calculated from current-voltage-luminance characteristics (IUL characteristics) assuming Lambertian radiation characteristics. The electroluminescence spectra are determined at a luminance of 1000 cd/m$^2$, and the CIE 1931 x and y color coordinates are calculated therefrom. The parameter U1000 in Table 2 refers to the voltage which is required for a luminance of 1000 cd/m$^2$. CE1000 and PE1000 respectively refer to the current and power efficiencies which are achieved at 1000 cd/m$^2$. Finally, EQE 1000 refers to the external quantum efficiency at an operating luminance of 1000 cd/m$^2$.

The data for the various OLEDs are collated in Table 2. Examples C1-C2 are comparative examples according to the prior art; examples I1-I11 show data of OLEDs of the invention.

Some of the examples are elucidated in detail hereinafter, in order to illustrate the advantages of the OLEDs of the invention.

Use of Mixtures of the Invention in the Emission Layer of Phosphorescent OLEDs

The materials of the invention, when used as matrix materials in phosphorescent OLEDs, give significant improvements in voltage and power efficiency over the prior art. By using the compound 5d of the invention in combination with the green-emitting dopant TEG1, it is possible to observe a significant improvement in voltage and power efficiency over the prior art (C1, C2) (example I1).

TABLE 1

Structure of the OLEDs

| Ex. | HTL thickness | IL thickness | EBL thickness | EML thickness | HBL thickness | ETL thickness | EIL thickness |
|---|---|---|---|---|---|---|---|
| C1 | SpA1 70 nm | HATCN 5 nm | SpMA1 90 nm | SdT1:TEG1 (90%:10%) 40 nm | — | ST2:LiQ (50%:50%) 30 nm | — |
| C2 | SpA1 70 nm | HATCN 5 nm | SpMA1 90 nm | SdT2:TEG1 (90%:10%) 40 nm | — | ST2:LiQ (50%:50%) 30 nm | — |
| I1 | SpA1 70 nm | HATCN 5 nm | SpMA1 90 nm | 5d:TEG1 (90%:10%) 40 nm | — | ST2:LiQ (50%:50%) 30 nm | — |
| I2 | SpA1 90 nm | HATCN 5 nm | SpMA1 130 nm | 5a:TER1 (92%:8%) 40 nm | — | ST2:LiQ (50%:50%) 40 nm | — |
| I3 | SpA1 90 nm | HATCN 5 nm | SpMA1 130 nm | 5b:TER1 (92%:8%) 40 nm | — | ST2:LiQ (50%:50%) 40 nm | — |
| I4 | SpA1 70 nm | HATCN 5 nm | SpMA1 90 nm | IC1:TEG1 (90%:10%) 30 nm | — | 5c:ST2 (50%:50%) 40 nm | LiQ 3 nm |
| I5 | SpA1 70 nm | HATCN 5 nm | SpMA1 90 nm | 5e:IC2:TEG1 (45%:45%:10%) 40 nm | — | ST2:LiQ (50%:50%) 30 nm | — |
| I6 | SpA1 70 nm | HATCN 5 nm | SpMA1 90 nm | 5f:TEG1 (90%:10%) 40 nm | — | ST2:LiQ (50%:50%) 30 nm | — |
| I7 | SpA1 70 nm | HATCN 5 nm | SpMA1 90 nm | 5d:TEG1 (90%:10%) 40 nm | — | ST2:LiQ (50%:50%) 30 nm | — |
| I8 | SpA1 70 nm | HATCN 5 nm | SpMA1 90 nm | IC1:TEG1 (90%:10%) 30 nm | — | 5h:ST1 (50%:50%) 40 nm | LiQ 3 nm |
| I9 | SpA1 70 nm | HATCN 5 nm | SpMA1 90 nm | IC1:TEG1 (90%:10%) 30 nm | 5i 10 nm | ST2:LiQ (50%:50%) 30 nm | — |
| I10 | SpA1 70 nm | HATCN 5 nm | SpMA1 90 nm | IC1:TEG1 (90%:10%) 30 nm | — | 7c:ST2 (50%:50%) 40 nm | LiQ 3 nm |
| I11 | SpA1 70 nm | HATCN 5 nm | SpMA1 90 nm | 7d:IC2:TEG1 (45%:45%:10%) 40 nm | — | ST2:LiQ (50%:50%) 30 nm | — |

| Ex | U1000 (V) | CE1000 (cd/A) | PE1000 (lm/W) | EQE 1000 | CIE x/y at 1000 cd/m$^2$ |
|---|---|---|---|---|---|
| C1 | 5.3 | 46 | 27 | 12.9% | 0.33/0.62 |
| C2 | 3.8 | 52 | 43 | 14.5% | 0.33/0.62 |
| I1 | 3.4 | 54 | 50 | 14.7% | 0.34/0.63 |
| I2 | 5.4 | 13 | 8 | 13.1% | 0.66/0.34 |
| I3 | 4.6 | 13 | 9 | 12.7% | 0.67/0.33 |
| I4 | 3.5 | 59 | 53 | 16.2% | 0.34/0.63 |
| I5 | 3.4 | 60 | 55 | 16.6% | 0.33/0.62 |
| I6 | 4.2 | 47 | 35 | 13.2% | 0.37/0.60 |
| I7 | 3.3 | 57 | 54 | 15.2% | 0.33/0.63 |
| I8 | 3.4 | 60 | 55 | 16.4% | 0.34/0.63 |
| I9 | 3.8 | 60 | 50 | 16.0% | 0.33/0.63 |
| I10 | 3.5 | 59 | 53 | 15.9% | 0.34/0.62 |
| I11 | 3.4 | 58 | 54 | 15.5% | 0.34/0.63 |

TABLE 3
Structural formulae of the materials for the OLEDs
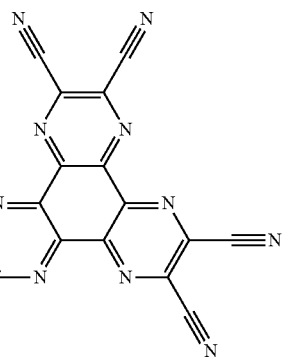
HATCN
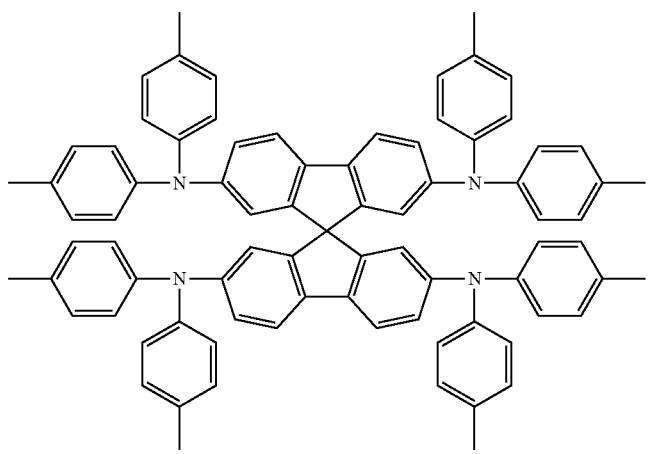
SpA1
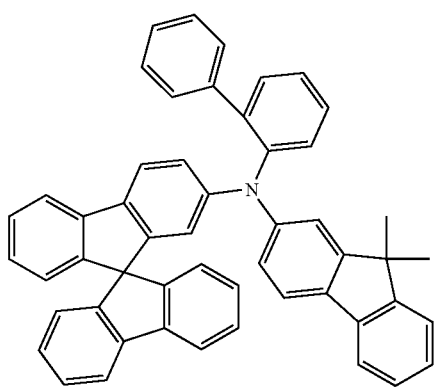 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
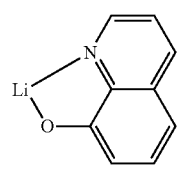
LiQ TABLE 3-continued
Structural formulae of the materials for the OLEDs
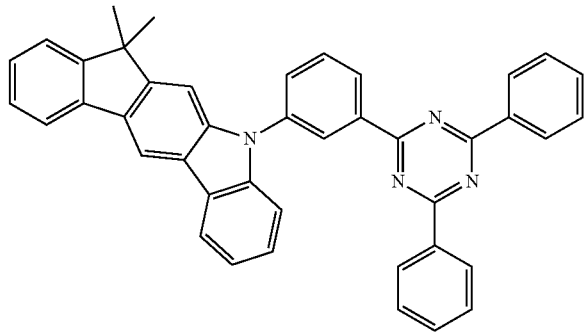 [SMILES: CC1(C)c2ccccc2-c2cc3c4ccccc4n(-c4cccc(-c5nc(-c6ccccc6)nc(-c6ccccc6)n5)c4)c3cc21]
IC2
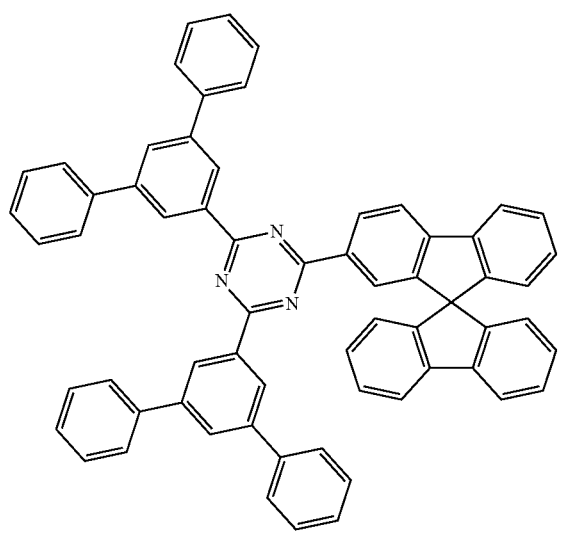 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
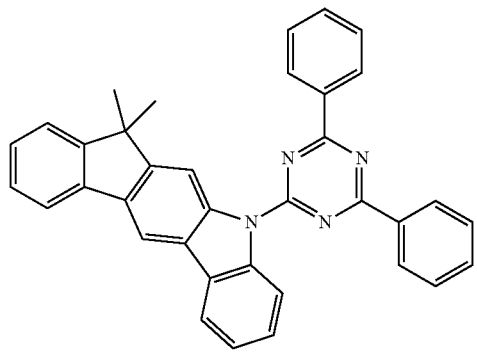 [SMILES: CC1(C)c2ccccc2-c2cc3c4ccccc4n(-c4nc(-c5ccccc5)nc(-c5ccccc5)n4)c3cc21]
IC1

TABLE 3-continued
Structural formulae of the materials for the OLEDs
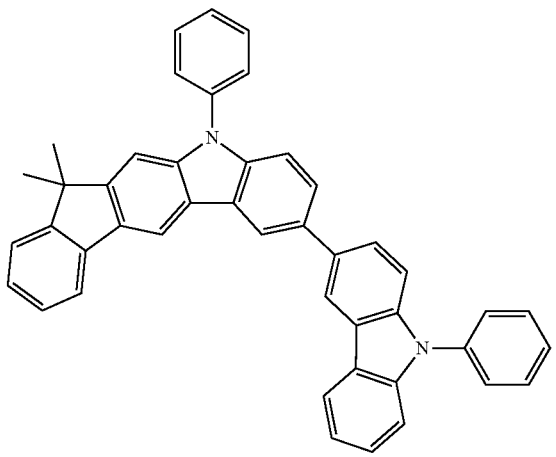 [SMILES: CC1(C)c2ccccc2-c2cc3c4cc(-c5ccc6c(c5)c5ccccc5n6-c5ccccc5)ccc4n(-c4ccccc4)c3cc21]
IC3
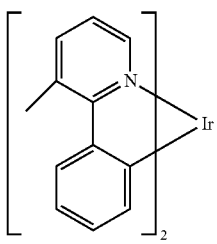
TEG1
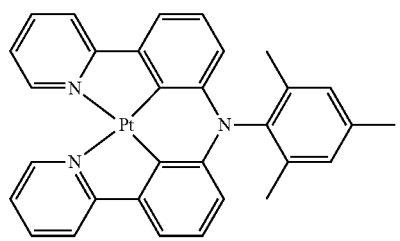
TER1
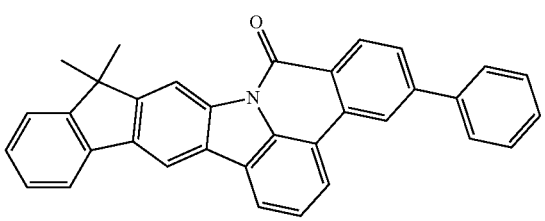 [SMILES: CC1(C)c2ccccc2-c2cc3c4cccc5c6cc(-c7ccccc7)ccc6c(=O)n(c3cc21)c54]
SdT1
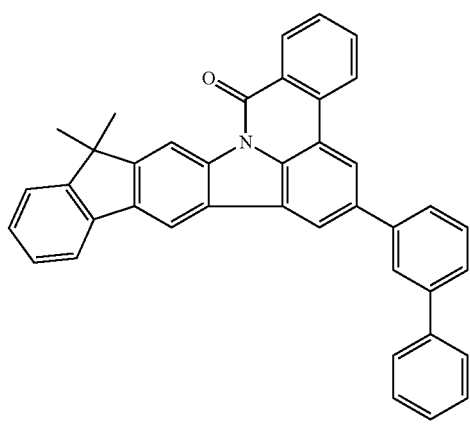 [SMILES: CC1(C)c2ccccc2-c2cc3c4cc(-c5cccc(-c6ccccc6)c5)cc5c6ccccc6c(=O)n(c3cc21)c54]
SdT2

TABLE 3-continued
Structural formulae of the materials for the OLEDs
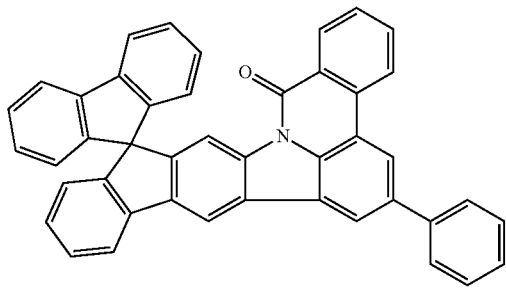 [SMILES: O=c1c2ccccc2c2cc(-c3ccccc3)cc3c4cc5c(cc4n1c23)C1(c2ccccc2-c2ccccc21)c1ccccc1-5]
5d
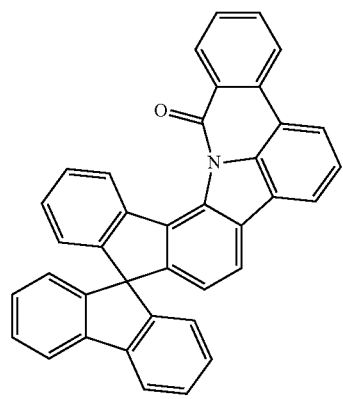 [SMILES: O=c1c2ccccc2c2cccc3c4ccc5c(c4n1c23)-c1ccccc1C51c2ccccc2-c2ccccc21]
5a
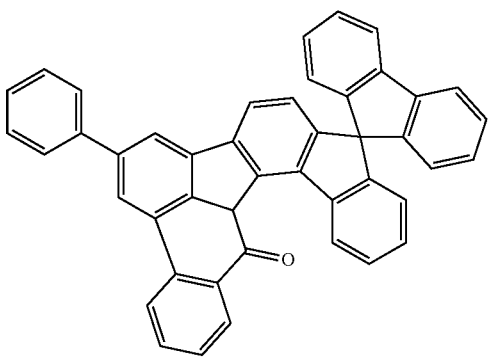 [SMILES: O=C1c2ccccc2-c2cc(-c3ccccc3)cc3c2C1c1c-3ccc2c1-c1ccccc1C21c2ccccc2-c2ccccc21]
5b
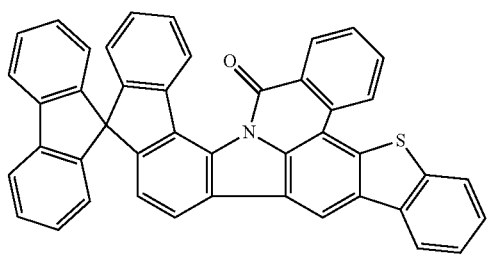 [SMILES: O=c1c2ccccc2c2c3sc4ccccc4c3cc3c4ccc5c(c4n1c32)-c1ccccc1C51c2ccccc2-c2ccccc21]
5c
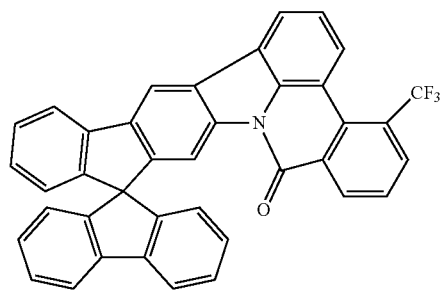 [SMILES: O=c1c2cccc(C(F)(F)F)c2c2cccc3c4cc5c(cc4n1c32)C1(c2ccccc2-c2ccccc21)c1ccccc1-5]
5e TABLE 3-continued
Structural formulae of the materials for the OLEDs
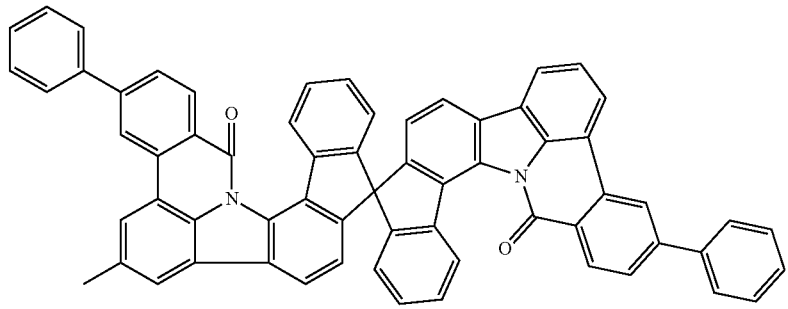 [SMILES: Cc1cc2c3cc(-c4ccccc4)ccc3c(=O)n3c4c5c(ccc4c(c1)c23)C1(c2ccccc2-c2c1ccc1c3cccc4c6cc(-c7ccccc7)ccc6c(=O)n(c21)c43)c1ccccc1-5]
5f
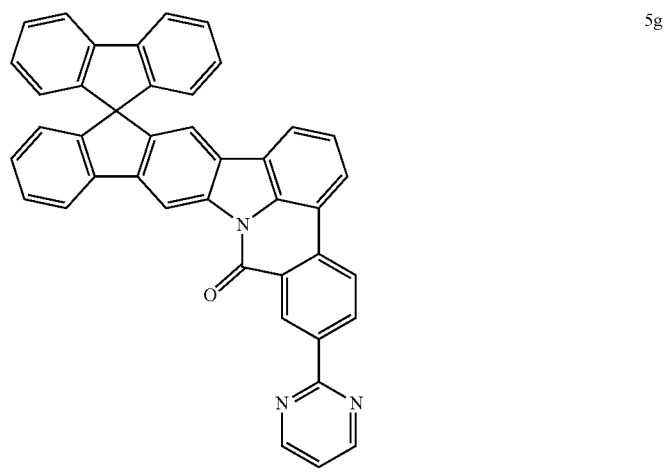
5g
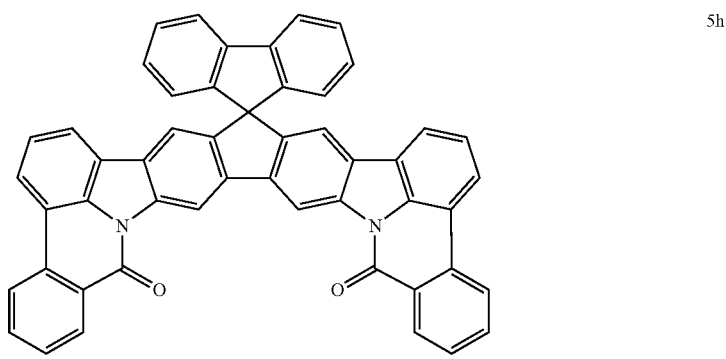
5h
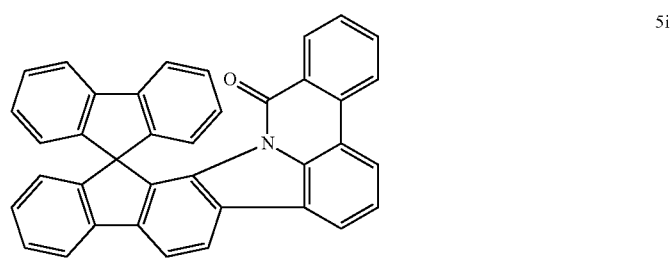
5i TABLE 3-continued Structural formulae of the materials for the OLEDs

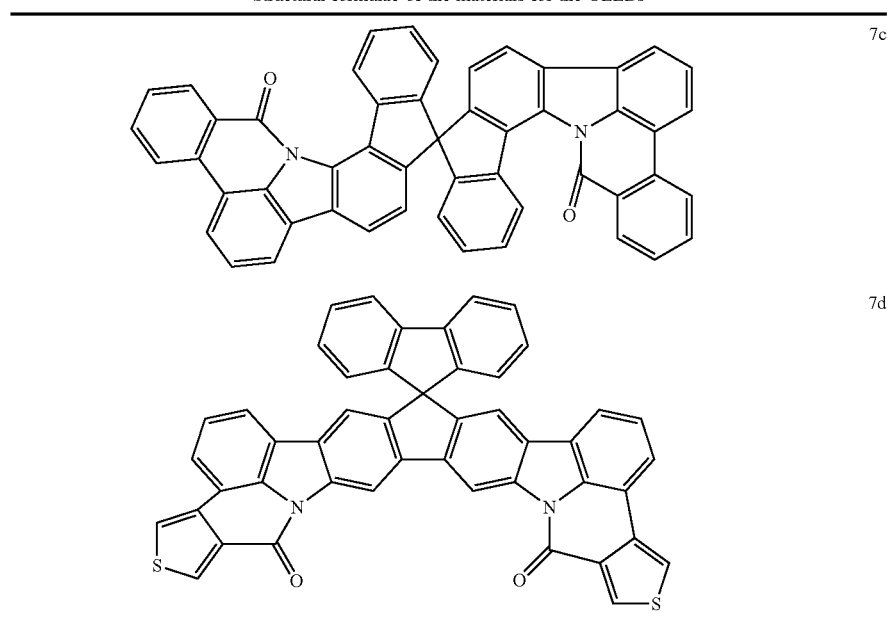

7c

7d

The invention claimed is:

1. A compound of formula (8)

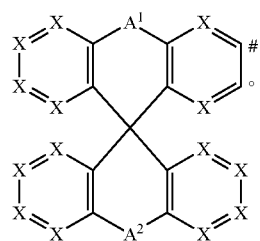

Formula (8)

wherein

X is the same or different at each instance and is CR or two adjacent X groups together are a group of the formula (2) with the proviso that the compound of the formula (8) contains at least one group of the formula (2)

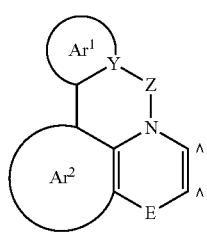

Formula (2)

where ^ indicates the positions to which the group of the formula (2) is fused to the compound of the formula (8);

$A^1$, $A^2$ is the same or different at each instance and is a single bond, $CR_2$, NR, O, S or C=O;

Z is C=O;

Y is C when $Ar^1$ is a 6-membered aryl or heteroaryl group, or is C or N when $Ar^1$ is a 5-membered heteroaryl group;

E is the same or different at each instance and is a single bond, $CR_2$, NR, O, S or C=O;

$Ar^1$ is the same or different at each instance and, together with the Y group and the carbon atom shown explicitly, is an aromatic or heteroaromatic ring system which has 5 to 24 aromatic ring atoms and may be substituted by one or more R radicals;

$Ar^2$ is the same or different at each instance and, together with the three carbon atoms shown explicitly, is an aromatic or heteroaromatic ring system which has 5 to 24 aromatic ring atoms and may be substituted by one or more R radicals;

G is the same or different at each instance and is CR or N;

R is the same or different at each instance and is selected from the group consisting of H, D, F, Cl, Br, I, CN, $NO_2$, $N(Ar^3)_2$, $N(R^1)_2$, C(=O)$Ar^3$, C(=O)$R^1$, P(=O)$(Ar^3)_2$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, each of which may be substituted by one or more $R^1$ radicals, where one or more nonadjacent $CH_2$ groups may be replaced by $R^1C=CR^1$, C≡C, $Si(R^1)_2$, C=O, C=$NR^1$, P(=O)($R^1$), SO, $SO_2$, $NR^1$, O, S or $CONR^1$ and where one or more hydrogen atoms may be replaced by D, F, Cl, Br, I, CN or $NO_2$, an aromatic or heteroaromatic ring system which has 5 to 40 aromatic ring atoms and may be substituted in each case by one or more $R^1$ radicals, an aryloxy or heteroaryloxy group which has 5 to 40 aromatic ring atoms and may be substituted by one or more $R^1$ radicals, or an aralkyl or heteroaralkyl group which has 5 to 40 aromatic ring atoms and may be substituted by one or more $R^1$ radicals, where it is optionally possible for two or more adjacent R substituents to form a monocyclic or polycyclic, aliphatic, aromatic or heteroaromatic ring system which may be substituted by one or more $R^1$ radicals;

$Ar^3$ is the same or different at each instance and is an aromatic or heteroaromatic ring system which has 5-30 aromatic ring atoms and may be substituted by one or more nonaromatic $R^1$ radicals; at the same time, two $Ar^3$ radicals bonded to the same nitrogen atom or phosphorus atom may also be bridged to one another by a single bond or a bridge selected from $N(R')$, $C(R^1)_2$ and O;

$R^1$ is the same or different at each instance and is selected from the group consisting of H, D, F, Cl, Br, I, CN, $NO_2$, $N(R^2)_2$, $C(=O)R^2$, $P(=O)(R^2)_2$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, each of which may be substituted by one or more $R^2$ radicals, where one or more nonadjacent $CH_2$ groups may be replaced by $R^2C=CR^2$, CC, $Si(R^2)_2$, C=O, $C=NR^2$, $P(=O)(R^2)$, SO, $SO_2$, $NR^2$, O, S or $CONR^2$ and where one or more hydrogen atoms may be replaced by D, F, Cl, Br, I, CN or $NO_2$, an aromatic or heteroaromatic ring system which has 5 to 40 aromatic ring atoms and may be substituted in each case by one or more $R^2$ radicals, an aryloxy or heteroaryloxy group which has 5 to 40 aromatic ring atoms and may be substituted by one or more $R^2$ radicals, or an aralkyl or heteroaralkyl group which has 5 to 40 aromatic ring atoms and may be substituted by one or more $R^2$ radicals, where it is optionally possible for two or more adjacent $R^1$ substituents to form a monocyclic or polycyclic, aliphatic, aromatic or heteroaromatic ring system which may be substituted by one or more $R^2$ radicals;

$R^2$ is selected from the group consisting of H, D, F, CN, an aliphatic hydrocarbyl radical having 1 to 20 carbon atoms, an aromatic or heteroaromatic ring system having 5 to 30 aromatic ring atoms, where two or more adjacent $R^2$ substituents together may form a mono- or polycyclic, aliphatic, aromatic or heteroaromatic ring system, and where ° represents the linkage to the nitrogen atom in the group of the formula (2), and # represents the linkage to the E group in the group of the formula (2).

2. The compound as claimed in claim 1, wherein $A^1$ and $A^2$ are single bonds.

3. The compound as claimed in claim 1 comprising exactly one or two groups of the formula (2).

4. The compound as claimed in claim 1, having the formula (8a)

Formula (8a)

where the symbols used have the definitions given in claim 1.

5. The compound as claimed in claim 1, having the formula (8b)

Formula (8b)

where the symbols used have the definitions given in claim 1.

6. The compound as claimed in claim 1, wherein in the group of the formula (2), Z is the same or different and is C=O or C=S, and in that E is a single bond, $CR_2$, C=O or NR.

7. The compound as claimed in claim 1, wherein $Ar^1$ is a group of the formula (13), (14), (15), (16) or (17)

Formula (13)

Formula (14)

Formula (15)

Formula (16)

Formula (17)

where the dotted bond indicates the linkage to Z and * indicates the position of the linkage to $Ar^2$;

and in that Ar² is a group of the formula (20), (21) or (22)

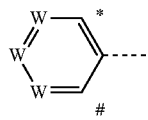
Formula (20)

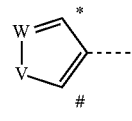
Formula (21)

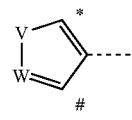
Formula (22)

where the dotted bond indicates the linkage to N, # indicates the position of the linkage to E and * indicates the linkage to Ar¹;

and in addition:

W is the same or different at each instance and is CR or N, or two adjacent W groups are a group of the following formula (18) or (19)

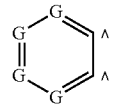
Formula (18)

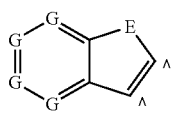
Formula (19)

where E is as defined in claim 1, but is not a single bond, G is the same or different at each instance and is CR or N and A indicate the corresponding adjacent W groups in the formula (13) to (17);

V is NR, O or S.

8. The compound as claimed in claim 1, wherein the group of the formula (2) is selected from the groups of the formulae (23) to (29):

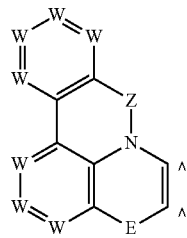
Formula (23)

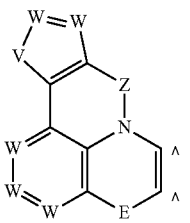
Formula (24)

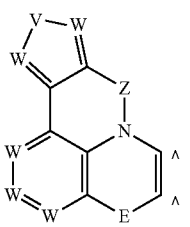
Formula (25)

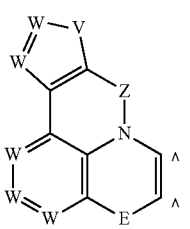
Formula (26)

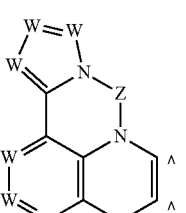
Formula (27)

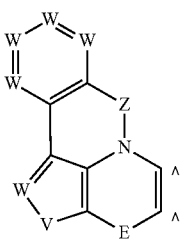
Formula (28)

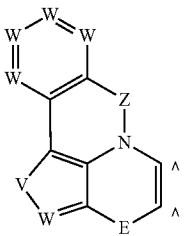
Formula (29)

where ˆ identifies the position of the linkage in formula (1) and the further symbols used are as defined in claim 1.

9. The compound as claimed in claim 1, wherein the group of the formula (2) is selected from the groups of the formulae (23a) to (29a):

Formula (23a)
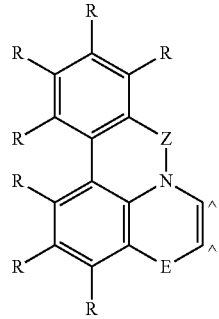

Formula (24a)
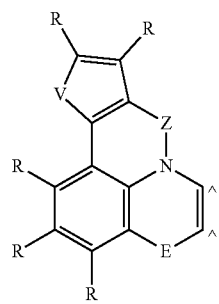

Formula (25a)
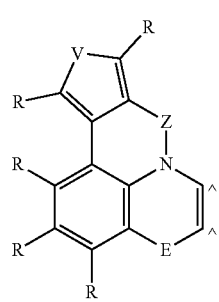

Formula (26a)
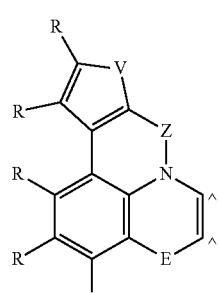

Formula (27a)
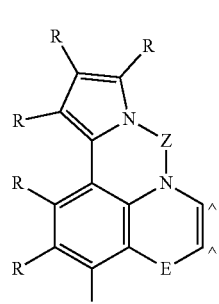

Formula (28a)
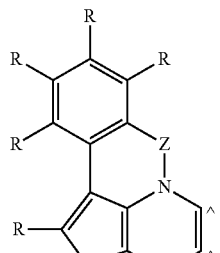

Formula (29a)
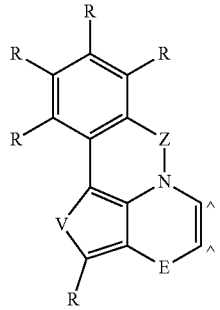

where the symbols used have the definitions given in claim 1.

10. The compound as claimed in claim 1, having the formula (8c)

Formula (8c)
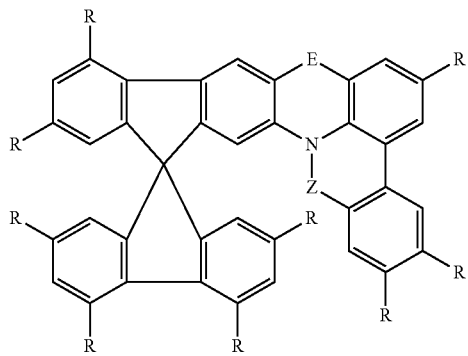

where the symbols used are as defined in claim 1.

11. The compound as claimed in claim 1, wherein all R radicals are H or in that one or two R radicals are an aromatic or heteroaromatic ring system which has 6 to 24 aromatic ring atoms and may be substituted in each case by one or more $R^1$ radicals, and the other R radicals are H.

12. An oligomer, polymer or dendrimer containing one or more of the compounds as claimed in claim 1, wherein one or more bonds of the compound to the polymer, oligomer or dendrimer are present in place of one or more R radicals.

13. A formulation comprising at least one compound as claimed in claim 1 and at least one further compound, especially a solvent or a mixture of two or more solvents.

14. A method comprising incorporating the compound as claimed in claim 1 in an electronic device.

15. An electronic device comprising at least one compound as claimed in claim 1.

16. The electronic device as claimed in claim 1, wherein the device is an organic electroluminescent device and the compound as claimed in claim 1 is used in an emitting layer as matrix material for fluorescent or phosphorescent emitters and/or in a hole blocker layer and/or in an electron transport layer.

17. The compound as claimed in claim 1, wherein in the group of the formula (2), E is a single bond, and $A^1$ and $A^2$ are single bonds.

18. The compound as claimed in claim 1, wherein $Ar^1$ is a group of the formula (13), (14), (15), (16) or (17)

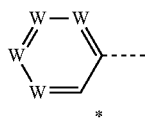

Formula (13)

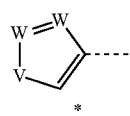

Formula (14)

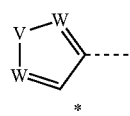

Formula (15)

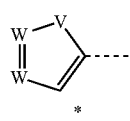

Formula (16)

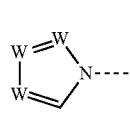

Formula (17)

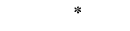

where the dotted bond indicates the linkage to Z and * indicates the position of the linkage to $Ar^2$;

and in that $Ar^2$ is a group of the formula (20), (21) or (22)

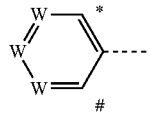

Formula (20)

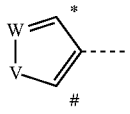

Formula (21)

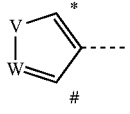

Formula (22)

where the dotted bond indicates the linkage to N, # indicates the position of the linkage to E and * indicates the linkage to $Ar^1$;

and in addition:

W is the same or different at each instance and is CR; and

V is NR, O or S.

19. The compound as claimed in claim 8, wherein the group of the formula (2) is a group of the formulae (23).

* * * * *